US007910318B2

(12) United States Patent
LePage et al.

(10) Patent No.: US 7,910,318 B2
(45) Date of Patent: Mar. 22, 2011

(54) METHODS OF DIAGNOSING OVARIAN CANCER AND KITS THEREFOR

(75) Inventors: Cecile LePage, Montreal (CA); Anne-Marie Mes-Masson, Dollard-Des-Ormeaux (CA); Diane Provencher, St-Basile-Le-Grand (CA); Patricia Tonin, Montreal (CA); Thomas Hudson, Toronto (CA)

(73) Assignees: The Royal Institution for the Advancement of Learning/McGill University, Montreal (CA); Val-Chum, S.E.C., Montreal (CA)

( * ) Notice: Subject to any disclaimer, the term of this patent is extended or adjusted under 35 U.S.C. 154(b) by 165 days.

(21) Appl. No.: 12/066,564

(22) PCT Filed: Sep. 15, 2006

(86) PCT No.: PCT/CA2006/001536
§ 371 (c)(1),
(2), (4) Date: Mar. 12, 2008

(87) PCT Pub. No.: WO2007/030949
PCT Pub. Date: Mar. 22, 2007

(65) Prior Publication Data
US 2008/0248501 A1     Oct. 9, 2008

Related U.S. Application Data

(60) Provisional application No. 60/716,941, filed on Sep. 15, 2005.

(51) Int. Cl.
*G01N 33/53*   (2006.01)
*C12Q 1/68*    (2006.01)

(52) U.S. Cl. ............................................. 435/7.1; 435/6

(58) Field of Classification Search ........................ None
See application file for complete search history.

(56) References Cited

U.S. PATENT DOCUMENTS

| 2004/0005563 | A1 | 1/2004 | Mack et al. |
| 2004/0010121 | A1 | 1/2004 | Birse et al. |
| 2005/0059013 | A1 | 3/2005 | Chan et al. |
| 2005/0069963 | A1 | 3/2005 | Lokshin et al. |

FOREIGN PATENT DOCUMENTS

| WO | WO2005/016126    | 2/2005 |
| WO | WO/2005/083440 A2 | 9/2005 |

OTHER PUBLICATIONS

Lu et al (Clinical Cancer Research, May 2004, 10:3291-3300).*
Le Page et al (Int. J. Cancer, 2006, 118:1750-1758).*
Ileri et al (Nephrol. Dial. Transplant, 2000, 15(9):A234).*
McIntosh et al (Gynecologic Oncology, 2004, 95:9-15).*
Barton et al (Clinical Cancer Research, 1997, 3:1579-1586).*
Akahiro et al (Int J Clin Oncol, 2004, 9(1): 42-46).*
Internet Citation, XP002232760, "GeneChip Human Genome U133 Set", Retrieved on Feb. 26, 2003.
Kaku et al., "Histological classification of ovarian cancer", Med Electron Microsc, (2003), vol. 36:9-17.
Kim et al., "Osteopontin as a potential diagnostic biomarker for ovarian cancer", Jama, (2002) vol. 287: 1671-1679.
Kruk et al., "A simplified method to culture human ovarian surface epithelium", Lab. Invest., (1990) vol. 63: 132-136.
Le Page et al., "Signature of a silent killer: expression profiling in epithelial ovarian cancer", Expert Rev. Mol. Diagn. vol. 4 No. 2: 157-167.
Le Page et al., "From gene profiling to diagnostic markers: IL-18 and FGF-2 complement . . . ", Int. J. Cancer (2006), vol. 118: 1750-1758.
Lounis et al., "Primary cultures of normal and tumoral human ovarian epithelium: A powerful tool for basic molecular studies", Exp. Cell Res., (1994), vol. 215: 303-309.
Lu et al., Selection of potential markers for epithelial ovarian cancer . . . , Clinical Cancer Research, (2004), vol. 10: 3291-3300.
McIntosh et al., "Combining CA 125 and SMR serum markers for diagnosis and early detection of ovarian carcinoma", Gynecol Oncol, (2004) vol. 95: 9-15.
Meyer et al., "Role of tumour markers in monitoring epithelial ovarian cancer", Br J Cancer, (2000), vol. 82: 1535-1538.
Modugno F. "Ovarian cancer and high-risk women-implications for prevention, screening, and early detection", Gynecol Oncol, (2003), vol. 91: 15-31.
Mok et al., "Prostasin, a potential serum marker for ovarian cancer: identification through microarray technology", J Natl Cancer Inst, (2001) vol. 93: 1458-1464.
Ouellet et al., "Discrimination between serous low malignant potential and invasive epithelial ovarian tumors using molecular profiling", Oncogene, vol. 24: 4672-4687.
Pfaffl M. W., "A new mathematical model for relative quantification in real-time RT-PCR", Nucleic Acids Res, (2001) vol. 29: 2002-2007.
Rosen et al., "Potential markers that complement expression of CA125 in epithelial ovarian cancer", Gynecologic Oncology, Academic Press, (2005), vol. 99, No. 2: 267-277.
Tamayo et al., "Interpreting patterns of gene expression with self-organizing maps: methods and application . . . ", Proc Natl Acad Sci, (1999), vol. 96: 2907-2912.
Woolas et al., "Combinations of multiple serum markers are superior to individual assays for discriminating malignant . . . ", Gynecol Oncol, (1995), vol. 59: 111-116.
Woolas et al., "Elevation of multiple serum markers in patients with stage I ovarian cancer", J Natl Cancer Inst, (1993) vol. 85: 1748-1751.
IPRP PCT/CA2006/001536, Mar. 22, 2007, Val-Chum, S.E.C. et al.
ISR PCT/CA2006/001536, Jan. 8, 2007.
EP06790705 Supp. EP search, Sep. 26, 2008, Val-Chum, S.E.C. et al.
Agarwal et al., "Familial recurrent molar pregnancy: a case report", Acta Obstet Gynecol Scand, (2004), vol. 83: 213-4.

(Continued)

*Primary Examiner* — Sean E Aeder
(74) *Attorney, Agent, or Firm* — Goudreau Gage Dubuc; Julie Gauvreau

(57) ABSTRACT

A method comprising: providing a biological sample from a subject (subject sample); and detecting the expression level of each of the markers FGF-2 and CA125 in the subject sample. A kit comprising means for detection of an expression level of each of markers CA125 and FGF-2 in a biological sample from a subject (subject sample), and instructions to use said markers in a method of the present invention.

21 Claims, 32 Drawing Sheets

OTHER PUBLICATIONS

Akahira et al., "Impact of serum interleukin-18 level as a prognostic indicator in patients . . . ", Int. Journal of Clinical Oncology, (2004), vol. 9: 942-946.

Auersperg et al., "Ovarian surface epithelium: biology, endocrinology, and pathology", Endocr Rev., (2001), vol. 22: 255-288.

Bast et al., "Monitoring human ovarian carcinoma with a combination of CA 125, CA 19-9, and carcinoembryonic antigen", Am J Obstet Gynecol, (1984), vol. 149: 553-559.

Chan Éric, "Integrating Transcriptomics and Proteomics", Genomics and Proteomics, (2006), pp. 1-6.

Chuaqui et al., "Histopathology and molecular biology of ovarian epithelial tumors", Ann Diagn Pathol, (1998), vol. 2: 195-207.

Crispens M. A., "Borderline ovarian tumours: a review of the recent literature", Curr Opin Obstet Gynecol, (2003), vol. 15: 39-43.

De Cecco et al., "Gene expression profiling of advanced ovarian cancer . . . ", Oncogene, (2004), vol. 23: 8171-8183.

Hellstrom et al. "The HE4 (WFDC2) protein is a biomarker for ovarian carcinoma", Cancer Res, (2003), vol. 63: 3695-3700.

Ileri et al., The predictive value of cancer antigen 125 (CA125), collagen III . . . , Nephrology Dialysis Transplantation, (2000) vol. 15 No. 9: A234.

Bast et al., "Monitoring human ovarian carcinoma with a combination of CA 125, CA 19-9, and carcinoembryonic antigen", Am. J. Obstet. Gynecol. (1984), vol. 149: 553-559.

Gaggero et al., "A novel isoform of pro-interleukin-18 expressed in ovarian tumors is resistant to caspase-1 and -4 processing", Oncogene, (2004), vol. 23: 7552-7560.

Yurkovestsky et al. "Development of a Multimarker Assay for Early Detection of Ovarian Cancer", Journal of Clinical Oncology, (2010), vol. 28(13): 2159-2166.

\* cited by examiner

Nucleic acid and polypeptide sequences of CA125

Nucleic acid sequence (SEQ ID No:1)

```
   1 aagcgttgca caattccccc aacctccata catacggcag ctcttctaga cacaggtttt
  61 cccaggtcaa atgcggggac cccagccata tctcccaccc tgagaaattt tggagtttca
 121 gggagctcag aagctctgca gaggccaccc tctctgaggg gattcttctt agacctccat
 181 ccagaggcaa atgttgacct gtccatgctg aaaccctcag gccttcctgg gtcatcttct
 241 cccacccgct ccttgatgac agggagcagg agcactaaag ccacaccaga atggattca
 301 ggactgacag gagccacctt gtcacctaag acatctacag gtgcaatcgt ggtgacagaa
 361 catactctgc cctttacttc cccagataag accttggcca gtcctacatc ttcggttgtg
 421 ggaagaacca cccagtcttt ggggtgatg tcctctgctc tccctgagtc aacctctaga
 481 ggaatgacac actccgagca aagaaccagc ccatcgctga gtcccaggt caatggaact
 541 ccctctagga actaccctgc tacaagcatg gtttcaggat tgagttcccc aaggaccagg
 601 accagttcca cagaaggaaa ttttaccaaa gaagcatcta catacacact cactgtagag
 661 accacaagtg gcccagtcac tgagaagtac acagtcccca ctgagacctc aacaactgaa
 721 ggtgacagca cagagacccc ctgggacaca agatatattc ctgtaaaaat cacatctcca
 781 atgaaaacat ttgcagattc aactgcatcc aaggaaaatg ccccagtgtc tatgactcca
 841 gctgagacca cagttactga ctcacatact ccaggaagga caaacccatc atttgggaca
 901 ctttattctt ccttccttga cctatcacct aaagggaccc caattccag aggtgaaaca
 961 agcctggaac tgattctatc aaccactgga tatccttct cctctcctga acctggctct
1021 gcaggacaca gcagaataag taccagtgcg cctttgtcat catctgcttc agttctcgat
1081 aataaaaatat cagagaccag catattctca ggccagagtc tcacctcccc tctgtctcct
1141 ggggtgcccg aggccagagc cagcacaatg cccaactcag ctatcccttt tccatgaca
1201 ctaagcaatg cagaaacaag tgccgaaagg gtcagaagca aatttcctc tctggggact
1261 ccatcaatat ccacaaagca gacagcagag actatcctta ccttccatgc cttcgctgag
1321 accatggata tacccagcac ccacatagcc aagactttgg cttcagaatg gttgggaagt
1381 ccaggtaccc ttggtggcac cagcacttca gcgctgacaa ccacatctcc atctaccact
1441 ttagtctcag aggagaccaa cacccatcac tccacgagtg gaaaggaaac agaaggaact
1501 ttgaatacat ctatgactcc acttgagacc tctgctcctg gagaagagtc cgaaatgact
1561 gccacttgg tccccactct aggttttaca actcttgaca gcaagatcag aagtccatct
1621 caggtctctt catcccaccc aacaagagag ctcagaacca caggcagcac tctgggagg
1681 cagagttcca gcacagctgc cacgggagc tctgacatcc tgagggcaac cacttccagc
1741 acctcaaaag catcatcatg gaccagtgaa agcacagctc agcaatttag tgaaccccag
1801 cacacacagt gggtggagac aagtcctagc atgaaaacag agaccccc agcatcaacc
1861 agtgtggcag cccctatcac cacttctgtt ccctcagtgg tctctggctt caccaccctg
1921 aagaccagct ccacaaaagg gatttggctt gaagaaacat ctgcagacac actcatcgga
1981 gaatccacag ctggcccaac cacccatcag tttgctgttc ccactgggat ttcaatgaca
2041 ggaggcagca gcaccagggg aagccagggc acaacccacc tactcaccag agccacagca
2101 tcatctgaga catccgcaga tttgactctg gccacgaacg gtgtcccagt ctccgtgtct
2161 ccagcagtga gcaagacggc tgctggctca agtcctccag gagggacaaa gccatcatat
2221 acaatggttt cttctgtcat ccctgagaca tcatctctac agtcctcagc tttcagggaa
2281 ggaaccagcc tgggactgac tccattaaac actagacatc ccttctcttc ccctgaacca
2341 gactctgcag gacacaccaa gataagcacc agcattcctc tgttgtcatc tgcttcagtt
2401 cttgaggata agtgtcagc gaccagcaca ttctcacacc acaaagccac ctcatctatt
2461 accacaggga ctcctgaaat ctcaacaaag acaaagccca gctcagccgt tctttcctcc
2521 atgaccctaa gcaatgcagc aacaagtcct gaaagagtca gaatgcaac ttcccctctg
2581 actcatccat ctccatcagg gaagagaca gcagggagtg tcctcactct cagcacctct
2641 gctgagacta cagactcacc taacatccac ccaactggga cactgacttc agaatcgtca
2701 gagagtccta gcactctcag cctcccaagt gtctctggag tcaaaaccac attttcttca
2761 tctactcctt ccactcatct atttactagt ggagaagaaa cagaggaaac ttcgaatcca
2821 tctgtgtctc aacctgagac ttctgttttcc agagtaagga ccaccttggc cagcacctct
2881 gtccctaccc cagtattccc caccatggac acctggccta cacgttcagc tcagttctct
2941 tcatcccacc tagtgagtga gctcagagct acgagcagta cctcagttac aaactcaact
3001 ggttcagctc ttcctaaaat atctcacctc actgggacgg caacaatgtc acagaccaat
3061 agagacacgt taatgactc tgctgcaccc caaagcacaa cttggccaga gactagtccc
3121 agattcaaga cagggttacc ttcagcaaca accactgttt caacctctgc cacttctctc
3181 tctgctactg taatggtctc taattcact tctccagcaa ctagttccat ggaagcaact
3241 tctatcaggg aaccatcaac aaccatcctc acaacagaga ccacgaatgg cccaggctct
3301 atggctgtgg cttctaccaa catcccaatt ggaaagggct acattactga aggaagattg
3361 gacacaagcc atctgcccat tggaaccaca gcttcctctg agacatctat ggatttttacc
```

Figure 3A

```
3421 atggccaaag aaagtgtctc aatgtcagta tctccatctc agtccatgga tgctgctggc
3481 tcaagcactc caggaaggac aagccaattc gttgacacat tttctgatga tgtctatcat
3541 ttaacatcca gagaaattac aatacctaga gatggaacaa gctcagctct gactccacaa
3601 atgactgcaa ctcaccctcc atctcctgat cctggctctg ctagaagcac ctggcttggc
3661 atcttgtcct catctccttc ttctcctact cccaaagtca caatgagctc cacattttca
3721 actcagagag tcaccacaag catgataatg gacacagttg aaactagtcg gtggaacatg
3781 cccaacttac cttccacgac ttccctgaca ccaagtaata ttccaacaag tggtgccata
3841 ggaaaaagca ccctggttcc cttggacact ccatctccag ccacatcatt ggaggcatca
3901 gaaggggac ttccaaccct cagcacctac cctgaatcaa caaacacacc cagcatccac
3961 ctcggagcac acgctagttc agaaagtcca agcaccatca aacttaccat ggcttcagta
4021 gtaaaacctg gctcttacac acctctcacc ttcccctcaa tagagaccca cattcatgta
4081 tcaacagcca gaatggctta ctcttctggg tcttcacctg agatgacagc tcctggagag
4141 actaacactg gtagtacctg ggaccccacc acctacatca ccactacgga tcctaaggat
4201 acaagttcag ctcaggtctc tacaccccac tcagtgagga cactcagaac cacagaaaac
4261 catccaaaga cagagtccgc cacccccagct gcttactctg gaagtcctaa aatctcaagt
4321 tcacccaatc tcaccagtcc ggccacaaaa gcatggacca tcacagacac aactgaacac
4381 tccactcaat tacattacac aaaattggca gaaaaatcat ctggatttga gacacagtca
4441 gctccaggac ctgtctctgt agtaatccct acctcccctc ccattggaag cagcacattg
4501 gaactaactt ctgatgtccc aggggaaccc ctggtccttg ctcccagtga gcagaccaca
4561 atcactctcc ccatggcaac atggctgagt accagtttga cagaggaaat ggcttcaaca
4621 gaccttgata tttcaagtcc aagttcaccc atgagtacat ttgctatttt tccacctatg
4681 tccacacctt ctcatgaact ttcaaagtca gaggcagata ccagtgccat tagaaataca
4741 gattcaacaa cgttggatca gcacctagga atcaggagtt tgggcagaac tggggactta
4801 acaactgttc ctatcacccc actgacaacc acgtggacca gtgtgattga acactcaaca
4861 caagcacagg acacccttc tgcaacgatg agtcctactc acgtgacaca gtcactcaaa
4921 gatcaaacat ctataccagc ctcagcatcc cttcccatc ttactgaagt ctaccctgag
4981 ctcgggacac aagggagaag ctcctctgag caaccactt tttggaaacc atctacagac
5041 acactgtcca gagagattga gactggccca acaaacattc aatccactcc acccatggac
5101 aacacaacaa cagggagcag tagtagtgga gtcaccctgg gcatagccca cttcccata
5161 ggaacatcct ccccagctga gacatccaca aacatggcac tggaaagaag aagttctaca
5221 gccactgtct ctatggctgg gacaatggga ctccttgtta ctagtgctcc aggaagaagc
5281 atcagccagt cattaggaag agtttcctct gtcctttctg agtcaactac tgaaggagtc
5341 acagattcta gtaaggaag cagcccaagg ctgaacacac agggaaatac agctctctcc
5401 tcctctcttg aacccagcta tgctgaagga agccagatga gcacaagcat ccctctaacc
5461 tcatctccta caactcctga tgtggaattc ataggggca gcacattttg gaccaaggag
5521 gtcaccacag ttatgaccct agacatctcc aagtcttcag caaggacaga gtccagctca
5581 gctaccctta tgtccacagc tttgggaagc actgaaaata caggaaaaga aaaactcaga
5641 actgcctcta tggatcttcc atctccaact ccatcaatgg aggtgacacc atggatttct
5701 ctcactctca gtaatgcccc caataccaca gattcacttg acctcagcca tggggtgcac
5761 accagctctg cagggacttt ggccactgac aggtcattga atactggtgt cactagagcc
5821 tccagattgg aaaacggctc tgataccttc tctaagtccc tgtctatggg aaacagcact
5881 cacacttcca tgactgacac agagaagagt gaagtgtctt cttcaatcca tccccgacct
5941 gagacctcag ctcctggagc agagaccact ttgacttcca ctcctggaaa cagggccata
6001 agcttaacat tgccttttc atccattcca gtgaagaag tcatttctac aggcataacc
6061 tcaggaccag acatcaactc agcacccatg acacattctc ccatcacccc accaacaatt
6121 gtatggacca gtacaggcac aattgaacag tccactcaac cactacatgc agtttcttca
6181 gaaaaagttt ctgtgcagac acagtcaact ccatatgtca actctgtggc agtgtctgct
6241 tcccctaccc atgagaattc agtctcttct ggaagcagca tcctctcc atattcctca
6301 gcctcacttg aatccttgga ttccacaatc agtaggagga tgcaatcac ttcctggcta
6361 tgggacctca ctacatctct ccccactaca acttggccaa gtactagttt atctgaggca
6421 ctgtcctcag gccattctgg ggtttcaaac ccaagttcaa ctacgactga atttccactc
6481 ttttcagctg catccacatc tgctgctaag caaagaaatc cagaaacaga gacccatggt
6541 ccccagaata cagccgcgag tactttgaac actgatgcat cctcggtcac aggtctttct
6601 gagactcctg tggggcaag tatcagctct gaagtccctc ttccaatggc cataacttct
6661 agatcagatg tttctggcct tacatctgag agtactgcta acccgagttt aggcacagcc
6721 tcttcagcag ggaccaaatt aactaggaca atatccctgc ccacttcaga gtctttggtt
6781 tccttagaa tgaacaagga tccatgacca gtgtcaatcc ctttgggtc ccatccaact
6841 actaatacag aaacaagcat cccagtaaac agcgcaggtc cacctggctt gtccacagta
6901 gcatcagatg taattgacac accttcagat ggggctgaga gtattcccac tgtctcctt
6961 tccccctccc ctgatactga agtgacaact atctcacatt cccagaaaaa gacaactcat
7021 tcatttagaa ccatttcatc tctcactcat gagttgactt caagagtgac acctattcct
7081 ggggattgga tgagttcagc tatgtctaca aagcccacag gagccagtcc ctccattaca
```

Figure 3A (continued)

```
 7141 ctgggagaga gaaggacaat caccctctgct gctccaacca cttcccccat agttctcact
 7201 gctagtttca cagagaccag cacagtttca ctggataatg aaactacagt aaaaacctca
 7261 gatatccttg acgcacggaa aacaaatgag ctcccctcag atagcagttc ttcttctgat
 7321 ctgatcaaca cctccatagc ttcttcaact atggatgtca ctaaaacagc ctccatcagt
 7381 cccactagca tctcaggaat gacagcaagt tcctccccat ctctcttctc ttcagataga
 7441 ccccaggttc ccacatctac aacagagaca aatacagcca cctctccatc tgtttccagt
 7501 aacacctatt ctcttgatgg gggctccaat gtgggtggca ctccatccac tttaccaccc
 7561 tttacaatca cccaccctgt cgagacaagc tcggccctat tagcctggtc tagaccagta
 7621 agaactttca gcaccatggt cagcactgac actgcctccg gagaaaatcc tacctctagc
 7681 aattctgtgg tgacttctgt tccagcacca ggtacatggg ccagtgtagg cagtactact
 7741 gacttacctg ccatgggctt tctcaagaca agtcctgcag gagaggcaca ctcacttcta
 7801 gcatcaacta ttgaaccagc cactgccttc actccccatc tctcagcagc agtggtcact
 7861 ggatccagtg ctacatcaga agccagtctt ctcactacga gtgaaagcaa agccattcat
 7921 tcttcaccac agaccccaac tacacccacc tctggagcaa actgggaaac ttcagctact
 7981 cctgagagcc ttttggtagt cactgagact tcagacacaa cacttacctc aaagattttg
 8041 gtcacagata ccatcttgtt ttcaactgtg tccacgccac cttctaaatt tccaagtacg
 8101 gggactctgt ctggagcttc cttccctact ttactcccgg acactccagc catccctctc
 8161 actgccactg agccaacaag ttcattagct acatcctttg attccacccc actggtgact
 8221 atagcttcgg atagtcttgg cacagtccca gagactaccc tgaccatgtc agagacctca
 8281 aatggtgatg cactggttct taagacagta agtaaccaga ataggagcat ccctggaatc
 8341 actatccaag gagtaacaga aagtccactc catccttctt ccacttcccc ctctaagatt
 8401 gttgctccac ggaatacaac ctatgaaggt tcgatcacag tggcactttc tactttgcct
 8461 gcgggaacta ctggttccct tgtattcagt cagagttctg aaaactcaga gacaacggct
 8521 ttggtagact catcagctgg gcttgagagg gcatctgtga tgccactaac cacaggaagc
 8581 cagggtatgg ctagctctgg aggaatcaga agtgggtcca ctcactcaac tggaaccaaa
 8641 acatttttctt ctctccctct gaccatgaac ccaggtgagg ttacagccat gtctgaaatc
 8701 accacgaaca gactgacagc tactcaatca acagcaccca aagggatacc tgtgaagccc
 8761 accagtgctg agtcaggcct cctaacacct gtctctgcct cctcaagccc atcaaaggcc
 8821 tttgcctcac tgactacagc tcccccatca acttggggga tcccacagtc taccttgaca
 8881 tttgagtttt ctgaggtccc aagtttggat actaagtccg cttctttacc aactcctgga
 8941 cagtccctga acaccattcc agactcagat gcaagcacag catcttcctc actgtccaag
 9001 tctccagaaa aaacccaagg gcaaggatg atgacttcca caaaggccat aagtgcaagc
 9061 tcatttcaat caacaggttt tactgaaacc cctgagggat ctgcctcccc ttctatggca
 9121 gggcatgaac ccagagtccc cacttcagga acaggggacc ctagatatgc ctcagagagc
 9181 atgtcttatc cagacccaag caaggcatca tcagctatga catcgacctc tcttgcatca
 9241 aaactcacaa ctctcttcag cacaggtcaa gcagcaaggt ctggttctag ttcctctccc
 9301 ataagcctat ccactgagaa agaaacaagc ttccttttccc ccactgcatc cacctccaga
 9361 aagacttcac tatttcttgg gccttccatg gcaaggcagc ccaacatatt ggtgcatctt
 9421 cagacttcag ctctgacact ttctccaaca tccactctaa atatgtccca ggaggagcct
 9481 cctgagttaa cctcaagcca gaccattgca gaagaagagg gaacaacagc tgaaacacag
 9541 acgttaacct tcacacatc tgagacccca acatccttgt tacctgtctc ttctcccaca
 9601 gaacccacag ccagaagaaa gagttctcca gaaacatggg caagctctat ttcagttcct
 9661 gccaagacct ccttggttga aacaactgat ggaacgctag tgaccaccat aaaagatgtca
 9721 agccaggcag cacaaggaaa ttccacgtgg cctgccccag cagaggagac ggggaccagt
 9781 ccagcaggca catccccagg aagcccagaa gtgtctacca ctctcaaaat catgagctcc
 9841 aaggaaccca gcatcagccc agagatcagg tccactgtgc gaaattctcc ttggaagact
 9901 ccagaaacaa ctgttcccat ggagaccaca gtggaaccag tcacccttca gtccacagcc
 9961 ctaggaagtg gcagcaccag catctctcac ctgcccacag aaccacatc accaaccaag
10021 tcaccaacag aaaatatgtt ggctacagaa agggtctccc tctcccatc cccacctgag
10081 gcttggacca acctttattc tggaactcca ggagggacca ggcagtcact ggccacaatg
10141 tcctctgtct cctagagtc accaactgct agaagcatca cagggactgg tcagcaaagc
10201 agtccagaac tggtttcaaa gacaactgga atgaattct ctatgtggca tggctctact
10261 ggagggacca caggggacac acatgtctct ctgagcacat cttccaatat ccttgaagac
10321 cctgtaacca gcccaaactc tgtgagctca ttgacagata atccaaaca taaaaccgag
10381 acatgggtaa gcaccacagc cattccctcc actgtcctga ataataagat aatggcagct
10441 gaacaacaga caagtcgatc tgtggatgag gcttattcat caactagttc ttggtcagat
10501 cagacatctg ggagtgacat cacccttggt gcatctcctg atgtcacaaa cacattatac
10561 atccctcca cagcacaaac cacctcacta gtgtctctgc cctctggaga ccaaggcatt
10621 acaagcctca ccaatccctc aggaggaaaa acaagctctg cgtcatctgt cacatctcct
10681 tcaataggc ttgagactct gagggccaat gtaagtgcag tgaaagtga cattgccct
10741 actgctgggc atctatctca gacttcatct cctgcggaag tgagcatcct ggacgtaacc
10801 acagctccta ctccaggtat ctccaccacc atcaccacca tgggaaccaa ctcaatctca
```

Figure 3A (continued)

```
10861 actaccacac ccaacccaga agtgggtatg agtaccatgg acagcacccc ggccacagag
10921 aggcgcacaa cttctacaga acacccttcc acctggtctt ccacagctgc atcagattcc
10981 tggactgtca cagacatgac ttcaaacttg aaagttgcaa gatctcctgg aacaatttcc
11041 acaatgcata caacttcatt cttagcctca agcactgaat tagactccat gtctactccc
11101 catggccgta taactgtcat tggaaccagc ctggtcactc catcctctga tgcttcagct
11161 gtaaagacag agaccagtac aagtgaaaga acattgagtc cttcagacac aactgcatct
11221 actcccatct caacttttc tcgtgtccag aggatgagca tctcagttcc tgacattta
11281 agtacaagtt ggactcccag tagtacagaa gcagaagatg tgcctgtttc aatggtttct
11341 acagatcatg ctagtacaaa gactgaccca aatacgcccc tgtccacttt tctgtttgat
11401 tctctgtcca ctcttgactg ggacactggg agatctctgt catcagccac agccactacc
11461 tcagctcctc aggggccac aactcccag gaactcactt tggaaaccat gatcagccca
11521 gctacctcac agttgccctt ctctataggg cacattacaa gtgcagtcac accagctgca
11581 atggcaagga gctctggagt tacttttca agaccagatc ccacaagcaa aaaggcagag
11641 cagacttcca ctcagcttcc caccaccact tctgcacatc cagggcaggt gcccagatca
11701 gcagcaacaa ctctggatgt gatcccacac acagcaaaaa ctccagatgc aactttcag
11761 agacaagggc agacagctct tacaacagag gcaagagcta catctgactc ctggaatgag
11821 aaagaaaaat caacccccaag tgcaccttgg atcactgaga tgatgaattc tgtctcagaa
11881 gataccatca aggaggttac cagctcctcc agtgtattaa aggaccctga atacgctgga
11941 cataaacttg gaatctggga cgacttcatc cccaagtttg gaaaagcagc ccatatgaga
12001 gagttgcccc ttctgagtcc accacaggac aaagaggcaa ttcaccttc tacaaacaca
12061 gtagagacca caggctgggt cacaagttcc gaacatgctt ctcattccac tatcccagcc
12121 cactcagcgt catccaaact cacatctcca gtggttacaa cctccaccag ggaacaagca
12181 atagtttcta tgtcaacaac cacatggcca gagtctacaa gggctagaac agagcctaat
12241 tccttcttga ctattgaact gagggacgtc agcccttaca tggacaccag ctcaaccaca
12301 caaacaagta ttatctcttc cccaggttcc actgcgatca ccaaggggcc tagaacagaa
12361 attacctcct ctaagagaca tccagctca ttccttgccc agtctatgag gtcgtcgagac
12421 agcccctcag aagccatcac caggctgtct aactttcctg ccatgacaga atctggagga
12481 atgatccttg ctatgcaaac aagtccacct ggcgctacat cactaagtgc acctactttg
12541 gatacatcag ccacagcctc ctggacaggg actccactgg ctacgactca gagatttaca
12601 tactcagaga agaccactct ctttagcaaa ggtcctgagg atacatcaca gccaagccct
12661 ccctctgtgg aagaaaccag ctcttcctct tccctggtac ctatccatgc tacaacctcg
12721 ccttccaata ttttgttgac atcacaaggg cacagtccct cctctactcc acctgtgacc
12781 tcagttttct tgtctgagac ctctggcctg gggaagacca cagacatgtc gaggataagc
12841 ttggaacctg gcacaagttt acctcccaat ttgagcagta cagcaggtga ggcgttatcc
12901 acttatgaag cctccagaga tacaaaggca attcatcatt ctgcagacac agcagtgacg
12961 aatatggagg caaccagttc tgaatattct cctatcccag gccatacaaa gccatccaaa
13021 gccacatctc cattggttac ctcccacatc atgggggaca tcacttcttc cacatcagta
13081 tttggctcct ccgagaccac agagattgag acagtgtcct ctgtgaacca gggacttcag
13141 gagagaagca catcccaggt ggccagctct gctacagaga caagcactgt cattacccat
13201 gtgtctagtg gtgatgctac tactcatgtc accaagacac aagccacttt ctctagcgga
13261 acatccatct caagccctca tcagtttata acttctacca acacatttac agatgtgagc
13321 accaaccct ccacctctct gataatgaca gaatcttcag gagtgaccat caccacccaa
13381 acaggtccta ctggagctgc aacacagggt ccatatctct tggacacatc aaccatgcct
13441 tacttgacag agactccatt agctgtgact ccagatttta tgcaatcaga gaagaccact
13501 ctcataagca aggtcccaa ggatgtgacc tggacaagcc ctccctctgt ggcagaaacc
13561 agctatccct cttccctgac acctttcttg gtcacaacca tacctcctgc cacttccacg
13621 ttacaagggc aacatacatc ctctcctgtt tctgcgactt cagttcttac ctctggactg
13681 gtgaagacca cagatatgtt gaacacaagc atgaacctg tgaccaattc acctcaaaat
13741 ttgaacaatc catcaaatga gatactgctc acttttggcag ccaccacaga tatagagact
13801 attcatcctt ccataaacaa agcagtgacc aatatgggga ctgccagttc agcacatgta
13861 ctgcattcca ctctcccagt cagctcagaa ccatctacag ccacatctcc aatggttcct
13921 gcctccagca tggggacgc tcttgcttct atatcaatac ctggttctga gaccacagac
13981 attgagggag agccaacatc ctccctgact gctggacgaa aagagaacag caccctccag
14041 gagatgaact caactacaga gtcaaacatc atcctctcca atgtgtctgt gggggctatt
14101 actgaagcca caaaaatgga agtcccctct tttgatgcaa cattcatacc aactcctgct
14161 cagtcaacaa agttcccaga tattttctca gtagccagca gtagactttc aaactctcct
14221 cccatgacaa tatctaccca catgaccacc acccagacag ggtcttctgg agctacatca
14281 aagattccac ttgccttaga cacatcaacc ttggaaacct cagcagggac tccatcagtg
14341 gtgactgagg ggtttgccca ctcaaaaata accactgcaa tgaacaatga tgtcaaggac
14401 gtgtcacaga caaaccctcc ctttcaggat gaagccagct ctccctcttc tcaagcacct
14461 gtccttgtca caaccttacc ttcttctgtt gctttcacac cgcaatggca cagtacctcc
14521 tctcctgttt ctatgtcctc agttcttact tcttcactgg taaagaccgc aggcaaggtg
14581 gatacaagct tagaaacagt gaccagttca cctcaaagta tgagcaacac tttggatgac
14641 atatcggtca cttcagcagc caccacagat atagagacaa cgcatccttc cataaacaca
```

Figure 3A (continued)

```
14701 gtagttacca atgtggggac caccggttca gcatttgaat cacattctac tgtctcagct
14761 tacccagagc catctaaagt cacatctcca aatgttacca cctccaccat ggaagacacc
14821 acaatttccc gatcaatacc taaatcctct aagactacaa gaactgagac tgagacaact
14881 tcctccctga ctcctaaact gagggagacc agcatctccc aggagatcac ctcgtccaca
14941 gagacaagca ctgttcctta caaagagctc actggtgcca ctaccgaggt atccaggaca
15001 gatgtcactt cctctagcag tacatccttc cctggccctg atcagtccac agtgtcacta
15061 gacatctcca cagaaaccaa caccaggctg tctacctccc caataatgac agaatctgca
15121 gaaataacca tcaccaccca aacaggtcct catggggcta catcacagga tacttttacc
15181 atggacccat caaatacaac cccccaggca gggatccact cagctatgac tcatggattt
15241 tcacaattgg atgtgaccac tcttatgagc agaattccac aggatgtatc atggacaagt
15301 cctccctctg tggataaaac cagctccccc tcttcctttc tgtcctcacc tgcaatgacc
15361 acaccttccc tgatttcttc taccttacca gaggataagc tctcctctcc tatgacttca
15421 cttctcacct ctggcctagt gaagattaca gacatattac gtacacgctt ggaacctgtg
15481 accagctcac ttccaaattt cagcagcacc tcagataaga tactggccac ttctaaagac
15541 agtaaagaca caaaggaaat ttttccttct ataaacacag aagagaccaa tgtgaaagcc
15601 aacaactctg gacatgaatc ccattcccct gcactggctg actcagagac acccaaagcc
15661 acaactcaaa tggttatcac caccactgtg ggagatccag ctccttccac atcaatgcca
15721 gtgcatggtt cctctgagac tacaaacatt aagagagagc aacatatttt cttgactcct
15781 agactgagag agaccagtac ctctcaggag tccagctttc ccacggacac aagttttcta
15841 ctttccaaag tccccactgg tactattact gaggtctcca gtacagggt caactcttct
15901 agcaaaattt ccaccccaga ccatgataag tccacagtgc cacctgacac cttcacagga
15961 gagatcccca gggtcttcac ctcctctatt aagacaaaat ctgcagaaat gacgatcacc
16021 acccaagcaa gtcctcctga gtctgcatcg cacagtaccc ttcccttgga cacatcaacc
16081 acactttccc agggagggac tcattcaact gtgactcagg gattcccata ctcagaggtg
16141 accactctca tgggcatggg tcctgggaat gtgtcatgga tgacaactcc ccctgtggaa
16201 gaaaccagct ctgtgtcttc cctgatgtct tcacctgcca tgcatcccc ttctcctgtt
16261 tcctccacat caccacagag catcccctcc tctcctcttc ctgtgactgc acttcctact
16321 tctgttctgg tgacaaccac agatgtgttg ggcacaacaa gcccagagtc tgtaaccagt
16381 tcacctccaa atttgagcag catcactcat gagagaccgg ccacttacaa agacactgca
16441 cacacagaag ccgccatgca tcattccaca aacaccgcag tgaccaatgt agggacttcc
16501 gggtctggac ataaatcaca atcctctgtc ctagctgact cagagacatc gaaagccaca
16561 cctctgatga gtaccacctc caccctgggg gacacaagtg tttccacatc aactcctaat
16621 atctctcaga ctaaccaaat tcaaacagag ccaacagcat ccctgagccc tagactgagg
16681 gagagcagca cgtctgagaa gaccagctca acaacagaga caaatactgc cttttcttat
16741 gtgcccacag gtgctattac tcaggcctcc agaacagaaa tctcctctag cagaacatcc
16801 atctcagacc ttgatcggcc cacaatagca cccgacatct ccacaggaat gatcaccagg
16861 ctcttcacct cccccatcat gacaaaatct gcagaaatga ccgtcaccac tcaaacaact
16921 actcctgggg ctacatcaca gggtatcctt ccttgggaca catcaaccac acttttccag
16981 ggagggactc attcaaccgt gtctcaggga ttcccacact cagagataac cactcttcgg
17041 agcagaaccc ctggagatgt gtcatggatg acaactcccc ctgtggaaga accagctct
17101 gggttttccc tgatgtcacc ttccatgaca tccccttctc ctgtttcctc cacatcacca
17161 gagagcatcc cctcctctcc tctccctgtg actgcacttc ttacttctgt tctggtgaca
17221 accaccaatg tattgggcac aacaagccca gagaccgtaa cgagttcacc tccaaattta
17281 agcagcccca cacaggagag actgaccact acaaagaca ctgcgcacac agaagccatg
17341 catgcttcca tgcatacaaa cactgcagtg ccaacgtcg ggacctccat ttctggacat
17401 gaatcacaat cttctgtccc agctgattca cacacatcca agccacatc tccaatgggt
17461 atcaccttcg ccatggggga tacaagtgtt tctacatcaa ctcctgcctt ctttgagact
17521 agaattcaga ctgaatcaac atcctctttg attcctggat taagggacac caggacgtct
17581 gaggagatca acactgtgac agagaccagc actgtccttt cagaagtgcc cactactact
17641 actactgagg tctccaggac agaagttatc acttccagca gaacaaccat ctcagggcct
17701 gatcattcca aaatgtcacc ctacatctcc acagaaacca tcaccaggct ctccactttt
17761 cctttttgtaa caggatccac agaaatggcc atcaccaacc aaacaggtcc tagggact
17821 atctcacagg ctacccttac cctggacaca tcaagcacag cttcctggga agggactcac
17881 tcacctgtga ctcagagatt tccacactca gaggagacca ctactatgag cagaagtact
17941 aagggcgtgt catggcaaag ccctccctct gtggaagaaa ccagttctcc ttcttcccca
18001 gtgcctttac ctgcaataac ctcacattca tctctttatt ccgcagtatc aggaagtagc
18061 cccacttctg ctctccctgt gacttccctt ctcacctctg gcaggaggaa gaccatagac
18121 atgttggaca cacactcaga acttgtgacc agctccttac caagtgcaag tagcttctca
18181 ggtgagatac tcacttctga agcctccaca aatacagaga caattcactt ttcagagaac
18241 acagcagaaa ccaatatggg gaccaccaat tctatgcata aactacattc ctctgtctca
```

Figure 3A (continued)

```
18301 atccactccc agccatccgg acacacacct ccaaaggtta ctggatctat gatggaggac
18361 gctattgttt ccacatcaac acctggttct cctgagacta aaaatgttga cagagactca
18421 acatcccctc tgactcctga actgaaagag acagcaccg ccctggtgat gaactcaact
18481 acagagtcaa acactgtttt ctccagtgtg tccctggatg ctgctactga ggtctccagg
18541 gcagaagtca cctactatga tcctacattc atgccagctt ctgctcagtc aacaaagtcc
18601 ccagacattt cacctgaagc cagcagcagt cattctaact ctcctccctt gacaatatct
18661 acacacaaga ccatcgccac acaaacaggt ccttctgggg tgacatctct tggccaactg
18721 accctggaca catcaaccat agccacctca gcaggaactc catcagccag aactcaggat
18781 tttgtagatt cagaaacaac cagtgtcatg aacaatgatc tcaatgatgt gttgaagaca
18841 agcccttct ctgcagaaga agccaactct ctctcttctc aggcacctct ccttgtgaca
18901 acctcacctt ctcctgtaac ttccacattg caagagcaca gtacctcctc tcttgtttct
18961 gtgacctcag tacccacccc tacactggcg aagatcacag acatggacac aaacttagaa
19021 cctgtgactc gttcacctca aaatttaagg aacaccttgg ccacttcaga agccaccaca
19081 gatacacaca caatgcatcc ttctataaac acagcaatgg ccaatgtggg gaccaccagt
19141 tcaccaaatg aattctattt tactgtctca cctgactcag acccatataa agccacatcc
19201 gcagtagtta tcacttccac ctcgggggac tcaatagttt ccacatcaat gcctagatcc
19261 tctgcgatga aaaagattga gtctgagaca actttctccc tgatatttag actgagggag
19321 actagcacct cccagaaaat tggctcatcc tcagacacaa gcacggtctt tgacaaagca
19381 ttcactgctg ctactactga ggtctccaga acagaactca cctcctctag cagaacatcc
19441 atccaaggca ctgaaaagcc cacaatgtca ccggacacct ccacaagatc tgtcaccatg
19501 ctttctactt tgctggcct gacaaaatcc gaagaaagga ccattgccac ccaaacaggt
19561 cctcataggg cgacatcaca gggtacccctt acctgggaca catcaatcac aacctcacag
19621 gcagggaccc actcagctat gactcatgga ttttcacaat tagatttgtc cactcttacg
19681 agtagagttc ctgagtacat atcagggaca agcccaccct ctgtggaaaa aaccagctct
19741 tcctcttccc ttctgtcttt accagcaata acctcaccgt ccctgtacc tactacatta
19801 ccagaaagta ggccgtcttc tcctgttcat ctgacttcac tccccacctc tggcctagtg
19861 aagaccacag atatgctggc atctgtggcc agtttacctc caaacttggg cagcacctca
19921 cataagatac cgactacttc agaagacatt aaagatacag agaaaatgta tccttccaca
19981 aacatagcag taaccaatgt ggggaccacc acttctgaaa aggaatctta ttcgtctgtc
20041 ccagcctact cagaaccacc caaagtcacc tctccaatgg ttacctcttt caacataagg
20101 gacaccattg tttccacatc catgcctggc tcctctgaga ttacaaggat tgagatggag
20161 tcaacattct ccgtggctca tgggctgaag ggaaccagca cctcccagga ccccatcgta
20221 tccacagaga aaagtgctgt ccttcacaag ttgaccactg gtgctactga gacctctagg
20281 acagaagttg cctcttctag aagaacatcc attccaggcc ctgatcattc cacagagtca
20341 ccagacatct ccactgaagt gatccccagc ctgcctatct cccttggcat tacagaatct
20401 tcaaatatga ccatcatcac tcgaacaggt cctcctcttg gtctacatc acagggcaca
20461 tttaccttgg acacaccaaac tacatcctcc agggcaggaa cacactcgat ggcgactcag
20521 gaatttccac actcagaaat gaccactgtc atgaacaagg accctgagat tctatcatgg
20581 acaatccctc cttctataga gaaaaccagc ttctcctctt ccctgatgcc ttcaccagcc
20641 atgacttcac ctcctgtttc ctcaacatta ccaaagacca ttcacaccac tccttctcct
20701 atgacctcac tgctcacccc tagcctagtg atgaccacag acacattggg cacaagccca
20761 gaacctacaa ccagttcacc tccaaatttg agcagtacct cacatgtgat actgacaaca
20821 gatgaagaca ccacagctat agaagccatg catccttcca caagcacagc agcgactaat
20881 gtggaaacca cctgttctgg acatgggtca caatcctctg tcctaactga ctcagaaaaa
20941 accaaggcca cagctccaat ggataccacc tccaccatgg ggcatacaac tgtttccaca
21001 tcaatgtctg tttcctctga gactacaaaa attaagagag agtcaacata ttccttgact
21061 cctggactga gagagaccag catttcccaa aatgccagct tttccactga cacaagtatt
21121 gttctttcag aagtccccac tggtactact gctgaggtct ccaggacaga agtcacctcc
21181 tctggtagaa catccatccc tggcccttct cagtccacag ttttgccaga aatatccaca
21241 agaacaatga caaggctctt tgcctcgccc accatgacag aatcagcaga aatgaccatc
21301 cccactcaaa caggtccttc tgggtctacc tcacaggata cccttacctt ggacacatcc
21361 accacaaagt cccaggcaaa gactcattca actttgactc agagatttcc acactcagag
21421 atgaccactc tcatgagcag aggtcctgga gatatgtcat ggcaaagctc tccctctctg
21481 gaaaatccca gctctctccc ttccctgctg tctttacctg ccacaacctc acctcctccc
21541 atttcctcca cattaccagt gactatctcc tcctctcctc ttcctgtgac ttcacttctc
21601 acctctagcc cggtaacgac cacagacatg ttacacacaa gcccagaact tgtaaccagt
21661 tcacctccaa agctgagcca cacttcagat gagagactga ccactggcaa ggacaccaca
21721 aatacagaag ctgtgcatcc ttccacaaac acagcagcgt ccaatgtgga gattcccagc
21781 tttggacatg aatccccttc ctctgcctta gctgactcag agacatccaa agccacatca
21841 ccaatgttta ttacctccac ccaggaggat acaactgttg ccatatcaac ccctcacttc
21901 ttggagacta gcagaattca gaaagagtca atttcctccc tgagccctaa attgagggag
21961 acaggcagtt ctgtggagac aagctcagcc atagagacaa gtgctgtcct ttctgaagtg
22021 tccattggtg ctactactga gatctccagg acagaagtca cctcctctag cagaacatcc
22081 atctctggtt ctgctgagtc cacaatgttg ccagaaatat ccaccacaag aaaaatcatt
```

Figure 3A (continued)

```
22141 aagttcccta cttcccccat cctggcagaa tcatcagaaa tgaccatcaa gacccaaaca
22201 agtcctcctg ggtctacatc agagagtacc tttacattag acacatcaac cactccctcc
22261 ttggtaataa cccattcgac tatgactcag agattgccac actcagagat aaccactctt
22321 gtgagtagag gtgctgggga tgtgccacgg cccagctctc tccctgtgga agaaacaagc
22381 cctccatctt cccagctgtc tttatctgcc atgatctcac cttctcctgt ttcttccaca
22441 ttaccagcaa gtagccactc ctcttctgct tctgtgactt cacctctcac accaggccaa
22501 gtgaagacta ctgaggtgtt ggacgcaagt gcagaacctg aaaccagttc acctccaagt
22561 ttgagcagca cctcagttga aatactggcc acctctgaag tcaccacaga tacggagaaa
22621 attcatcctt tcccaaacac ggcagtaacc aaagttggaa cttccagttc tggacatgaa
22681 tccccttcct ctgtcctacc tgactcagag acaaccaaag ccacatcggc aatgggtacc
22741 atctccatta tgggggatac aagtgtttct acattaactc ctgccttatc taacactagg
22801 aaaattcagt cagagccagc ttcctcactg accaccagat tgagggagac cagcacctct
22861 gaagagacca gcttagccac agaagcaaac actgttcttt ctaaagtgtc cactggtgct
22921 actactgagg tctccaggac agaagccatc tcctttagca gaacatccat gtcaggccct
22981 gagcagtcca caatgtcaca agacatctcc ataggaacca tccccaggat ttctgcctcc
23041 tctgtcctga cagaatctgc aaaaatgacc atcacaaccc aaacaggtcc ttcggagtct
23101 acactagaaa gtaccttaa tttgaacaca gcaaccacac cctcttgggt ggaaacccac
23161 tctatagtaa ttcagggatt tccacaccca gagatgacca cttccatggg cagaggtcct
23221 ggaggtgtgt catggcctag ccctcccttt gtgaaagaaa ccagccctcc atcctcccg
23281 ctgtctttac ctgccgtgac ctcacctcat cctgtttcca ccacattcct agcacatatc
23341 cccccctc cccttcctgt gacttcactt ctcacctctg gcccggcgac aaccacagat
23401 atcttgggta caagcacaga acctggaacc agttcatctt caagtttgag caccacctcc
23461 catgagagac tgaccactta caaagacact gcacatacag aagccgtgca tccttccaca
23521 aacacaggag ggaccaatgt ggcaaccacc agctctggat ataaatcaca gtcctctgtc
23581 ctagctgact catctccaat gtgtaccacc tccaccatgg gggatacaag tgttctcaca
23641 tcaactcctg ccttccttga gactaggagg attcagacag agctagcttc ctccctgacc
23701 cctggattga gggagtccag tggctctgaa gggaccagct caggcaccaa gatgagcact
23761 gtcctctcta aagtgcccac tggtgctact actgagatct ccaaggaaga cgtcacctcc
23821 atcccaggtc ccgctcaatc cacaatatca ccagacatct ccacaagaac cgtcagctgg
23881 ttctctacat cccctgtcat gacagaatca gcagaaataa ccatgaacac ccatacaagt
23941 ccttagggg ccacaacaca aggcaccagt actttggcca cgtcaagcac aacctctttg
24001 acaatgacac actcaactat atctcaagga ttttcacact cacagatgag cactcttatg
24061 aggaggggtc ctgaggatgt atcatggatg agccctcccc ttctggaaaa aactagacct
24121 tccttttctc tgatgtcttc accagccaca acttcacctt ctcctgtttc ctccacatta
24181 ccagagagca tctcttcctc tcctcttcct gtgacttcac tcctcacgtc tggcttggca
24241 aaaactacag atatgttgca caaaagctca gaacctgtaa ccaactcacc tgcaaatttg
24301 agcagcacct cagttgaaat actggccacc tctgaagtca ccacagatac agagaaaact
24361 catccttctt caaacagaac agtgaccgat gtgggggacct ccagttctgg acatgaatcc
24421 acttcctttg tcctagctga ctcacagaca tccaaagtca catctccaat ggttattacc
24481 tccaccatgg aggatacgag tgtctccaca tcaactcctg gcttttttga gactagcaga
24541 attcagacag aaccaacatc ctccctgacc cttggactga aaagaccag cagctctgag
24601 gggaccagct tagccacaga gatgagcact gtcctttctg gagtgcccac tggtgccact
24661 gctgaagtct ccaggacaga agtcacctcc tctagcagaa catccatctc aggctttgct
24721 cagctcacag tgtcaccaga gacttccaca gaaaccatca ccagactccc tacctccagc
24781 ataatgacag aatcagcaga aatgatgatc aagacacaaa cagatcctcc tgggtctaca
24841 ccagagagta ctcatactgt ggacatatca acaaccccca actgggtaga aacccactcg
24901 actgtgactc agagattttc acactcagag atgaccactc ttgtgagcag aagccctggt
24961 gatatgttat ggcctagtca atcctctgtg gaagaaacca gctctgcctc ttccctgctg
25021 tctctgcctg ccacgacctc accttctcct gtttcctcta cattagtaga ggatttccct
25081 tccgcttctc ttcctgtgac ttctcttctc accctggcc tggtgataac cacagacagg
25141 atgggcataa gcagagaacc tggaaccagt tccacttcaa atttgagcag cacctcccat
25201 gagagactga ccactttgga agacactgta gatacagaag acatgcagcc ttccacacac
25261 acagcagtga ccaacgtgag gacctccatt tctggacatg aatcacaatc ttctgtccta
25321 tctgactcag agacacccaa agccacatct ccaatgggta ccacctacac catggggaa
25381 acgagtgttt ccatatccac ttctgacttc tttgagacca gcagaattca gatagaacca
25441 acatcctccc tgacttctgg attgagggag accagcagct ctgagaggat cagctcagcc
25501 acagagggaa gcactgtcct ttctgaagtg cccagtggtg ctaccactga ggtctccagg
25561 acagaagtga tatcctctag gggaacatcc atgtcagggc ctgatcagtt caccatatca
25621 ccagacatct ctactgaagc gatcaccagg ctttctactt cccccattat gacagaatca
25681 gcagaaagtg ccatcactat tgagacaggt tctcctgggg ctacatcaga gggtaccctc
25741 accttggaca cctcaacaac aacctttttgg tcagggaccc actcaactgc atctccagga
25801 ttttcacact cagagtgac cactcttatg agtagaactc tggagatgt gccatggccg
25861 agccttccct ctgtggaaga agccagctct gtctcttcct cactgcttc acctgccatg
25921 acctcaactt cttttttctc cgcattacca gagagcatct cctcctctcc tcatcctgtg
25981 actgcacttc tcacccttgg cccagtgaag accacagaca tgttgcgcac aagctcagaa
```

Figure 3A (continued)

```
26041 cctgaaacca gttcacctcc aaatttgagc agcacctcag ctgaaatatt agccacgtct
26101 gaagtcacca aagatagaga gaaaattcat ccctcctcaa acacacctgt agtcaatgta
26161 gggactgtga tttataaaca tctatcccct tcctctgttt tggctgactt agtgacaaca
26221 aaacccacat ctccaatggc taccacctcc actctgggga atacaagtgt ttccacatca
26281 actcctgcct tcccagaaac tatgatgaca cagccaactt cctccctgac ttctggatta
26341 agggagatca gtacctctca agagaccagc tcagcaacag agagaagtgc ttctctttct
26401 ggaatgccca ctggtgctac tactaaggtc tccagaacag aagccctctc cttaggcaga
26461 acatccaccc caggtcctgc tcaatccaca atatcaccag aaatctccac ggaaaccatc
26521 actagaattt ctactcccct caccacgaca ggatcagcag aaatgaccat cacccccaaa
26581 acaggtcatt ctggggcatc ctcacaaggt acctttacct tggacacatc aagcagagcc
26641 tcctggccag gaactcactc agctgcaact cacagatctc cacactcagg gatgaccact
26701 cctatgagca gaggtcctga ggatgtgtca tggccaagcc gcccatcagt ggaaaaaact
26761 agccctccat cttccctggt gtcttatct gcagtaacct caccttcgcc actttattcc
26821 acaccatctg agagtagcca ctcatctcct ctcgggtga cttctctttt caccctgtc
26881 atgatgaaga ccacagacat gttggacaca agcttggaac ctgtgaccac ttcacctccc
26941 agtatgaata tcacctcaga tgagagtctg gccacttcta aagccaccat ggagacagag
27001 gcaattcaga ttttcagaaaa cacagctgtg actcagatgg gcaccatcag cgctagacaa
27061 gaattctatt cctcttatcc aggcctccca gagccatcca aagtgacatc tccagtggtc
27121 acctcttcca ccataaaaga cattgttttct acaaccatac ctgcttcctc tgagataaca
27181 agaattgaga tggagtcaac atccaccctg accccacac caagggagac cagcacctcc
27241 caggagatcc actcagccac aaagccaagc actgttcctt acaaggcact cactagtgcc
27301 acgattgagg actccatgac acaagtcatg tcctctagca gaggacctag ccctgatcag
27361 tccacaatgt cacaagacat atccagtgaa gtgatcacca ggctctctac ctcccccatc
27421 aagcagaat ctacagaaat gaccattacc acccaaacag gttctcctgg ggctacatca
27481 aggggtaccc ttaccttgga cacttcaaca acttttatgt cagggaccca ctcaactgca
27541 tctcaaggat tttcacactc acagatgacc gctcttatga gtagaactcc tggagatgtg
27601 ccatggctaa gccatccctc tgtggaagaa gccagctctg cctcttttct actgtcttca
27661 cctgtcatga cctcatcttc tcccgttct tccacattac cagacagcat ccactcttct
27721 tcgcttcctg tgacatcact tctcacctca gggctggtga agaccacaga gctgttgggc
27781 acaagctcag aacctgaaac cagttcaccc ccaaatttga gcagcacctc agctgaaata
27841 ctggccacca ctgaagtcac tacagataca gagaaactgg agatgaccaa tgtggtaacc
27901 tcaggttata cacatgaatc tccttcctct gtcctagctg actcagtgac aacaaaggcc
27961 acatcttcaa tgggtatcac ctaccccaca ggagatacaa atgttctcac atcaaccct
28021 gccttctctg acaccagtag gattcaaaca aagtcaaagc tctcactgac tcctgggttg
28081 atggagacca gcatctctga agagaccagc tctgccacag aaaaaagcac tgtcctttct
28141 agtgtgccca ctggtgctac tactgaggtc tccaggacag aagccatctc ttctagcaga
28201 acatccatcc caggccctgc tcaatccaca atgtcatcag acacctccat ggaaaccatc
28261 actagaattt ctacccccct cacaaggaaa gaatcaacag acatggccat cacccccaaa
28321 acaggtcctt ctggggctac ctcgcagggt acctttacct tggactcatc aagcacagcc
28381 tcctggccag gaactcactc agctacaact cagagatttc cacagtcagt ggtgacaact
28441 cctatgagca gaggtcctga ggatgtgtca tggccaagcc gctgtctgt ggaaaaaaac
28501 agccctccat cttccctggt atcttcatct tcagtaacct caccttcgcc actttattcc
28561 acaccatctg ggagtagcca ctcctctcct gtccctgtca cttctctttt cacctctatc
28621 atgatgaagg ccacagacat gttggatgca agtttggaac ctgagaccac ttcagctccc
28681 aatatgaata tcacctcaga tgagagtctg gccacttcta aagccaccac ggagacagag
28741 gcaattcacg tttttgaaaa tacagcagcg tcccatgtgg aaaccaccag tgctacagag
28801 gaactctatt cctcttcccc aggcttctca gagccaacaa aagtgatatc tccagtggtc
28861 acctcttcct ctataagaga caacatggtt tccacaacaa tgcctggctc ctctggcatt
28921 acaaggattg agatagagtc aatgtcatct ctgaccccg gactgaggga gaccagaacc
28981 tcccaggaca tcacctcatc cacagagaca agcactgtcc tttacaagat gtcctctggt
29041 gccactcctg aggtctccag gacagaagtt atgcccctca gcagaacatc cattcctggc
29101 cctgctcagt ccacaatgtc actagacatc tccgatgaag ttgtcaccag gctgtctacc
29161 tctcccatca tgacagaatc tgcagaaata accatcacca cccaaacagg ttattctctg
29221 gctacatccc aggttaccct tcccttgggc acctcaatga cttttttgtc agggacccac
29281 tcaactatgt ctcaaggact ttcacactca gagatgacca atcttatgag caggggtcct
29341 gaaagtctgt catggacgag ccctcgcttt gtggaaacaa ctagatcttc ctcttctctg
29401 acatcattac ctctcacgac ctcactttct cctgtgtcct ccacattact agacagtagc
29461 cctcctctc ctcttcctgt gacttcactt atcctcccag gcctggtgaa gactacagaa
29521 gtgttggata caagctcaga gcctaaaacc agttcatctc caaatttgag cagcacctca
29581 gttgaaatac cggcccctc tgaaatcatg acagatacag agaaaattca tccttcctca
29641 aacacagcgg tggccaaagt gaggacctcc agttctgttc atgaatctca ttcctctgtc
29701 ctagctgact cagaaacaac cataaccata ccttcaatga gtatcacctc cgctgtggac
29761 gataccactg ttttcacatc aaatcctgcc ttctctgaga ctaggaggat tccgacagag
29821 ccaacattct cattgactcc tggattcagg gagactagca cctctgaaga gaccaccta
29881 atcacagaaa caagtgcagt cctttatgga gtgcccacta gtgctactac tgaagtctcc
```

```
29941 atgacagaaa tcatgtcctc taatagaaca cacatccctg actctgatca gtccacgatg
30001 tctccagaca tcatcactga agtgatcacc aggctctctt cctcatccat gatgtcagaa
30061 tcaacacaaa tgaccatcac cacccaaaaa agttctcctg gggctacagc acagagtact
30121 cttaccttgg ccacaacaac agccccttg gcaaggaccc actcaactgt tcctcctaga
30181 tttttacact cagagatgac aactcttatg agtaggagtc ctgaaaatcc atcatggaag
30241 agctctccct ttgtggaaaa aactagctct tcatcttctc tgttgtcctt acctgtcacg
30301 acctcacctt ctgtttcttc cacattaccg cagagtatcc cttcctcctc tttttctgtg
30361 acttcactcc tcaccccagg catggtgaag actacagaca caagcacaga acctggaacc
30421 agtttatctc caaatctgag tggcacctca gttgaaatac tggctgcctc tgaagtcacc
30481 acagatacag agaaaattca tccttcttca agcatggcag tgaccaatgt gggaaccacc
30541 agttctggac atgaactata ttcctctgtt tcaatccact cggagccatc caaggctaca
30601 tacccagtgg gtactccctc ttccatggct gaaacctcta tttccacatc aatgcctgct
30661 aattttgaga ccacaggatt tgaggctgag ccatttctc atttgacttc tggatttagg
30721 aagacaaaca tgtccctgga caccagctca gtcacaccaa caaatacacc ttcttctcct
30781 gggtccactc acctttaca gagttccaag actgatttca cctcttctgc aaaaacatca
30841 tccccagact ggcctccagc ctcacagtat actgaaattc agtggacat aatcaccccc
30901 tttaatgctt ctccatctat tacggagtcc actgggataa cctccttccc agaatccagg
30961 tttactatgt ctgtaacaga aagtactcat catctgagta cagatttgct gccttcagct
31021 gagactattt ccactggcac agtgatgcct tctctatcag aggccatgac ttcatttgcc
31081 accactggag ttccacgagc catctcaggt tcaggtagtc cattctctag gacagagtca
31141 ggccctgggg atgctactct gtccaccatt gcagagagcc tgccttcatc cactcctgtg
31201 ccattctcct cttcaacctt cactaccact gattcttcaa ccatcccagc cctccatgag
31261 ataacttcct cttcagctac cccatataga gtggacacca gtcttgggac agagagcagc
31321 actactgaag gacgcttggt tatggtcagt actttggaca cttcaagcca accaggcagg
31381 acatcttcaa cacccatttt ggataccaga atgacagaga gcgttgagct gggaacagtg
31441 acaagtgctt atcaagttcc ttcactctca acacgttga caagaactga tggcattatg
31501 gaacacatca caaaaatacc caatgaagca gcacacagag gtaccataag accagtcaaa
31561 ggccctcaga catccacttc gcctgccagt cctaaaggac tacacacagg agggacaaaa
31621 agaatggaga ccaccaccac agctttgaag accaccacca cagctttgaa gaccacttcc
31681 agagccacct tgaccaccag tgtctatact cccactttgg gaacactgac tcccctcaat
31741 gcatcaaggc aaatggccag cacaatcctc acagaaatga tgatcacaac cccatatgtt
31801 ttccctgatg ttccagaaac gacatcctca ttggctacca gcctgggagc agaaaccagc
31861 acagctcttc ccaggacaac cccatctgtt tcaatagag aatcagagac cacagcctca
31921 ctggtctctc gttctgggc agagagaagt ccggttattc aaactctaga tgtttcttct
31981 agtgagccag atacaacagc ttcatgggtt atccatcctg cagagaccat cccaactgtt
32041 tccaagacaa cccccaattt tttccacagt gaattagaca ctgtatcttc cacagccacc
32101 agtcatgggg cagacgtcag ctcagccatt ccaacaaata tctcacctag tgaactagat
32161 gcactgaccc cactggtcac tatttcgggg acagatacta gtacaacatt cccaacactg
32221 actaagtccc cacatgaaac agagacaaga accacatggc tcactcatcc tgcagagacc
32281 agctcaacta ttcccagaac aatccccaat ttttctcatc atgaatcaga tgccacacct
32341 tcaatagcca ccagtcctgg ggcagaaacc agttcagcta ttccaattat gactgtctca
32401 cctggtgcag aagatctggt gacctcacag gtcactagtt ctgggacaga cagaaatatg
32461 actattccaa ctttgactct ttctcctggt gaaccaaaga cgatagcctc attagtcacc
32521 catcctgaag cacagacaag ttcggccatt ccaacttcaa ctatctcgcc tgctgtatca
32581 cggttggtga cctcaatggt caccagtttg gcggcaaaga caagtacaac taatcgagct
32641 ctgacaaact ccctggtga accagctaca acagtttcat tggtcacgca tcctgcacag
32701 accagcccaa cagttccctg gacaacttcc atttttttcc atagtaaatc agacaccaca
32761 ccttcaatga ccaccagtca tggggcagaa tccagttcag ctgttccaac tccaactgtt
32821 tcaactggaa taccaggagt agtgacccct ttggtcacca gttctagggc agtgatcagt
32881 acaactattc caattctgac tctttctcct ggtgaaccag agaccacacc ttcaatggcc
32941 accagtcatg gggaagaagc cagttctgct attccaactc caactgtttc acctggggta
33001 ccaggagtgg tgacctctct ggtcactagt tctagggcag tgactagtac aactattcca
33061 attctgactt tttctcttgg tgaaccagag accacacctt caatggccac cagtcatggg
33121 acagaagctg gctcagctgt tccaactgtt ttacctgagg taccaggaat ggtgacctct
33181 ctggttgcta gttctaggc agtaaccagt acaactcttc caactctgac tctttctcct
33241 ggtgaaccag agaccacacc ttcaatggcc accagtcatg gggcagaagc cagctcaact
33301 gttccaactg tttcacctga gtaccaggaa gtggtgacct ctctggtcac tagttctagt
33361 ggagtaaaca gtacaagtat tccaactctg attctttctc tggtgaact agaaaccaca
33421 ccttcaatga ccaccagtca tggggcagaa gccagctcaa ctgttccaac tccaactgtt
33481 tcacctgggg tatcaggagt ggtgacccct ctggtcacta gttccagggc agtgaccagt
33541 acaactattc caattctaac tctttcttct agtgagccag agaccacacc ttcaatggcc
33601 accagtcatg gggtagaagc cagctcagct gttctaactg tttcacctga ggtaccagga
33661 atggtgacct ctctggtcac tagttctaga gcagtaacca gtacaactat tccaactctg
33721 actatttctt ctgatgaacc agagaccaca acttcattgg tcacccattc tgaggcaaag
33781 atgatttcag ccattccaac tttagctgtc tccccactg tacaagggct ggtgacttca
33841 ctggtcacta gttctgggtc agagaccagt gcgttttcaa atctaactgt tgcctcaagt
```

Figure 3A (continued)

```
33901 caaccagaga ccatagactc atgggtcgct catcctggga cagaagcaag ttctgttgtt
33961 ccaactttga ctgtctccac tggtgagccg tttacaaata tctcattggt cacccatcct
34021 gcagagagta gctcaactct tcccaggaca acctcaaggt ttcccacag tgaattagac
34081 actatgcctt ctacagtcac cagtcctgag gcagaatcca gctcagccat ttcaactact
34141 atttcacctg gtataccagg tgtgctgaca tcactggtca ctagctctgg gagagacatc
34201 agtgcaactt ttccaacagt gcctgagtcc ccacatgaat cagaggcaac agcctcatgg
34261 gttactcatc ctgcagtcac cagcacaaca gttcccagga caaccccta ttattctcat
34321 agtgaaccag acaccacacc atcaatagcc accagtcctg gggcagaagc cacttcagat
34381 tttccaacaa taactgtctc acctgatgta ccagatatgt taacctcaca ggtcactagt
34441 tctgggacag acaccagtat aactattcca actctgactc tttcttctgg tgagccagag
34501 accacaacct catttatcac ctattctgag acacacacaa gttcagccat tccaactctc
34561 cctgtctccc ctggtgcatc aaagatgctg acctcactgg tcatcagttc tgggacagac
34621 agcactacaa ctttcccaac actgacggag accccatatg aaccagagac aacagccata
34681 cagctcattc atcctgcaga gaccaacaca atggttccca agacaactcc caagttttcc
34741 catagtaagt cagacaccac actcccagta gccatcacca gtcctgggcc agaagccagt
34801 tcagctgttt caacgacaac tatctcacct gatatgtcag atctggtgac ctcactggtc
34861 cctagttctg ggacagacac cagtacaacc ttcccaacat tgagtgagac cccatatgaa
34921 ccagagacta cagtcacgtg gctcactcat cctgcagaaa ccagcacaac ggtttctggg
34981 acaattccca acttttccca tagggatca gacactgcac cctcaatggt caccagtcct
35041 ggagtagaca cgaggtcagg tgttccaact acaaccatcc cacccagtat accagggta
35101 gtgacctcac aggtcactag ttctgcaaca gacactagta cagctattcc aactttgact
35161 ccttctcctg gtgaaccaga gaccacagcc tcatcagcta cccatcctgg gacacagact
35221 ggcttcactg ttccaattcg gactgttccc tctagtgagc cagatacaat ggcttcctgg
35281 gtcactcatc ctccacagac cagcacacct gtttccagaa caacctccag ttttttccat
35341 agtagtccag atgccacacc tgtaatggcc accagtccta ggacagaagc cagttcagct
35401 gtactgacaa caatctcacc tggtgcacca gagatggtga cttcacagat cactagttct
35461 ggggcagcaa ccagtacaac tgttccaact ttgactcatt ctcctggtat gccagagacc
35521 acagccttat tgagcaccca tcccagaaca gggacaagta aaacatttcc tgcttcaact
35581 gtgtttcctc aagtatcaga gaccacagcc tcactcacca ttagacctgg tgcagagact
35641 agcacagctc tcccaactca gacaacatcc tctctcttca ccctacttgt aactggaacc
35701 agcagagttg atctaagtcc aactgcttca cctggtgttt ctgcaaaac agccccactt
35761 tccacccatc cagggacaga gaccagcaca atgattccaa cttcaactct ttcccttggt
35821 ttactagaga ctacaggctt actgccacc agctcttcag cagagaccag cacgagtact
35881 ctaactctga ctgtttcccc tgctgtctct gggctttcca gtgcctctat aacaactgat
35941 aagccccaaa ctgtgacctc ctggaacaca gaaacctcac catctgtaac ttcagttgga
36001 cccccagaat tttccaggac tgtcacaggc accactatga ccttgatacc atcagagatg
36061 ccaacaccac ctaaaaccag tcatggagaa ggagtgagtc caaccactat cttgagaact
36121 acaatggttg aagccactaa tttagctacc acaggttcca gtcccactgt ggccaagaca
36181 acaaccacct tcaatacact ggctggaagc ctctttactc ctctgaccac acctgggatg
36241 tccacccttgg cctctgagag tgtgacctca agaacaagtt ataaccatcg gtcctggatc
36301 tccaccacca gcagttataa ccgtcggtac tggaccccctg ccaccagcac tccagtgact
36361 tctacattct ccccaggat tccacatcc tccatccca gctccacagc agccacagtc
36421 ccattcatgg tgccattcac cctcaacttc accatcacca acctgcagta cgaggaggac
36481 atgcggcacc ctggttccag gaagttcaac gccacagaga gagaactgca gggtctgctc
36541 aaacccttgt tcaggaatag cagtctggaa tacctctatt caggctgcag actagcctca
36601 ctcaggccag agaaggatag ctcagccatg gcagtggatg ccatctgcac acatcgccct
36661 gaccctgaag acctcggact ggacagagag cgactgtact gggagctgag caatctgaca
36721 aatggcatcc aggagctggg ccctacacc ctggaccgga acagtctcta tgtcaatggt
36781 ttcacccatc gaagctctat gcccaccacc agcactcctg ggacctccac agtggatgtg
36841 ggaacctgga ggactccatc ctccagcccc agcccacgg ctgctgaccc tctcctgatg
36901 ccgttcaccc tcaacttcac catcaccaac ctgcagtacg aggaggacat gcgtcgcact
36961 ggctccagga agttcaacac catggagagt gtcctgcagg gtctgctcaa gcccttgttc
37021 aagaacacca gtgttggccc tctgtactct ggctgcagat tgaccttgct caggcccgag
37081 aaagatgggg cagccactgg agtggatgcc atctgcaccc accgccttga ccccaaaagc
37141 cctggactca caggagcac gctgtactgg gagctaagca actgaccaa tgacattgaa
37201 gagctgggcc cctacaccct ggacaggaac agtctctatg tcaatggttt cacccatcag
37261 agctctgtgt ccaccaccag cactcctggg acctccacag tggatctcag aacctcaggg
37321 actccatcct ccctctccag ccccacaatt atggctgctg ccctctcct ggtaccattc
37381 accctcaact tcaccatcac caacctgcag tatgggagg acatgggtca ccctggctcc
37441 aggaagttca acaccacaga gagggtcctg cagggtctgc ttggtccat attcaagaac
37501 accagtgttg gccctctgta ctctggctgc agactgacct ctctcaggtc tgagaaggat
37561 ggagcagcca ctggagtgga tgccatctgc atccatcatc ttgacccaa aagccctgga
37621 ctcaacagag agcggctgta ctgggagctg agccaactga ccaatggcat caaagagctg
37681 ggcccctaca ccctggacag gaacagtctc tatgtcaatg gtttcaccca tcggacctct
37741 gtgcccacca ccagcactcc tgggacctcc acagtggacc ttgaacctc agggactcca
37801 ttctccctcc caagccccgc aactgctggc cctctcctgg tgctgttcac cctcaacttc
```

Figure 3A (continued)

```
37861 accatcacca acctgaagta tgaggaggac atgcatcgcc ctggctccag gaagttcaac
37921 accactgaga gggtcctgca gactctgctt ggtcctatgt tcaagaacac cagtgttggc
37981 cttctgtact ctggctgcag actgaccttg ctcaggtccg agaaggatgg agcagccact
38041 ggagtggatg ccatctgcac ccaccgtctt gacccaaaa gccctggact ggacagagag
38101 cagctatact gggagctgag ccagctgacc aatggcatca aagagctggg cccctacacc
38161 ctggacagga acagtctcta tgtcaatggt ttcacccatt ggatccctgt gcccaccagc
38221 agcactcctg ggacctccac agtggacctt gggtcaggga ctccatcctc cctcccagc
38281 cccacagctg ctggccctct cctggtgcca ttcaccctca acttcaccat caccaacctg
38341 cagtacgagg aggacatgca tcacccaggc tccaggaagt tcaacaccac ggagcgggtc
38401 ctgcagggtc tgcttggtcc catgttcaag aacaccagtg tcggccttct gtactctggc
38461 tgcagactga ccttgctcag gtccgagaag gatggagcag ccactggagt ggatgccatc
38521 tgcacccacc gtcttgaccc caaaagccct ggagtggaca gggagcagct atactgggag
38581 ctgagccagc tgaccaatgg catcaaagag ctggtccctac acccctgga cagaaacagt
38641 ctctatgtca atggtttcac ccatcagacc tctgcgccca acaccagcac tcctggacc
38701 tccacagtgg accttgggac ctcagggact ccatcctccc tccccagccc tacatcngct
38761 ggccctctcc tggtnccntt caccctcaac ttcaccatca ccaacctgca gtacgaggag
38821 gacatgcggc acccnggntc caggaagttc aacaccacng agagggtnct gcagggtctg
38881 ctnaagcccc tnttcaagag caccagtgtt ggccctctgt actctggctg cagactgacc
38941 ttgctcaggt ccgagaagga tggagcagcc actggagtgg atgccatctg cacccaccgt
39001 cttgacccca aaagccctgg agtggacagg gagcagctat actgggagct gagccagctg
39061 accaatggca tcaaagagct gggtccctac accctggaca gaaacagtct ctatgtcaat
39121 ggtttcaccc atcagacctc tgcgcccaac accagcactc ctgggaccct cacagtggac
39181 cttgggacct cagggactcc atcctccctc ccagcccta catctgctgg ccctctcctg
39241 gtgccattca ccctcaactt caccatcacc aacctgcagt acgaggagga catgcatcac
39301 ccaggctcca ggaagttcaa caccacggag cgggtcctgc agggtctgct tggtcccatg
39361 ttcaagaaca ccagtgtcgg ccttctgtac tctggctgca gactgacctt gctcaggcct
39421 gagaagaatg gggcagccac tggaatggat gccatctgca gccaccgtct tgaccccaaa
39481 agccctggac tcaacagaga gcagctgtac tgggagctga gccagctgac ccatggcatc
39541 aaagagctgg gccctacac cctggacagg aacagtctct atgtcaatgg tttcacccat
39601 cggagctctg tgccccac cagcactcct gggacctca cagtggacct tgggacctca
39661 gggactccat cctccctccc cagccccaca acagcgttc ctctcctggt gccgttcacc
39721 ctcaacttta ccatcaccaa tctgcagtat ggggaggaca tgcgtcaccc tggtccagg
39781 aagttcaaca ccacagagag ggtcctgcag ggtctgcttg gtcccttgtt caagaactcc
39841 agtgtcggcc ctctgtactc tggctgcaga ctgatctctc tcaggtctga gaaggatggg
39901 gcagccactg gagtggatgc catctgcacc caccacctta accctcaaag ccctggactg
39961 gacagggagc agctgtactg gcagctgagc cagatgacca atggcatcaa agagctgggc
40021 ccctacaccc tggaccggaa cagtctctac gtcaatggtt tcacccatcg gagctctggg
40081 ctcaccacca gcactccttg gacttccaca gttgaccttg gaacctcagg gactccatcc
40141 cccgtcccca gccccacaac tgctggccct ctcctggtgc cattcaccct caacttcacc
40201 atcaccaacc tgcagtatga ggaggacatg catcgccctg gatctaggaa gttcaacacc
40261 acagagaggg tcctgcaggg tctgcttagt cccattttca agaactccag tgttggccct
40321 ctgtactctg gctgcagact gacctctctc aggcccgaga aggatgggc agcaactgga
40381 atggatgctg tctgcctcta ccaccctaat cccaaaagac ctggactgga cagagagcag
40441 ctgtactggg agctaagcca gctgacccac aacatcactg agctgggccc ctacagcctg
40501 gacagggaca gtctctatgt caatggtttc acccatcaga actctgtgcc caccaccagt
40561 actcctggga cctccacagt gtactgggca accactggga ctccatcctc cttccccggc
40621 cacacagagc ctggccctct cctgatacca ttcactttca actttaccat caccaacctg
40681 cattatgagg aaaacatgca cacccctggt tccaggaagt tcaacaccac ggagagggtt
40741 ctgcagggtc tgctcaagcc cttgttcaag aacaccagtg ttggccctct gtactctggc
40801 tgcagactga ccctctcag gcccgagaag gatggggcag caactggaat ggatgctgtc
40861 tgcctctacc accctaatcc caaaagacct gggctggaca gagcagct gtactgggag
40921 ctaagccagc tgacccacaa catcactgag ctgggcccct acagcctgga cagggacagt
40981 ctctatgtca atggtttcac ccatcagaac tctgtgccca ccaccagtac tcctgggacc
41041 tccacagtgt actgggcaac cactgggact ccatcctcct ccccggcca cacagagcct
41101 ggccctctcc tgataccatt cactttcaac tttaccatca ccaacctgca ttatgaggaa
41161 aacatgcaac ccctggttc caggaagttc aacaccacgg agagggttct gcagggtctg
41221 ctcaagccct tgttcaagaa caccagtgtt ggccctctgt actctggctg cagactgacc
41281 ttgctcagac ctgagaagca tgaggcagcc actggagtgg acaccatctg tacccaccgc
41341 gttgatccca tcggaccctg actggacagg gagcggctat actgggagct gagccagctg
41401 accaacagca ttaccgaact gggaccctac accctggaca gggacagtct ctatgtcaat
41461 ggcttcaacc ctcggagctc tgtgccaacc accagcactc ctgggacctc cacagtgcac
41521 ctgcaacctt ctgggactcc atcctccctg cctggccaca cagccctgt ccctctcttg
41581 ataccattca ccctcaactt taccatcacc aacctgcatt atgaggaaaa catgcaacac
41641 cctggttcca ggaagttcaa caccacggag agggttctgc agggtctgct caagcccttg
41701 ttcaagaaca ccagtgttgg ccctctgtac tctggctgca gactgacctt gctcagacct
41761 gagaagcatg aggcagccac tggagtggac accatctgta cccaccgcgt tgatcccatc
```

Figure 3A (continued)

```
41821 ggacctggac tgnacagnga gcngctntac tgggagctna gccanctgac caannncatc
41881 nnngagctgg gncccctacac cctggacagg nacagtctct atgtcaatgg tttcacccat
41941 cnganctctg ngcccaccac cagcactcct gggacctcca cagtgnacnt nggnacctcn
42001 gggactccat cctccntccc cngccncaca tctgctggcc ctctcctggt gccattcacc
42061 ctcaacttca ccatcaccaa cctgcagtac gaggaggaca tgcatcaccc aggctccagg
42121 aagttcaaca ccacggagcg ggtcctgcag ggtctgcttg gtcccatgtt caagaacacc
42181 agtgtcggcc ttctgtactc tggctgcaga ctgaccttgc tcaggcctga gaagaatggg
42241 gcagccactg gaatggatgc catctgcagc caccgtcttg accccaaaag ccctggactc
42301 gacagagagc agctgtactg ggagctgagc cagctgaccc atggcatcaa agagctgggc
42361 ccctacaccc tggacaggaa cagtctctat gtcaatggtt tcacccatcg gagctctgtg
42421 gcccccacca gcactcctgg gacctccaca gtggaccttg gacctcagg gactccatcc
42481 tccctcccca gccccacaac agctgttcct ctcctggtgc cgttcaccct caactttacc
42541 atcaccaatc tgcagtatgg ggaggacatg cgtcaccctg gctccaggaa gttcaacacc
42601 acagagaggg tcctgcaggg tctgcttggt cccttgttca agaactccag tgtcggccct
42661 ctgtactctg gctgcagact gatctctctc aggtctgaga aggatggggc agccactgga
42721 gtggatgcca tctgcaccca ccaccttaac cctcaaagcc ctggactgga cagggagcag
42781 ctgtactggc agctgagcca gatgaccaat ggcatcaaag agctgggccc ctacaccctg
42841 gaccggaaca gtctctacgt caatggtttc acccatcgga gctctgggct caccaccagc
42901 actccttgga cttccacagt tgaccttgga acctcaggga ctccatcccc cgtcccagc
42961 cccacaactg ctggccctct cctggtgcca ttcacctaa acttcaccat caccaacctg
43021 cagtatgagg aggacatgca tcgccctgga tctaggaagt tcaacgccac agagagggtc
43081 ctgcagggtc tgcttagtcc catattcaag aactccagtg ttggccctct gtactctggc
43141 tgcagactga cctctctcag gcccgagaag gatggggcag caactggaat ggatgctgtc
43201 tgcctctaca accctaatcc caaaagacct ggactgagca gagagcagct gtactggag
43261 ctaagccagc tgacccacaa catcactgag ctgggcccct acagcctgga cagggacagt
43321 ctctatgtca atggtttcac ccatcagagc tctatgacga ccaccagaac tcctgatacc
43381 tccacaatgc acctggcaac ctcgagaact ccagcctccc tgtctggacc tacgaccgcc
43441 agccctctcc tggtgctatt cacaatcaac tgcaccatca ccaacctgca gtacgaggag
43501 gacatgcgtc gcactggctc caggaagttc aacaccatgg agagtgtcct gcagggtctg
43561 ctcaagccct tgttcaagaa caccagtgtt ggccctctgt actctgctg cagattgacc
43621 ttgctcaggc caagaaaga tggggcagcc actggagtgg atgccatctg caccccaccgc
43681 cttgacccca aaagccctgg actcaacagg gagcagctgt actgggagct aagcaaactg
43741 accaatgaca ttgaagagct gggccctcac acccctggaca ggaacagtct ctatgtcaat
43801 ggtttcaccc atcagagctc tgtgtccacc accagcactc ctgggacctc cacagtggat
43861 ctcagaccct cagggactcc atcctccctc tccagaccatc caattatgnc nnctgnccct
43921 ctcctgntnc cnttcaccnt caacttnacc atcaccaacc tgcantangn ggannacatg
43981 cnncncccng gntccaggaa gttcaacacc acngagaggg tcctacaggg tctgctcagg
44041 cccttgttca agaacaccag tgtcagctct ctgtactctg gttgcagact gaccttgctc
44101 aggcctgaga aggatggggc agccaccaga gtggatgctg cctgcaccta ccgccctgat
44161 cccaaaagcc ctggactgga cagagagcaa ctatactggg agctgagcca gctaacccac
44221 agcatcactg agctgggacc ctacaccctg gacagggtca gtctctatgt caatggcttc
44281 aaccctcgga gctctgtgcc aaccaccagc actcctggga cctccacagt gcacctggca
44341 acctctggga ctccatcctc cctgcctggc cacacancnn ctgncctct cctgntncn
44401 ttcaccntca acttnaccat caccaacctg cantangngg annacatgcn ncnccnggn
44461 tccaggaagt tcaacaccac ngagagggtt ctgcagggtc tgctcaaacc cttgttcagg
44521 aatagcagtc tggaataccct ctattcaggc tgcagactag cctcactcag gccagagaag
44581 gatactctcag ccatgccagt ggatgccatc tgcacacatc gccctgaccc tgaagactc
44641 ggactggaca gagagcgact gtactgggag ctgagcaatc tgacaaatgg catccaggag
44701 ctgggcccct acacctgga ccggaacagt ctctacgtca atggtttcac ccatcggagc
44761 tctgggctca ccaccagcac tccttggact tccacagttg accttggaac ctcagggact
44821 ccatcccccg tccccagccc cacaactgct ggccctctcc tggtgccatt caccctcaac
44881 ttcaccatca ccaacctgca gtatgaggag gacatgcatc gccctggttc aggaggttc
44941 aacaccacgg agagggttct gcagggtctg ctcacgccct tgttcaagaa caccagtgtt
45001 ggccctctgt actctgctg cagactgacc ttgctcagac ctgagaagca agaggcagcc
45061 actggagtgg acaccatctg tacccaccgc gttgatccca tcggacctgg actggacaga
45121 gagcggctat actgggagct gagccagctg accaacagca tcacagagct gggaccctac
45181 accctggata gggacagtct ctatgtcaat ggcttcaacc cttggagctc tgtgccaacc
45241 accagcactc ctgggacctc cacagtgcac ctggcaacct ctgggactcc atcctcctg
45301 cctggcacac cagccctgt cctctcttg ataccattca ccctcaactt taccatcctg
45361 gacctgcatt atgaagaaaa catgcaacac cctggttcca ggaagttcaa caccacggag
45421 agggttctgc agggtctgct caagcccttg ttcaagagca ccagcgttgg ccctctgtac
45481 tctggctgca gactgacctt gctcagacct gagaaacatg ggcagccac tggagtggac
45541 gccatctgca ccctccgcct tgatcccact ggtcctggac tggacagaga gcggctatac
45601 tgggagctga gccagctgac caacagcgtt acagagctgg gccctacac cctggacagg
```

Figure 3A (continued)

```
45661 gacagtctct atgtcaatgg cttcacccat cggagctctg tgccaaccac cagtattcct
45721 gggacctctg cagtgcacct ggaaacctct gggactccag cctccctccc tggccacaca
45781 gcccctggcc ctctcctggt gccattcacc ctcaacttca ctatcaccaa cctgcagtat
45841 gaggaggaca tgcgtcaccc tggttccagg aagttcagca ccacggagag agtcctgcag
45901 ggtctgctca agcccttgtt caagaacacc agtgtcagct ctctgtactc tggttgcaga
45961 ctgaccttgc tcaggcctga aaggatggg gcagccacca gagtggatgc tgtctgcacc
46021 catcgtcctg accccaaaag ccctggactg gacagagagc ggctgtactg gaagctgagc
46081 cagctgaccc acggcatcac tgagctgggc ccctacaccc tggacaggca cagtctctat
46141 gtcaatggtt tcacccatca gagctctatg acgaccacca gaactcctga tacctccaca
46201 atgcacctgg caacctcgag aactccagcc tccctgtctg acctacgac cgccagccct
46261 ctcctggtgc tattcacaat taacttcacc atcactaacc tgcggtatga ggagaacatg
46321 catcaccctg gctctagaaa gtttaacacc acggagagag tccttcaggg tctgctcagg
46381 cctgtgttca agaacaccag tgttggccct ctgtactctg gctgcagact gaccacgctc
46441 aggcccaaga aggatgggc agccaccaaa gtggatgcca tctgcaccta ccgccctgat
46501 cccaaaagcc ctggactgga cagagagcag ctatactggg agctgagcca gctaacccac
46561 agcatcactg agctgggccc ctacacccgg gacagggaca gtctctatgt caatggcttc
46621 acccatcgga gctctgtgcc aaccaccagt attcctggga cctctgcagt gcacctggaa
46681 acctctggga ctccagcctc cctccctggc cacacagccc ctggccctct cctggtgcca
46741 ttcaccctca acttcactat caccaacctg cagtatgagg aggacatgcg tcaccctggt
46801 tccaggaagt tcaacaccac ggagagagtc ctgcagggtc tgctcaagcc cttgttcaag
46861 agcaccagtg ttggccctct gtactctggc tgcagactga ccttgctcag gcctgaaaaa
46921 cgtgggcag ccaccggcgt ggacaccatc tgcactcacc gccttgaccc tctaaaccca
46981 ggactggaca gagcagct atactgggag ctgagcaaac tgaccgtgg catcatcgag
47041 ctgggccct acctcctgga cagaggcagt ctctatgtca atggtttcac ccatcggacc
47101 tctgtgccca ccaccagcac tcctgggacc tccacagtgg accttggaac ctcagggact
47161 ccattctccc tcccaagccc cgcancnnct gncctctcc tgntnccntt caccntcaac
47221 ttnaccatca ccaacctgca ntangnggan nacatgcnnc ncccnggntc caggaagttc
47281 aacaccacng agagggtcct gcagactctg cttggtccta tgttcaagaa caccagtgtt
47341 ggccttctgt actctggctg cagactgacc ttgctcaggt ccgagaagga tggagcagcc
47401 actggagtgg atgccatctg cacccaccgt cttgacccca aaagcccctgg agtggacagg
47461 gagcaactat actgggagct gagccagctg accaatggca ttaaagaact gggcccctac
47521 accctggaca ggaacagtct ctatgtcaat gggttcaccc attggatccc tgtgcccacc
47581 agcagcactc ctgggacctc cacagtggac cttggtcag ggactccatc ctccctcccc
47641 agccccacaa ctgctggccc tctcctggtg ccgttcaccc tcaacttcac catcaccaac
47701 ctgaagtacg aggaggacat gcattgccct ggctccagga agttcaacac cacagagaga
47761 gtcctgcaga gtctgcttgg tcccatgttc aagaacacca gtgttggcc tctgtactct
47821 ggctgcagac tgaccttgct caggtccgag aaggatggag cagccactgg agtggatgcc
47881 atctgcaccc accgtcttga ccccaaaagc cctggagtgg acagggagca gctatactgg
47941 gagctgagcc agctgaccaa tggcatcaaa gagctgggtc cctacaccct ggacagaaac
48001 agtctctatg tcaatggttt cacccatcag acctctgcgc caacaccag cactcctggg
48061 acctccacag tggaccttgg gacctcaggg actccatcct ccctccccag ccctacancn
48121 nctgnccctc tcctgntncc nttcaccntc aacttnacca tcaccaacct gcantangng
48181 gannacatgc nncnccngg ntccaggaag ttcaacacca cngagngngt nctgcaggt
48241 ctgctnnnnc cntnttcaa gaacnccagt gtnggcctc tgtactctgg ctgcagactg
48301 acctnnctca ggncngagaa gnatggngca gccactggan tggatgccat ctgcanccac
48361 cnncntnanc ccaaaagncc tggactgnac agngagcngc tntactggga gctnagccan
48421 ctgaccaann ncatcnnnga gctgggnnca tacaccctgg acaggnacag tctctatgtc
48481 aatggtttca cccattggat ccctgtgccc accagcagca ctcctgggac ctccacagtg
48541 gaccttggt cagggactcc atcctccctc cccagcccca caactgctgg ccctctcctg
48601 gtgccgttca ccctcaactt caccatcacc aacctgaagt acgaggagga catgcattgc
48661 cctggctcca ggaagttcaa caccacagag agtcctgcc agagtctgct tggtcccatg
48721 ttcaagaaca ccagtgttgg ccctctgtac tctggctgca gactgacctc gctcaggtcc
48781 gagaaggatg gagcagccac tggagtggat gccatctgca cccaccgtgt tgacccccaa
48841 agccctggag tggacaggga gcagctatac tgggagctga gccagctgac caatggcatc
48901 aaaagagctgg gtccctacac cctggacaga aacagtctct atgtcaatgg tttcacccat
48961 cagacctctg cgccaaacac cagcactcct gggacctcca cagtgnacnt nggnacctcn
49021 gggactccat cctccntccc cagccncaca tctgctggcc ctctcctggt gccattcacc
49081 ctcaacttca ccatcaccaa cctgcagtac gaggaggaca tgcatcaccc aggctccagg
49141 aagttcaaca ccacggagcg ggtcctgcag gtctgcttg tcccatgtt caagaacacc
49201 agtgtcggcc ttctgtactc tggctgcaga ctgaccttgc tcaggcctga aggaatggg
49261 gcaaccactg gaatggatgc catctgcacc caccgtcttg accccaaaag ccctggactg
49321 nacagngagc ngctntactg ggagctnagc canctgacca annncatcnn ngagctgggn
49381 ccctacaccc tggacaggna cagtctctat gtcaatggtt tcacccatcn ganctctgng
49441 cccaccacca gcactcctgg gacctccaca gtgnacntng gnacctcngg gactccatcc
49501 tccntccccn gccnacanc nnctgnccct ctcctgntnc cnttcaccnt caacttnacc
49561 atcaccaacc tgcantangn ggannacatg cnncnccng gntccaggaa gttcaacacc
```

Figure 3A (continued)

```
49621 acngagaggg ttctgcaggg tctgctcaaa cccttgttca ggaatagcag tctggaatac
49681 ctctattcag gctgcagact agcctcactc aggccagaga aggatagctc agccatggca
49741 gtggatgcca tctgcacaca tcgccctgac cctgaagacc tcggactgga cagagagcga
49801 ctgtactggg agctgagcaa tctgacaaat ggcatccagg agctgggccc ctacaccctg
49861 gaccggaaca gtctctatgt caatggtttc acccatcgaa gctctatgcc caccaccagc
49921 actcctggga cctccacagt ggatgtggga acctcaggga ctccatcctc cagccccagc
49981 cccacgactg ctggccctct cctgatacca ttcaccctca acttcaccat caccaacctg
50041 cagtatgggg aggacatggg tcaccctggc tccaggaagt tcaacaccac agagagggtc
50101 ctgcagggtc tgcttggtcc catattcaag aacaccagtg ttggccctct gtactctggc
50161 tgcagactga cctctctcag gtctgagaag gatggagcag ccactggagt ggatgccatc
50221 tgcatccatc atcttgaccc caaaagccct ggactcaaca gagagcggct gtactgggag
50281 ctgagccaac tgaccaatgg catcaaagag ctgggcccct acaccctgga caggaacagt
50341 ctctatgtca atggtttcac ccatcggacc tctgtgccca ccaccagcac tcctgggacc
50401 tccacagtgg accttggaac ctcagggact ccattctccc tcccaagccc cgcaactgct
50461 ggccctctcc tggtgctgtt caccctcaac ttcaccatca ccaacctgaa gtatgaggag
50521 gacatgcatc gccctggctc aggaagttc aacaccactg agagggtcct gcagactctg
50521 gacatgcatc gccctggctc aggaagttca acaccactg agagggtcct gcagactctg
50581 cttggtccta tgttcaagaa caccagtgtt ggccttctgt actctggctg cagactgacc
50641 ttgctcaggt ccgagaagga tggagcagcc actggagtg atgccatctg cacccaccgt
50701 cttgaccccca aaagccctgg actgnacagn gagcngctnt actgggagct nagccanctg
50761 accaannnca tcnnngagct gggncccctac accctggaca ggnacagtct ctatgtcaat
50821 ggtttcaccc atcngactc tgngcccacc accagcactc ctgggacctc cacagtgnac
50881 ntnggnacct cngggactcc atcctccntc cccngccnca cancnnctgn ccctctcctg
50941 ntnccnttca ccntcaactt naccatcacc aacctgcant angngganna catgcnncnc
51001 ccnggntcca ggaagttcaa caccacngag agagtccttc agggtctgct caggcctgtg
51061 ttcaagaaca ccagtgttgg ccctctgtac tctggctgca gactgacctt gctcaggccc
51121 aagaaggatg gggcagccac caaagtggat gccatctgca cctaccgcc tgatcccaaa
51181 agccctggac tggacagaga gcagctatac tgggagctga gccagctaac ccacagcatc
51241 actgagctgg ccccctacac ccaggacagg acagtctctc atgtcaatgg cttcacccat
51301 cggagctctg tgccaaccac cagtattcct gggacctctg cagtgcacct ggaaaccact
51361 gggactccat cctccttccc cggccacaca gagcctggcc ctctcctgat accattcact
51421 ttcaacttta ccatcaccaa cctgcgttat gaggaaaaca tgcaacaccc tggttccagg
51481 aagttcaaca ccacggagag ggttctgcag gtctgctca cgcccttgtt caagaacacc
51541 agtgttggcc ctctgtactc tggctgcaga ctgaccttgc tcagacctga aagcaggag
51601 gcagccactg gagtggacac catctgtacc caccgcgttg atcccatcgg acctggactg
51661 gacagagagc ggctatactg ggagctgagc cagctgacca acagcatcac agagctggga
51721 ccctacaccc tggatagggga cagtctctat gtcgatggct tcaacccttg gagctctgtg
51781 ccaaccacca gcactcctgg gacctccaca gtgcacctgg caacctctgg gactccatcc
51841 cccctgcctg gccacacagc cctgtccct ctcttgatac cattcaccct caactttacc
51901 atcaccgacc tgcattatga agaaaacatg caacaccctg gttccaggaa gttcaacacc
51961 acggagaggg ttctgcaggg tctgctcaag cccttgttca gagcaccag cgttggccct
52021 ctgtactctg gctgcagact gaccttgctc agacctgaga aacatggggc agccactgga
52081 gtggatgcca tctgcacccct ccgccttgat cccactggtc ctggactgga cagagagcgg
52141 ctatactggg agctgagcca gctgaccaac agcatcacag agctgggacc ctacaccctg
52201 gatagggaca gtctctatgt caatggcttc aaccccttgga gctctgtgcc aaccaccagc
52261 actcctggga cctccacagt gcacctggca acctctggga ctccatcctc cctgcctggc
52321 cacacaactg ctggccctct cctggtgccg ttcaccctca acttcaccat caccaacctg
52381 aagtacgagg aggacatgca ttgccctggc tccaggaagt tcaacaccac agagagagtc
52441 ctgcagagtc tgcatggtcc catgttcaag aacaccagtg ttggccctct gtactctggc
52501 tgcagactga ccttgctcag gtccgagaag gatggagcag ccactggagt ggatgccatc
52561 tgcacccacc gtcttgaccc caaaagccct ggactgnaca gngagcngct ntactgggag
52621 ctnagccanc tgaccaannn catcnnngag ctgggnccct acaccctgga caggnacagt
52681 ctctatgtca atggtttcac ccatcngact ctgngcccca ccaccagcac tcctgggacc
52741 tccacagtgn acntnggnac ctcngggact ccatcctccn tccccngcc cacancnnct
52801 gncctctcc tgntnccntt caccntcaac ttnaccatca ccaacctgca ntangnggan
52861 nacatgcnnc nccccngtnc caggaagttc aacacacng agngngtnct gcaggtctg
52921 ctnnnncccn tnttcaagaa cnccagtgtn ggccntctgt actctggctg cagactgacc
52981 tnnctcaggn cngagaagna tggngcagcc actggantgg atgccatctg canccaccnn
53041 cntnanccca aaagncctgg actgnacagn gagcngctnt actgggagct nagccanctg
53101 accaacagca tcacagagct gggaccctac accctggata gggacagtct ctatgtcaat
53161 ggtttcaccc atcgaagctc tatgcccacc accagtattc ctgggacctc tgcagtgcac
53221 ctggaaacct ctgggactcc agcctcctc cctggccaca gcccctgg ccctctcctg
53281 gtgccattca ccctcaactt cactatcacc aacctgcagt atgaggagga catgcgtcac
53341 cctggttcca ggaagttcaa caccacggag agtcctgc agggtctgct caagcccttg
53401 ttcaagagca ccagtgttgg ccctctgtac tctggctgca gactgacctt gctcaggcct
```

Figure 3A (continued)

```
53461 gaaaaacgtg gggcagccac cggcgtggac accatctgca ctcaccgcct tgaccctcta
53521 aaccctggac tgnacagnga gcngctntac tgggagctna gccanctgac caannncatc
53581 nnngagctgg gncccctacac cctggacagg nacagtctct atgtcaatgg tttcacccat
53641 cnganctctg ngcccaccac cagcactcct gggacctcca cagtgnacnt nggnacctcn
53701 gggactccat cctccntccc cngccncaca ncnnctgncc ctctcctgnt nccnttcacc
53761 ntcaacttna ccatcaccaa cctgcantan gnggannaca tgcnncnccc nggntccagg
53821 aagttcaaca ccacngagng ngtnctgcag ggtctgctnn nncccntntt caagaacncc
53881 agtgtnggcc ntctgtactc tggctgcaga ctgacctnnc tcaggncnga gaagnatggn
53941 gcagccactg gantggatgc catctgcanc caccnnnctn ancccaaaag ncctggactg
54001 nacagngagc ngctntactg ggagctnagc canctgacca annncatcnn ngagctgggn
54061 ccctacaccc tggacaggna cagtctctat gtcaatggtt ttcaccctcg gagctctgtg
54121 ccaaccacca gcactcctgg gacctccaca gtgcacctgg caacctctgg gactccatcc
54181 tccctgcctg gccacacagc cctgtccct ctcttgatac cattcaccct caactttacc
54241 atcaccaacc tgcattatga agaaaacatg caacaccctg gttccaggaa gttcaacacc
54301 acggagcggg tcctgcaggg tctgcttggt cccatgttca agaacacaag tgtcggcctt
54361 ctgtactctg gctgcagact gaccttgctc aggcctgaga agaatggggc agccactgga
54421 atggatgcca tctgcagcca ccgtcttgac cccaaaagcc ctggactgna cagngagcng
54481 ctntactggg agctnagcca nctgaccaan nncatcnnng agctgggncc ctacaccctg
54541 gacaggnaca gtctctatgt caatggtttc acccatcnga nctctgngcc caccaccagc
54601 actcctggga cctccacagt gnacntggn acctcnggga ctccatcctc cntcccccngc
54661 cncacancnn ctgnccctct cctgntccn ttcaccntca acttnaccat caccaacctg
54721 cantangngg annacatgcn ncncccnggn tccaggaagt tcaacaccac ngagngngtn
54781 ctgcagggtc tgctnnncc cntnttcaag aacnccagtg tnggccntct gtactctggc
54841 tgcagactga cctnnctcag gncngagaag natggngcag ccactggant ggatgccatc
54901 tgcanccacc nncntnancc caaaagncct ggactgnaca gngagcngct ntactgggag
54961 ctnagccanc tgaccaannn catcnnngag ctgggnccct acacccctgga caggnacagt
55021 ctctatgtca atggtttcac ccatcagaac tctgtgccca ccaccagtac tcctgggacc
55081 tccacagtgt actgggcaac cactgggact ccatcctcct tccccggcca cacagagcct
55141 ggccctctcc tgataccatt cactttcaac tttaccatca ccaacctgca ttatgaggaa
55201 aacatgcaac ccctggttc caggaagttc aacaccacgg agagggttct gcagggtctg
55261 ctcacgccct tgttcaagaa caccagtgtt ggccctctgt actctggctg cagactgacc
55321 ttgctcagac ctgagaagca ggaggcagcc actggagtgg acaccatctg tacccaccgc
55381 gttgatccca tcggacctgg actgnacagn gagcngctnt actgggagct nagccanctg
55441 accaannnca tcnnngagct gggnccctac acctggaca ggnacagtct ctatgtcaat
55501 ggtttcaccc atcnganctc tgngcccacc accagcactc ctgggacctc cacagtgnac
55561 ntnggnacct cnggggactcc atcctccntc cccngccnca cancnnnctgn ccctctcctg
55621 ntnccnttca ccntcaactt naccatcacc aacctgcant angngganna catgcnncnc
55681 ccnggntcca ggaagttcaa caccacngag ngngtnctgc agggtctgct nnnncccntn
55741 ttcaagaacn ccagtgtngg ccntctgtac tctggctgca gactgacctn nctcaggncn
55801 gagaagnatg gngcagccac tggantggat gccatctgca nccaccnncn tnacccaaa
55861 agncctggac tgnacagnga gcngctntac tgggagctna gccanctgac caannncatc
55921 nnngagctgg gncccctacac cctggacagg nacagtctct atgtcaatgg tttcacccat
55981 cggagctctg tgccaaccac cagcagtcct gggacctcca cagtgcacct ggcaacctct
56041 gggactccat cctccctgcc tggccacaca gccctgtcc ctctcttgat accattcacc
56101 ctcaacttta ccatcaccaa cctgcattat gaagaaaaca tgcaacaccc tggttccagg
56161 aagttcaaca ccacggagag ggttctgcag ggtctgctca gcccttgtt caagagcacc
56221 agtgttggcc ctctgtactc tggctgcaga ctgaccttgc tcagcctgac gaaacatggg
56281 gcagccactg gagtggacgc catctgcacc ctccgccttg atcccactgg tcctggactg
56341 nacagngagc ngctntactg ggagctnagc canctgacca annncatcnn ngagctgggn
56401 ccctacaccc tggacaggna cagtctctat gtcaatggtt tcaccatcn ganctctgng
56461 cccaccacca gcactcctgg gacctccaca gtgnacntng gnacctcngg gactccatcc
56521 tccntccccn gccncacanc nnctgnccct ctcctgntnc cnttcaccnt caacttnacc
56581 atcaccaacc tgcantangn ggannacatg cnncnccccng gntccaggaa gttcaacacc
56641 acngagngng tnctgcaggg tctgctnnnn ccntnttca agaacnccag tgtnggccnt
56701 ctgtactctg gctgcagact gacctnnctc aggncngaga agnatggngc agccactgga
56761 ntggatgcca tctgcancca ccnncntnan cccaaaagnc ctggactgna cagngagcng
56821 ctntactggg agctnagcca nctgaccaan nncatcnnng agctgggncc ctacaccctg
56881 gacaggnaca gtctctatgt caatggtttc acccatcgga cctctgtgcc caccaccagc
56941 actcctggga cctccacagt gcacctggca acctctggga ctccatcctc ctgcctggc
57001 cacacagccc tgtccctct cttgataccca ttcaccctca actttaccat caccaacctg
57061 cagtatgagg aggacatgca tcgcccctgga tctaggaagt tcaacaccac agagagggtc
57121 ctgcagggtc tgcttagtcc cattttcaag aactccagtg ttggccctct gtactctggc
57181 tgcagactga cctctctcag gcccgagaag gatgggcag caactggaat ggatgctgtc
57241 tgcctctacc accctaatcc caaagacct gggctggaca gagagcagct gtactgcgag
57301 ctaagccagc tgacccacaa catcactgag ctgggcccct acagcctgga cagggacagt
57361 ctctatgtca atggtttcac ccatcagaac tctgtgccca ccaccagtac tcctgggacc
```

Figure 3A (continued)

```
57421 tccacagtgt actgggcaac cactgggact ccatcctcct tccccggcca cacancnnct
57481 gnccctctcc tgntnccntt caccntcaac ttnaccatca ccaacctgca ntangnggan
57541 nacatgcnnc nccnggntc caggaagttc aacaccacng agngngtnct gcagggtctg
57601 ctnnnnccn tnttcaagaa cnccagtgtn ggccntctgt actctggctg cagactgacc
57661 tnnctcaggn cngagaagna tgngcagcc actggantgg atgccatctg canccaccnn
57721 cntnanccca aaagnccgg actgnacagn gagcngctnt actgggagct nagccanctg
57781 accaannnca tcnnngagct gggncccta ccctggaca ggnacagtct ctatgtcaat
57841 ggtttcaccc attggagctc tgggctcacc accagcactc cttggacttc cacagttgac
57901 cttgaacct cagggactcc atccccgtc cccagcccca caactgctgg ccctctcctg
57961 gtgccattca ccctaaactt caccatcacc aacctgcagt atgaggagga catgcatcgc
58021 cctggatcta ggaagttcaa cgccacagag agggtcctgc agggtctgct tagtcccata
58081 ttcaagaaca ccagtgttgg ccctctgtac tctggctgca gactgacctt gctcagacct
58141 gagaagcagg aggcagccac tggagtggac accatctgta cccaccgcgt tgatcccatc
58201 ggacctggac tgnacagnga gcngctntac tgggagctna gccanctgac caannncatc
58261 nnngagctgg gnccctacac cctggacagg nacagtctct atgtcaatgg tttcacccat
58321 cnganctctg ngcccaccac cagcactcca gggactccca cagtgnacnt nggnacctcn
58381 gggactccat cctccntccc cngccncaca ncnnctgncc ctctcctgnt nccnttcacc
58441 ntcaacttna ccatcaccaa cctgcantan gnggannaca tgcnncnccc nggntccagg
58501 aagttcaaca ccacngagng ngtnctgcag ggtctgctnn nnccntntt caagaacncc
58561 agtgtnggcc ntctgtactc tggctgcaga ctgacctnnc tcaggncnga gaagnatggn
58621 gcagccactg gantggatgc catctgcanc caccnnctn ncccaaaag ncctggactg
58681 nacagngagc ngctntactg ggagctnagc canctgacca annncatcnn ngagctgggn
58741 ccctacaccc tggacaggna cagtctctat gtcaatggtt tcacccatcg gagctttggg
58801 ctcaccacca gcactccttg gacttccaca gttgaccttg aacctcagg gactccatcc
58861 cccgtcccca gccccacaac tgctggccct ctcctggtgc cattcaccct aaacttcacc
58921 atcaccaacc tgcagtatga ggaggacatg catgccctg gctccaggaa gttcaacacc
58981 acggagaggg tccttcaggg tctgcttacg cccttgttca ggaacaccag tgtcagctct
59041 ctgtactctg gttgcagact gaccttgctc aggcctgaga aggatgggc agccaccaga
59101 gtggatgctg tctgcaccca tcgtcctgac cccaaaagcc tggactgna cagngagcng
59161 ctntactggg agctnagcca nctgaccaan nncatcnnng agctgggncc ctacaccctg
59221 gacaggnaca gtctctatgt caatggtttc acccatcnga nctctgngcc caccaccagc
59281 actcctggga cctccacagt gnacntggn acctcnggga ctccatcctc cntccccngc
59341 cncacancnn ctgncctct cctgntnccn ttaccntca acttnaccat caccaacctg
59401 cantangngg annacatgcn ncnccnggn tccaggaagt tcaacaccac ngagngngtn
59461 ctgcagggtc tgctnnnncc cntnttcaag aacnccagtg tnggccntct gtactctggc
59521 tgcagactga cctnnctcag gncngagaag natgggncag ccactggant ggatgccatc
59581 tgcanccacc nncntnancc caaaagncct ggactgnaca gngagcngct ntactgggag
59641 ctnagccanc tgaccaannn catcnnngag ctgggnccct acaccctgga caggnacagt
59701 ctctatgtca atggtttcac ccattggatc cctgtgccca ccagcagcac tcctgggacc
59761 tccacagtgg accttgggtc agggactcca tcctccctcc ccagcccac aactgctggc
59821 cctctcctgg taccattcac cctcaacttc accatcacca acctgcagta tgggggagac
59881 atgggtcacc ctggctccag gaagttcaac accacagaga gggtcctgca gggtctgctt
59941 ggtcccatat tcaagaacac cagtgttggc cctctgtact ctggctgcag actgacctct
60001 ctcaggtccg agaaggatgg agcagccact ggagtggatg ccatctgcat ccatcatctt
60061 gaccccaaaa gccctggact gnacagngag cngctntact gggagctnag ccanctgacc
60121 aannncatcn nngagctggg nccctacacc ctggacaggn acagtctcta tgtcaatggt
60181 ttcacccatc nganctctgn gcccaccacc agcactcctg ggacctccac agtgnacntn
60241 ggnacctcng ggactccatc ctccntcccc ngccncacan cnnctgnccc tctcctgntn
60301 ccnttcaccn tcaacttnac catcaccaac ctgcantang nggannacat gcnncnccn
60361 ggntccagga agttcaacac cacngagngn gtnctgcagg gtctgctnn nccntnttc
60421 aagaacncca gtgtnggccn tctgtactct ggctgcagac tgacctnnct caggncgag
60481 aagnatgggn cagccactgg antggatgcc atctgcancc accnncntna ncccaaaagn
60541 cctggactgn acagngagcn gctntactgg gagctnagcc anctgaccaa nnncatcnnn
60601 gagctgggnc cctacaccct ggacaggnac agtctctatg tcaatggttt cacccatcag
60661 accttgtgcgc ccaacaccag cactcctggg acctccacag tggaccttgg gacctcaggg
60721 actccatcct ccctcccag ccctacatct gctggccctc tcctggtgcc attcaccctc
60781 aacttcacca tcaccaacct gcagtacgag gaggacatgc atcccagg ctccaggaag
60841 ttcaacacca cggagcgggt cctgcagggt ctgcttggtc ccatgttcaa gaacaccagt
60901 gtcggccttc tgtactctgg ctgcagactg accttgctca ggcctgagaa gaatggggca
60961 gccaccagag tggatgctgt ctgcacccat cgtcctgacc caaaagccc tggactgnac
61021 agngagcngc tntactggga gctnagccan ctgaccaann ncatcnnnga gctgggnccc
61081 tacaccctgg acaggnacag tctctatgtc aatggtttca cccatcngan ctctgngccc
61141 accaccagca ctcctgggac tccacagtg nacntggna cctcngggac tccatcctcc
61201 ntccccngcc ncacagcccc tgtccctctc ttgataccat tcaccctcaa ctttaccatc
61261 accaacctgc attatgaaga aaacatgcaa cacctggtt ccaggaagtt caacaccacg
```

Figure 3A (continued)

```
61321 gagagggttc tgcagggtct gctcaagccc ttgttcaaga gcaccagcgt tggccctctg
61381 tactctggct gcagactgac cttgctcaga cctgagaaac atggggcagc cactggagtg
61441 gacgccatct gcaccctccg ccttgatccc actggtcctg gactggacag agagcggcta
61501 tactgggagc tgagccagct gaccaacagc gttacagagc tgggccccta caccctggac
61561 agggacagtc tctatgtcaa tggcttcacc cagcggagct ctgtgccaac caccagtatt
61621 cctgggacct ctgcagtgca cctggaaacc tctgggactc cagcctccct ccctggccac
61681 acagccctg gccctctcct ggtgccattc accctcaact tcactatcac caacctgcag
61741 tatgaggtgg acatgcgtca ccctggttcc aggaagttca acaccacgga gagagtcctg
61801 cagggtctgc tcaagccctt gttcaagagc accagtgttg gccctctgta ctctggctgc
61861 agactgacct tgctcaggcc tgaaaaacgt ggggcagcca ccggcgtgga caccatctgc
61921 actcaccgcc ttgaccctct aaaccctgga ctggacagag agcagctata ctgggagctg
61981 agcaaactga cccgtgcat catcgagctg gcccctacc tcctggacag aggcagtctc
62041 tatgtcaatg gtttcaccca tcggaacttt gtgcccatca ccagcactcc tgggacctcc
62101 acagtacacc taggaacctc tgaaactcca tcctccctac ctagacccat agtgcctggc
62161 cctctcctgg tgccattcac cctcaacttc accatcacca acttgcagta tgaggaggcc
62221 atgcgacacc ctggctccag gaagttcaat accacggaga gggtcctaca gggtctgctc
62281 aggcccttgt tcaagaatac cagtatcggc cctctgtact ccagctgcag actgaccttg
62341 ctcaggccag agaaggacaa ggcagccacc agagtggatg ccatctgtac ccaccaccct
62401 gaccctcaaa gccctggact gaacagagag cagctgtact gggagctgag ccagctgacc
62461 cacggcatca ctgagctggg ccctacacc ggtgacaggg acagtctcta tgtcgatggt
62521 ttcactcatt ggagcccat accgaccacc agcactcctg ggacctccat agtgaacctg
62581 ggaacctctg ggatcccacc ttccctccct gaaactacan cnnctgnccc tctcctgntn
62641 ccnttcaccn tcaacttnac catcaccaac ctgcantang nggannacat gcnncnccn
62701 ggntccagga agttcaacac cacngagagg gttctgcagg gtctgctcaa gcccttgttc
62761 aagagcacca gtgttggccc tctgtattct ggctgcagac tgaccttgct caggcctgag
62821 aaggacggag tagccaccag agtgacgcc atctgcaccc accgccctga ccccaaaatc
62881 cctgggctag acagacagca gctatactgg gagctgagcc agctgaccca cagcatcact
62941 gagctggac cctacaccct ggatagggac agtctctatg tcaatggttt cacccagcgg
63001 agctctgtgc caccaccag cactcctggg actttcacag tacagccgga aacctctgag
63061 actccatcat ccctccctgg cccacagcc actggccctg tcctgctgcc attcaccctc
63121 aattttacca tcactaacct gcagtatgag gaggacatgc atcgccctgg ctccaggaag
63181 ttcaacacca cggagagggt ccttcagggt ctgcttatgc ccttgttcaa gaacaccagt
63241 gtcagctctc tgtactctgg ttgcagactg accttgctca ggcctgagaa ggatggggca
63301 gccaccagag tggatgctgt ctgcacccat cgtcctgacc ccaaaagccc tggactggac
63361 agagcggc tgtactggaa gctgagccag ctgacccacg gcatcactga gctgggcccc
63421 tacaccctgg acaggcacag tctctatgtc aatggtttca cccatcagag ctctatgacg
63481 accaccagaa ctcctgatac ctccacaatg cacctggcaa cctcgagaac tccagcctcc
63541 ctgtctggac ctacgaccgc cagccctctc ctggtgctat tcacaattaa cttcaccatc
63601 actaacctgc ggtatgagga gaacatgcat caccctggct ctagaaagtt taacaccacg
63661 gagagagtcc ttcagggtct gctcaggcct gtgttcaaga acaccagtgt tggccctctg
63721 tactctggct gcagactgac cttgctcagg cccaagaagg atggggcagc caccaaagtg
63781 gatgccatct gcacctaccg ccctgatccc aaaagccctg gactggacag agagcagcta
63841 tactgggagc tgagccagct aacccacagc atcactgagc tgggccccta caccctggac
63901 agggacagtc tctatgtcaa tggtttcaca cagcggagct ctgtgcccac cactagcatt
63961 cctgggaccc ccacagtgga cctgggaaca tctgggactc cagtttctaa acctggtccc
64021 tcggctgcca gccctctcct ggtgctattc actctcaact tcaccatcac caacctgcgg
64081 tatgaggaga acatgcagca ccctggctcc aggaagttca acaccacgga gagggtcctt
64141 cagggcctgc tcaggtccct gttcaagagc accagtgttg ccctctgta ctctggctgc
64201 agactgactt tgctcaggcc tgaaaaggat gggacagcca ctggagtgga tgccatctgc
64261 acccaccacc ctgacccaa aagccctagg ctggacagag agcagctgta ttgggagctg
64321 agccagctga cccacactg ggctcactg ccctggacaa cgacagccctg
64381 tttgtcaatg gtttcactca tcggagctct gtgtccacca ccagcactcc tgggaccccc
64441 acagtgtatc tgggagcatc taagactcca gcctcgatat tggcccttc agctgccagc
64501 catctcctga tactattcac cctcaacttc accatcacta acctgcggta tgaggagaac
64561 atgtggcctg gctccaggaa gttcaacact acagagaggg tccttcaggg cctgctaagg
64621 cccttgttca agaacaccag tgttggccct ctgtactctg gctccaggct gaccttgctc
64681 aggccagaga agatgggga gccaccgga gtggatgcca tctgcaccca ccgccctgac
64741 cccacaggcc ctgggctgga cagagcag ctgtatttgg agctgagcca gctgacccac
64801 agcatcactg agctgggccc ctacacactg acagggaca gtctctatgt caatggtttc
64861 acccatcgga gctctgtacc caccaccagc accgggtgg tcagcgagga gccattcaca
64921 ctgaacttca ccatcaacaa cctgcgctac atgcggaca tggccaacc cggctccctc
64981 aagttcaaca tcacagacaa cgtcatgaag cacctgctca gtcctttgtt ccagaggagc
65041 agcctgggtg cacggtacac aggctgcagg gtcatcgcac taaggtctgt gaagaacggt
65101 gctgagacac gggtggacct cctctgcacc tacctgcagc ccctcagcgg cccaggtctg
```

Figure 3A (continued)

```
65161 cctatcaagc aggtgttcca tgagctgagc cagcagaccc atggcatcac ccggctgggc
65221 ccctactctc tggacaaaga cagcctctac cttaacggtt acaatgaacc tggtctagat
65281 gagcctccta caactcccaa gccagccacc acattcctgc ctcctctgtc agaagccaca
65341 acagccatgg ggtaccacct gaagaccctc acactcaact tcaccatctc caatctccag
65401 tattcaccag atatgggcaa gggctcagct acattcaact ccaccgaggg ggtccttcag
65461 cacctgctca gacccttgtt ccagaagagc agcatgggcc ccttctactt gggttgccaa
65521 ctgatctccc tcaggcctga gaaggatggg gcagccactg gtgtggacac cacctgcacc
65581 taccaccctg accctgtggg ccccgggctg gacatacagc agctttactg ggagctgagt
65641 cagctgaccc atggtgtcac ccaactgggc ttctatgtcc tggacaggga tagcctcttc
65701 atcaatggct atgcacccca gaatttatca atccggggcg agtaccagat aaatttccac
65761 attgtcaact ggaacctcag taatccagac cccacatcct cagagtacat caccctgctg
65821 agggacatcc aggacaaggt caccacactc tacaaaggca gtcaactaca tgacacattc
65881 cgcttctgcc tggtcaccaa cttgacgatg gactccgtgt tggtcactgt caaggcattg
65941 ttctcctcca atttggaccc cagcctggtg gagcaagtct ttctagataa gaccctgaat
66001 gcctcattcc attggctggg ctccacctac cagttggtgg acatccatgt gacagaaatg
66061 gagtcatcag tttatcaacc aacaagcagc tccagcaccc agcacttcta cctgaatttc
66121 accatcacca acctaccata ttcccaggac aaagcccagc caggcaccac caattaccag
66181 aggaacaaaa ggaatattga ggatgcgctc aaccaactct tccgaaacag cagcatcaag
66241 agttattttt ctgactgtca agtttcaaca ttcaggtctg tccccaacag gcaccacacc
66301 ggggtggact ccctgtgtaa cttctcgcca ctggctcgga gagtagacag agttgccatc
66361 tatgaggaat ttctgcggat gacccggaat ggtacccagc tgcagaactt caccctggac
66421 aggagcagtg tccttgtgga tgggtattct cccaacagaa atgagccctt aactgggaat
66481 tctgaccttc ccttctgggc tgtcatcctc atcggcttgg caggactcct gggactcatc
66541 acatgcctga tctgcggtgt cctggtgacc acccgccggc ggaagaagga aggagaatac
66601 aacgtccagc aacagtgccc aggctactac cagtcacacc tagacctgga ggatctgcaa
66661 tgactggaac ttgccggtgc ctggggtgcc tttcccccag ccagggtcca aagaagcttg
66721 gctggggcag aaataaacca tattggtcgg aaaaaaaaaa aaaaa
```

Figure 3A (continued)

Polypeptide sequence (SEQ ID No:2)

```
MLKPSGLPGSSSPTRSLMTGSRSTKATPEMDSGLTGATLSPKTS
TGAIVVTEHTLPFTSPDKTLASPTSSVVGRTTQSLGVMSSALPESTSRGMTHSEQRTS
PSLSPQVNGTPSRNYPATSMVSGLSSPRTRTSSTEGNFTKEASTYTLTVETTSGPVTE
KYTVPTETSTTEGDSTETPWDTRYIPVKITSPMKTFADSTASKENAPVSMTPAETTVT
DSHTPGRTNPSFGTLYSSFLDLSPKGTPNSRGETSLELILSTTGYPFSSPEPGSAGHS
RISTSAPLSSSASVLDNKISETSIFSGQSLTSPLSPGVPEARASTMPNSAIPFSMTLS
NAETSAERVRSTISSLGTPSISTKQTAETILTFHAFAETMDIPSTHIAKTLASEWLGS
PGTLGGTSTSALTTTSPSTTLVSEETNTHHSTSGKETEGTLNTSMTPLETSAPGEESE
MTATLVPTLGFTTLDSKIRSPSQVSSSHPTRELRTTGSTSGRQSSSTAAHGSSDILRA
TTSSTSKASSWTSESTAQQFSEPQHTQWVETSPSMKTERPPASTSVAAPITTSVPSVV
SGFTTLKTSSTKGIWLEETSADTLIGESTAGPTTHQFAVPTGISMTGGSSTRGSQGTT
HLLTRATASSETSADLTLATNGVPVSVSPAVSKTAAGSSPPGGTKPSYTMVSSVIPET
SSLQSSAFREGTSLGLTPLNTRHPFSSPEPDSAGHTKISTSIPLLSSASVLEDKVSAT
STFSHHKATSSITTGTPEISTKTKPSSAVLSSMTLSNAATSPERVRNATSPLTHPSPS
GEETAGSVLTLSTSAETTDSPNIHPTGTLTSESSESPSTLSLPSVSGVKTTFSSSTPS
THLFTSGEETEETSNPSVSQPETSVSRVRTTLASTSVPTPVFPTMDTWPTRSAQFSSS
HLVSELRATSSTSVTNSTGSALPKISHLTGTATMSQTNRDTFNDSAAPQSTTWPETSP
RFKTGLPSATTTVSTSATSLSATVMVSKFTSPATSSMEATSIREPSTTILTTETTNGP
GSMAVASTNIPIGKGYITEGRLDTSHLPIGTTASSETSMDFTMAKESVSMSVSPSQSM
DAAGSSTPGRTSQFVDTFSDDVYHLTSREITIPRDGTSSALTPQMTATHPPSPDPGSA
RSTWLGILSSSPSSPTPKVTMSSTFSTQRVTTSMIMDTVETSRWNMPNLPSTTSLTPS
NIPTSGAIGKSTLVPLDTPSPATSLEASEGGLPTLSTYPESTNTPSIHLGAHASSESP
STIKLTMASVVKPGSYTPLTFPSIETHIHVSTARMAYSSGSSPEMTAPGETNTGSTWD
PTTYITTTDPKDTSSAQVSTPHSVRTLRTTENHPKTESATPAAYSGSPKISSSPNLTS
PATKAWTITDTTEHSTQLHYTKLAEKSSGFETQSAPGPVSVVIPTSPTIGSSTLELTS
DVPGEPLVLAPSEQTTITLPMATWLSTSLTEEMASTDLDISSPSSPMSTFAIFPPMST
PSHELSKSEADTSAIRNTDSTTLDQHLGIRSLGRTGDLTTVPITPLTTTWTSVIEHST
QAQDTLSATMSPTHVTQSLKDQTSIPASASPSHLTEVYPELGTQGRSSSEATTFWKPS
TDTLSREIETGPTNIQSTPPMDNTTTGSSSSGVTLGIAHLPIGTSSPAETSTNMALER
RSSTATVSMAGTMGLLVTSAPGRSISQSLGRVSSVLSESTTEGVTDSSKGSSPRLNTQ
GNTALSSSLEPSYAEGSQMSTSIPLTSSPTTPDVEFIGGSTFWTKEVTTVMTSDISKS
SARTESSSATLMSTALGSTENTGKEKLRTASMDLPSPTPSMEVTPWISLTLSNAPNTT
DSLDLSHGVHTSSAGTLATDRSLNTGVTRASRLENGSDTSSKSLSMGNSTHTSMTDTE
KSEVSSSIHPRPETSAPGAETTLTSTPGNRAISLTLPFSSIPVEEVISTGITSGPDIN
SAPMTHSPITPPTIVWTSTGTIEQSTQPLHAVSSEKVSVQTQSTPYVNSVAVSASPTH
ENSVSSGSSTSSPYSSASLESLDSTISRRNAITSWLWDLTTSLPTTTWPSTSLSEALS
SGHSGVSNPSSTTTEFPLFSAASTSAAKQRNPETETHGPQNTAASTLNTDASSVTGLS
ETPVGASISSEVPLPMAITSRSDVSGLTSESTANPSLGTASSAGTKLTRTISLPTSES
LVSFRMNKDPWTVSIPLGSHPTTNTETSIPVNSAGPPGLSTVASDVIDTPSDGAESIP
TVSFSPSPDTEVTTISHFPEKTTHSFRTISSLTHELTSRVTPIPGDWMSSAMSTKPTG
ASPSITLGERRTITSAAPTTSPIVLTASFTETSTVSLDNETTVKTSDILDARKTNELP
SDSSSSSDLINTSIASSTMDVTKTASISPTSISGMTASSSPSLFSSDRPQVPTSTTET
NTATSPSVSSNTYSLDGGSNVGGTPSTLPPFTITHPVETSSALLAWSRPVRTFSTMVS
TDTASGENPTSSNSVVTSVPAPGTWASVGSTTDLPAMGFLKTSPAGEAHSLLASTIEP
ATAFTPHLSAAVVTGSSATSEASLLTTSESKAIHSSPQTPTTPTSGANWETSATPESL
LVVTETSDTTLTSKILVTDTILFSTVSTPPSKFPSTGTLSGASFPTLLPDTPAIPLTA
TEPTSSLATSFDSTPLVTIASDSLGTVPETTLTMSETSNGDALVLKTVSNPDRSIPGI
TIQGVTESPLHPSSTSPSKIVAPRNTTYEGSITVALSTLPAGTTGSLVFSQSSENSET
TALVDSSAGLERASVMPLTTGSQGMASSGGIRSGSTHSTGTKTFSSLPLTMNPGEVTA
MSEITTNRLTATQSTAPKGIPVKPTSAESGLLTPVSASSSPSKAFASLTTAPPSTWGI
PQSTLTFEFSEVPSLDTKSASLPTPGQSLNTIPDSDASTASSSLSKSPEKNPRARMMT
```

Figure 3B

```
STKAISASSFQSTGFTETPEGSASPSMAGHEPRVPTSGTGDPRYASESMSYPDPSKAS
SAMTSTSLASKLTTLFSTGQAARSGSSSSPISLSTEKETSFLSPTASTSRKTSLFLGP
SMARQPNILVHLQTSALTLSPTSTLNMSQEEPPELTSSQTIAEEEGTTAETQTLTFTP
SETPTSLLPVSSPTEPTARRKSSPETWASSISVPAKTSLVETTDGTLVTTIKMSSQAA
QGNSTWPAPAEETGTSPAGTSPGSPEVSTTLKIMSSKEPSISPEIRSTVRNSPWKTPE
TTVPMETTVEPVTLQSTALGSGSTSISHLPTGTTSPTKSPTENMLATERVSLSPSPPE
AWTNLYSGTPGGTRQSLATMSSVSLESPTARSITGTGQQSSPELVSKTTGMEFSMWHG
STGGTTGDTHVSLSTSSNILEDPVTSPNSVSSLTDKSKHKTETWVSTTAIPSTVLNNK
IMAAEQQTSRSVDEAYSSTSSWSDQTSGSDITLGASPDVTNTLYITSTAQTTSLVSLP
SGDQGITSLTNPSGGKTSSASSVTSPSIGLETLRANVSAVKSDIAPTAGHLSQTSSPA
EVSILDVTTAPTPGISTTITTMGTNSISTTTPNPEVGMSTMDSTPATERRTTSTEHPS
TWSSTAASDSWTVTDMTSNLKVARSPGTISTMHTTSFLASSTELDSMSTPHGRITVIG
TSLVTPSSDASAVKTETSTSERTLSPSDTTASTPISTFSRVQRMSISVPDILSTSWTP
SSTEAEDVPVSMVSTDHASTKTDPNTPLSTFLFDSLSTLDWDTGRSLSSATATTSAPQ
GATTPQELTLETMISPATSQLPFSIGHITSAVTPAAMARSSGVTFSRPDPTSKKAEQT
STQLPTTTSAHPGQVPRSAATTLDVIPHTAKTPDATFQRQGQTALTTEARATSDSWNE
KEKSTPSAPWITEMMNSVSEDTIKEVTSSSSVLKDPEYAGHKLGIWDDFIPKFGKAAH
MRELPLLSPPQDKEAIHPSTNTVETTGWVTSSEHASHSTIPAHSASSKLTSPVVTTST
REQAIVSMSTTTWPESTRARTEPNSFLTIELRDVSPYMDTSSTTQTSIISSPGSTAIT
KGPRTEITSSKRISSSFLAQSMRSSDSPSEAITRLSNFPAMTESGGMILAMQTSPPGA
TSLSAPTLDTSATASWTGTPLATTQRFTYSEKTTLFSKGPEDTSQPSPPSVEETSSSS
SLVPIHATTSPSNILLTSQGHSPSSTPPVTSVFLSETSGLGKTTDMSRISLEPGTSLP
PNLSSTAGEALSTYEASRDTKAIHHSADTAVTNMEATSSEYSPIPGHTKPSKATSPLV
TSHIMGDITSSTSVFGSSETTEIETVSSVNQGLQERSTSQVASSATETSTVITHVSSG
DATTHVTKTQATFSSGTSISSPHQFITSTNTFTDVSTNPSTSLIMTESSGVTITTQTG
PTGAATQGPYLLDTSTMPYLTETPLAVTPDFMQSEKTTLISKGPKDVTWTSPPSVAET
SYPSSLTPFLVTTIPPATSTLQGQHTSSPVSATSVLTSGLVKTTDMLNTSMEPVTNSP
QNLNNPSNEILATLAATTDIETIHPSINKAVTNMGTASSAHVLHSTLPVSSEPSTATS
PMVPASSMGDALASISIPGSETTDIEGEPTSSLTAGRKENSTLQEMNSTTESNIILSN
VSVGAITEATKMEVPSFDATFIPTPAQSTKFPDIFSVASSRLSNSPPMTISTHMTTTQ
TGSSGATSKIPLALDTSTLETSAGTPSVVTEGFAHSKITTAMNNDVKDVSQTNPPFQD
EASSPSSQAPVLVTTLPSSVAFTPQWHSTSSPVSMSSVLTSSLVKTAGKVDTSLETVT
SSPQSMSNTLDDISVTSAATTDIETTHPSINTVVTNVGTTGSAFESHSTVSAYPEPSK
VTSPNVTTSTMEDTTISRSIPKSSKTTRTETETTSSLTPKLRETSISQEITSSTETST
VPYKELTGATTEVSRTDVTSSSSTSFPGPDQSTVSLDISTETNTRLSTSPIMTESAEI
TITTQTGPHGATSQDTFTMDPSNTTPQAGIHSAMTHGFSQLDVTTLMSRIPQDVSWTS
PPSVDKTSSPSSFLSSPAMTTPSLISSTLPEDKLSSPMTSLLTSGLVKITDILRTRLE
PVTSSLPNFSSTSDKILATSKDSKDTKEIFPSINTEETNVKANNSGHESHSPALADSE
TPKATTQMVITTTVGDPAPSTSMPVHGSSETTNIKREPTYFLTPRLRETSTSQESSFP
TDTSFLLSKVPTGTITEVSSTGVNSSSKISTPDHDKSTVPPDTFTGEIPRVFTSSIKT
KSAEMTITTQASPPESASHSTLPLDTSTTLSQGGTHSTVTQGFPYSEVTTLMGMGPGN
VSWMTTPPVEETSSVSSLMSSPAMTSPSPVSSTSPQSIPSSPLPVTALPTSVLVTTTD
VLGTTSPESVTSSPPNLSSITHERPATYKDTAHTEAAMHHSTNTAVTNVGTSGSGHKS
QSSVLADSETSKATPLMSTTSTLGDTSVSTSTPNISQTNQIQTEPTASLSPRLRESST
SEKTSSTTETNTAFSYVPTGAITQASRTEISSSRTSISDLDRPTIAPDISTGMITRLF
TSPIMTKSAEMTVTTQTTTPGATSQGILPWDTSTTLFQGGTHSTVSQGFPHSEITTLR
SRTPGDVSWMTTPPVEETSSGFSLMSPSMTSPSPVSSTSPESIPSSPLPVTALLTSVL
VTTTNVLGTTSPETVTSSPPNLSSPTQERLTTYKDTAHTEAMHASMHTNTAVANVGTS
ISGHESQSSVPADSHTSKATSPMGITFAMGDTSVSTSTPAFFETRIQTESTSSLIPGL
RDTRTSEEINTVTETSTVLSEVPTTTTTEVSRTEVITSSRTTISGPDHSKMSPYISTE
TITRLSTFPFVTGSTEMAITNQTGPIGTISQATLTLDTSSTASWEGTHSPVTQRFPHS
EETTTMSRSTKGVSWQSPPSVEETSSPSSPVPLPAITSHSSLYSAVSGSSPTSALPVT
SLLTSGRRKTIDMLDTHSELVTSSLPSASSFSGEILTSEASTNTETIHFSENTAETNM
GTTNSMHKLHSSVSIHSQPSGHTPPKVTGSMMEDAIVSTSTPGSPETKNVDRDSTSPL
TPELKEDSTALVMNSTTESNTVFSSVSLDAATEVSRAEVTYYDPTFMPASAQSTKSPD
ISPEASSSHSNSPPLTISTHKTIATQTGPSGVTSLGQLTLDTSTIATSAGTPSARTQD
```

Figure 3B (continued)

```
FVDSETTSVMNNDLNDVLKTSPFSAEEANSLSSQAPLLVTTSPSPVTSTLQEHSTSSL
VSVTSVPTPTLAKITDMDTNLEPVTRSPQNLRNTLATSEATTDTHTMHPSINTAMANV
GTTSSPNEFYFTVSPDSDPYKATSAVVITSTSGDSIVSTSMPRSSAMKKIESETTFSL
IFRLRETSTSQKIGSSSDTSTVFDKAFTAATTEVSRTELTSSSRTSIQGTEKPTMSPD
TSTRSVTMLSTFAGLTKSEERTIATQTGPHRATSQGTLTWDTSITTSQAGTHSAMTHG
FSQLDLSTLTSRVPEYISGTSPPSVEKTSSSSSLLSLPAITSPSPVPTTLPESRPSSP
VHLTSLPTSGLVKTTDMLASVASLPPNLGSTSHKIPTTSEDIKDTEKMYPSTNIAVTN
VGTTTSEKESYSSVPAYSEPPKVTSPMVTSFNIRDTIVSTSMPGSSEITRIEMESTFS
VAHGLKGTSTSQDPIVSTEKSAVLHKLTTGATETSRTEVASSRRTSIPGPDHSTESPD
ISTEVIPSLPISLGITESSNMTIITRTGPPLGSTSQGTFTLDTPTTSSRAGTHSMATQ
EFPHSEMTTVMNKDPEILSWTIPPSIEKTSFSSSLMPSPAMTSPPVSSTLPKTIHTTP
SPMTSLLTPSLVMTTDTLGTSPEPTTSSPPNLSSTSHVILTTDEDTTAIEAMHPSTST
AATNVETTCSGHGSQSSVLTDSEKTKATAPMDTTSTMGHTTVSTSMSVSSETTKIKRE
STYSLTPGLRETSISQNASFSTDTSIVLSEVPTGTTAEVSRTEVTSSGRTSIPGPSQS
TVLPEISTRTMTRLFASPTMTESAEMTIPTQTGPSGSTSQDTLTLDTSTTKSQAKTHS
TLTQRFPHSEMTTLMSRGPGDMSWQSSPSLENPSSLPSLLSLPATTSPPPISSTLPVT
ISSSPLPVTSLLTSSPVTTTDMLHTSPELVTSSPPKLSHTSDERLTTGKDTTNTEAVH
PSTNTAASNVEIPSFGHESPSSALADSETSKATSPMFITSTQEDTTVAISTPHFLETS
RIQKESISSLSPKLRETGSSVETSSAIETSAVLSEVSIGATTEISRTEVTSSSRTSIS
GSAESTMLPEISTTRKIIKFPTSPILAESSEMTIKTQTSPPGSTSESTFTLDTSTTPS
LVITHSTMTQRLPHSEITTLVSRGAGDVPRPSSLPVEETSPPSSQLSLSAMISPSPVS
STLPASSHSSSASVTSPLTPGQVKTTEVLDASAEPETSSPPSLSSTSVEILATSEVTT
DTEKIHPFPNTAVTKVGTSSSGHESPSSVLPDSETTKATSAMGTISIMGDTSVSTLTP
ALSNTRKIQSEPASSLTTRLRETSTSEETSLATEANTVLSKVSTGATTEVSRTEAISF
SRTSMSGPEQSTMSQDISIGTIPRISASSVLTESAKMTITTQTGPSESTLESTLNLNT
ATTPSWVETHSIVIQGFPHPEMTTSMGRGPGGVSWPSPPFVKETSPPSSPLSLPAVTS
PHPVSTTFLAHIPPSPLPVTSLLTSGPATTTDILGTSTEPGTSSSSSLSTTSHERLTT
YKDTAHTEAVHPSTNTGGTNVATTSSGYKSQSSVLADSSPMCTTSTMGDTSVLTSTPA
FLETRRIQTELASSLTPGLRESSGSEGTSSGTKMSTVLSKVPTGATTEISKEDVTSIP
GPAQSTISPDISTRTVSWFSTSPVMTESAEITMNTHTSPLGATTQGTSTLATSSTTSL
TMTHSTISQGFSHSQMSTLMRRGPEDVSWMSPPLLEKTRPSFSLMSSPATTSPSPVSS
TLPESISSSPLPVTSLLTSGLAKTTDMLHKSSEPVTNSPANLSSTSVEILATSEVTTD
TEKTHPSSNRTVTDVGTSSSGHESTSFVLADSQTSKVTSPMVITSTMEDTSVSTSTPG
FFETSRIQTEPTSSLTLGLRKTSSSEGTSLATEMSTVLSGVPTGATAEVSRTEVTSSS
RTSISGFAQLTVSPETSTETITRLPTSSIMTESAEMMIKTQTDPPGSTPESTHTVDIS
TTPNWVETHSTVTQRFSHSEMTTLVSRSPGDMLWPSQSSVEETSSASSLLSLPATTSP
SPVSSTLVEDFPSASLPVTSLLTPGLVITTDRMGISREPGTSSTSNLSSTSHERLTTL
EDTVDTEDMQPSTHTAVTNVRTSISGHESQSSVLSDSETPKATSPMGTTYTMGETSVS
ISTSDFFETSRIQIEPTSSLTSGLRETSSSERISSATEGSTVLSEVPSGATTEVSRTE
VISSRGTSMSGPDQFTISPDISTEAITRLSTSPIMTESAESAITIETGSPGATSEGTL
TLDTSTTTFWSGTHSTASPGFSHSEMTTLMSRTPGDVPWPSLPSVEEASSVSSSLSSP
AMTSTSFFSALPESISSSPHPVTALLTLGPVKTTDMLRTSSEPETSSPPNLSSTSAEI
LATSEVTKDREKIHPSSNTPVVNVGTVIYKHLSPSSVLADLVTTKPTSPMATTSTLGN
TSVSTSTPAFPETMMTQPTSSLTSGLREISTSQETSSATERSASLSGMPTGATTKVSR
TEALSLGRTSTPGPAQSTISPEISTETITRISTPLTTTGSAEMTITPKTGHSGASSQG
TFTLDTSSRASWPGTHSAATHRSPHSGMTTPMSRGPEDVSWPSRPSVEKTSPPSSLVS
LSAVTSPSPLYSTPSESSHSSPLRVTSLFTPVMMKTTDMLDTSLEPVTTSPPSMNITS
DESLATSKATMETEAIQLSENTAVTQMGTISARQEFYSSYPGLPEPSKVTSPVVTSST
IKDIVSTTIPASSEITRIEMESTSTLTPTPRETSTSQEIHSATKPSTVPYKALTSATI
EDSMTQVMSSSRGPSPDQSTMSQDISSEVITRLSTSPIKAESTEMTITTQTGSPGATS
RGTLTLDTSTTFMSGTHSTASQGFSHSQMTALMSRTPGDVPWLSHPSVEEASSASFSL
SSPVMTSSSPVSSTLPDSIHSSSLPVTSLLTSGLVKTTELLGTSSEPETSSPPNLSST
SAEILATTEVTTDTEKLEMTNVVTSGYTHESPSSVLADSVTTKATSSMGITYPTGDTN
VLTSTPAFSDTSRIQTKSKLSLTPGLMETSISEETSSATEKSTVLSSVPTGATTEVSR
TEAISSSRTSIPGPAQSTMSSDTSMETITRISTPLTRKESTDMAITPKTGPSGATSQG
TFTLDSSSTASWPGTHSATTQRFPQSVVTTPMSRGPEDVSWPSPLSVEKNSPPSSLVS
SSSVTSPSPLYSTPSGSSHSSPVPVTSLFTSIMMKATDMLDASLEPETTSAPNMNITS
DESLATSKATTETEAIHVFENTAASHVETTSATEELYSSSPGFSEPTKVISPVVTSSS
IRDNMVSTTMPGSSGITRIEIESMSSLTPGLRETRTSQDITSSTETSTVLYKMSSGAT
```

Figure 3B (continued)

```
PEVSRTEVMPSSRTSIPGPAQSTMSLDISDEVVTRLSTSPIMTESAEITITTQTGYSL
ATSQVTLPLGTSMTFLSGTHSTMSQGLSHSEMTNLMSRGPESLSWTSPRFVETTRSSS
SLTSLPLTTSLSPVSSTLLDSSPSSPLPVTSLILPGLVKTTEVLDTSSEPKTSSSPNL
SSTSVEIPATSEIMTDTEKIHPSSNTAVAKVRTSSSVHESHSSVLADSETTITIPSMG
ITSAVDDTTVFTSNPAFSETRRIPTEPTFSLTPGFRETSTSEETTSITETSAVLYGVP
TSATTEVSMTEIMSSNRTHIPDSDQSTMSPDIITEVITRLSSSSMMSESTQMTITTQK
SSPGATAQSTLTLATTTAPLARTHSTVPPRFLHSEMTTLMSRSPENPSWKSSPFVEKT
SSSSSLLSLPVTTSPSVSSTLPQSIPSSSFSVTSLLTPGMVKTTDTSTEPGTSLSPNL
SGTSVEILAASEVTTDTEKIHPSSSMAVTNVGTTSSGHELYSSVSIHSEPSKATYPVG
TPSSMAETSISTSMPANFETTGFEAEPFSHLTSGFRKTNMSLDTSSVTPTNTPSSPGS
THLLQSSKTDFTSSAKTSSPDWPPASQYTEIPVDIITPFNASPSITESTGITSFPESR
FTMSVTESTHHLSTDLLPSAETISTGTVMPSLSEAMTSFATTGVPRAISGSGSPFSRT
ESGPGDATLSTIAESLPSSTPVPFSSSTFTTTDSSTIPALHEITSSSATPYRVDTSLG
TESSTTEGRLVMVSTLDTSSQPGRTSSTPILDTRMTESVELGTVTSAYQVPSLSTRLT
RTDGIMEHITKIPNEAAHRGTIRPVKGPQTSTSPASPKGLHTGGTKRMETTTTALKTT
TTALKTTSRATLTTSVYTPTLGTLTPLNASRQMASTILTEMMITTPYVFPDVPETTSS
LATSLGAETSTALPRTTPSVLNRESETTASLVSRSGAERSPVIQTLDVSSSEPDTTAS
WVIHPAETIPTVSKTTPNFFHSELDTVSSTATSHGADVSSAIPTNISPSELDALTPLV
TISGTDTSTTFPTLTKSPHETETRTTWLTHPAETSSTIPRTIPNFSHHESDATPSIAT
SPGAETSSAIPIMTVSPGAEDLVTSQVTSSGTDRNMTIPTLTLSPGEPKTIASLVTHP
EAQTSSAIPTSTISPAVSRLVTSMVTSLAAKTSTTNRALTNSPGEPATTVSLVTHPAQ
TSPTVPWTTSIFFHSKSDTTPSMTTSHGAESSSAVPTPTVSTEVPGVVTPLVTSSRAV
ISTTIPILTLSPGEPETTPSMATSHGEEASSAIPTPTVSPGVPGVVTSLVTSSRAVTS
TTIPILTFSLGEPETTPSMATSHGTEAGSAVPTVLPEVPGMVTSLVASSRAVTSTTLP
TLTLSPGEPETTPSMATSHGAEASSTVPTVSPEVPGVVTSLVTSSSGVNSTSIPTLIL
SPGELETTPSMATSHGAEASSAVPTPTVSPGVSGVVTPLVTSSRAVTSTTIPILTLSS
SEPETTPSMATSHGVEASSAVLTVSPEVPGMVTSLVTSSRAVTSTTIPTLTISSDEPE
TTTSLVTHSEAKMISAIPTLAVSPTVQGLVTSLVTSSGSETSAFSNLTVASSQPETID
SWVAHPGTEASSVVPTLTVSTGEPFTNISLVTHPAESSSTLPRTTSRFSHSELDTMPS
TVTSPEAESSSAISTTISPGIPGVLTSLVTSSGRDISATFPTVPESPHESEATASWVT
HPAVTSTTVPRTTPNYSHSEPDTTPSIATSPGAEATSDFPTITVSPDVPDMVTSQVTS
SGTDTSITIPTLTLSSGEPETTTSFITYSETHTSSAIPTLPVSPGASKMLTSLVISSG
TDSTTTFPTLTETPYEPETTAIQLIHPAETNTMVPKTTPKFSHSKSDTTLPVAITSPG
PEASSAVSTTTISPDMSDLVTSLVPSSGTDTSTTFPTLSETPYEPETTVTWLTHPAET
STTVSGTIPNFSHRGSDTAPSMVTSPGVDTRSGVPTTTIPPSIPGVVTSQVTSSATDT
STAIPTLTPSPGEPETTASSATHPGTQTGFTVPIRTVPSSEPDTMASWVTHPPQTSTP
VSRTTSSFSHSSPDATPVMATSPRTEASSAVLTTISPGAPEMVTSQITSSGAATSTTV
PTLTHSPGMPETTALLSTHPRTGTSKTFPASTVFPQVSETTASLTIRPGAETSTALPT
QTTSSLFTLLVTGTSRVDLSPTASPGVSAKTAPLSTHPGTETSTMIPTSTLSLGLLET
TGLLATSSSAETSTSTLTLTVSPAVSGLSSASITTDKPQTVTSWNTETSPSVTSVGPP
EFSRTVTGTTMTLIPSEMPTPPKTSHGEGVSPTTILRTTMVEATNLATTGSSPTVAKT
TTTFNTLAGSLFTPLTTPGMSTLASESVTSRTSYNHRSWISTTSSYNRRYWTPATSTP
VTSTFSPGISTSSIPSSTAATVPFMVPFTLNFTITNLQYEEDMRHPGSRKFNATEREL
QGLLKPLFRNSSLEYLYSGCRLASLRPEKDSSAMAVDAICTHRPDPEDLGLDRERLYW
ELSNLTNGIQELGPYTLDRNSLYVNGFTHRSSMPTTSTPGTSTVDVGTSGTPSSSPSP
TAAGPLLMPFTLNFTITNLQYEEDMRRTGSRKFNTMESVLQGLLKPLFKNTSVGPLYS
GCRLTLLRPEKDGAATGVDAICTHRLDPKSPGLNREQLYWELSKLTNDIEELGPYTLD
RNSLYVNGFTHQSSVSTTSTPGTSTVDLRTSGTPSSLSSPTIMAAGPLLVPFTLNFTI
TNLQYGEDMGHPGSRKFNTTERVLQGLLGPIFKNTSVGPLYSGCRLTSLRSEKDGAAT
GVDAICIHHLDPKSPGLNRERLYWELSQLTNGIKELGPYTLDRNSLYVNGFTHRTSVP
TTSTPGTSTVDLGTSGTPFSLPSPATAGPLLVLFTLNFTITNLKYEEDMHRPGSRKFN
TTERVLQTLLGPMFKNTSVGLLYSGCRLTLLRSEKDGAATGVDAICTHRLDPKSPGLD
REQLYWELSQLTNGIKELGPYTLDRNSLYVNGFTHWIPVPTSSTPGTSTVDLGSGTPS
SLPSPTAAGPLLVPFTLNFTITNLQYEEDMHHPGSRKFNTTERVLQGLLGPMFKNTSV
GLLYSGCRLTLLRSEKDGAATGVDAICTHRLDPKSPGVDREQLYWELSQLTNGIKELG
PYTLDRNSLYVNGFTHQTSAPNTSTPGTSTVDLGTSGTPSSLPSPTSAGPLLVPFTLN
FTITNLQYEEDMRHPGSRKFNTTERVLQGLLKPLFKSTSVGPLYSGCRLTLLRSEKDG
AATGVDAICTHRLDPKSPGVDREQLYWELSQLTNGIKELGPYTLDRNSLYVNGFTHQT
SAPNTSTPGTSTVDLGTSGTPSSLPSPTSAGPLLVPFTLNFTITNLQYEEDMHHPGSR
```

Figure 3B (continued)

KFNTTERVLQGLLGPMFKNTSVGLLYSGCRLTLLRPEKNGAATGMDAICSHRLDPKSP
GLNREQLYWELSQLTHGIKELGPYTLDRNSLYVNGFTHRSSVAPTSTPGTSTVDLGTS
GTPSSLPSPTTAVPLLVPFTLNFTITNLQYGEDMRHPGSRKFNTTERVLQGLLGPLFK
NSSVGPLYSGCRLISLRSEKDGAATGVDAICTHHLNPQSPGLDREQLYWQLSQMTNGI
KELGPYTLDRNSLYVNGFTHRSSGLTTSTPWTSTVDLGTSGTPSPVPSPTTAGPLLVP
FTLNFTITNLQYEEDMHRPGSRKFNTTERVLQGLLSPIFKNSSVGPLYSGCRLTSLRP
EKDGAATGMDAVCLYHPNPKRPGLDREQLYWELSQLTHNITELGPYSLDRDSLYVNGF
THQNSVPTTSTPGTSTVYWATTGTPSSFPGHTEPGPLLIPFTFNFTITNLHYEENMQH
PGSRKFNTTERVLQGLLKPLFKNTSVGPLYSGCRLTSLRPEKDGAATGMDAVCLYHPN
PKRPGLDREQLYWELSQLTHNITELGPYSLDRDSLYVNGFTHQNSVPTTSTPGTSTVY
WATTGTPSSFPGHTEPGPLLIPFTFNFTITNLHYEENMQHPGSRKFNTTERVLQGLLK
PLFKNTSVGPLYSGCRLTLLRPEKHEAATGVDTICTHRVDPIGPGLDRERLYWELSQL
TNSITELGPYTLDRDSLYVNGFNPRSSVPTTSTPGTSTVHLATSGTPSSLPGHTAPVP
LLIPFTLNFTITNLHYEENMQHPGSRKFNTTERVLQGLLKPLFKNTSVGPLYSGCRLT
LLRPEKHEAATGVDTICTHRVDPIGPGLXXEXLYWELSXLTXXIXELGPYTLDRXSLY
VNGFTHXXSXPTTSTPGTSTVXXGTSGTPSSXPXXTSAGPLLVPFTLNFTITNLQYEE
DMHHPGSRKFNTTERVLQGLLGPMFKNTSVGLLYSGCRLTLLRPEKNGAATGMDAICS
HRLDPKSPGLDREQLYWELSQLTHGIKELGPYTLDRNSLYVNGFTHRSSVAPTSTPGT
STVDLGTSGTPSSLPSPTTAVPLLVPFTLNFTITNLQYGEDMRHPGSRKFNTTERVLQ
GLLGPLFKNSSVGPLYSGCRLISLRSEKDGAATGVDAICTHHLNPQSPGLDREQLYWQ
LSQMTNGIKELGPYTLDRNSLYVNGFTHRSSGLTTSTPWTSTVDLGTSGTPSPVPSPT
TAGPLLVPFTLNFTITNLQYEEDMHRPGSRKFNATERVLQGLLSPIFKNSSVGPLYSG
CRLTSLRPEKDGAATGMDAVCLYHPNPKRPGLDREQLYWELSQLTHNITELGPYSLDR
DSLYVNGFTHQSSMTTTRTPDTSTMHLATSRTPASLSGPTTASPLLVLFTINCTITNL
QYEEDMRRTGSRKFNTMESVLQGLLKPLFKNTSVGPLYSGCRLTLLRPKKDGAATGVD
AICTHRLDPKSPGLNREQLYWELSKLTNDIEELGPYTLDRNSLYVNGFTHQSSVSTTS
TPGTSTVDLRTSGTPSSLSSPTIMXXXPLLXPFTXNXTITNLXXXXXMXXPGSRKFNT
TERVLQGLLRPLFKNTSVSSLYSGCRLTLLRPEKDGAATRVDAACTYRPDPKSPGLDR
EQLYWELSQLTHSITELGPYTLDRVSLYVNGFNPRSSVPTTSTPGTSTVHLATSGTPS
SLPGHTXXXPLLXPFTXNXTITNLXXXXXMXXPGSRKFNTTERVLQGLLKPLFRNSSL
EYLYSGCRLASLRPEKDSSAMAVDAICTHRPDPEDLGLDRERLYWELSNLTNGIQELG
PYTLDRNSLYVNGFTHRSSGLTTSTPWTSTVDLGTSGTPSPVPSPTTAGPLLVPFTLN
FTITNLQYEEDMHRPGSRRFNTTERVLQGLLTPLFKNTSVGPLYSGCRLTLLRPEKQE
AATGVDTICTHRVDPIGPGLDRERLYWELSQLTNSITELGPYTLDRDSLYVNGFNPWS
SVPTTSTPGTSTVHLATSGTPSSLPGHTAPVPLLIPFTLNFTITDLHYEENMQHPGSR
KFNTTERVLQGLLKPLFKSTSVGPLYSGCRLTLLRPEKHGAATGVDAICTLRLDPTGP
GLDRERLYWELSQLTNSVTELGPYTLDRDSLYVNGFTHRSSVPTTSIPGTSAVHLETS
GTPASLPGHTAPGPLLVPFTLNFTITNLQYEEDMRHPGSRKFSTTERVLQGLLKPLFK
NTSVSSLYSGCRLTLLRPEKDGAATRVDAVCTHRPDPKSPGLDRERLYWKLSQLTHGI
TELGPYTLDRHSLYVNGFTHQSSMTTTRTPDTSTMHLATSRTPASLSGPTTASPLLVL
FTINFTITNLRYEENMHHPGSRKFNTTERVLQGLLRPVFKNTSVGPLYSGCRLTTLRP
KKDGAATKVDAICTYRPDPKSPGLDREQLYWELSQLTHSITELGPYTQDRDSLYVNGF
THRSSVPTTSIPGTSAVHLETSGTPASLPGHTAPGPLLVPFTLNFTITNLQYEEDMRH
PGSRKFNTTERVLQGLLKPLFKSTSVGPLYSGCRLTLLRPEKRGAATGVDTICTHRLD
PLNPGLDREQLYWELSKLTRGIIELGPYLLDRGSLYVNGFTHRTSVPTTSTPGTSTVD
LGTSGTPFSLPSPAXXXPLLXPFTXNXTITNLXXXXXMXXPGSRKFNTTERVLQTLLG
PMFKNTSVGLLYSGCRLTLLRSEKDGAATGVDAICTHRLDPKSPGVDREQLYWELSQL
TNGIKELGPYTLDRNSLYVNGFTHWIPVPTSSTPGTSTVDLGSGTPSSLPSPTTAGPL
LVPFTLNFTITNLKYEEDMHCPGSRKFNTTERVLQSLLGPMFKNTSVGPLYSGCRLTL
LRSEKDGAATGVDAICTHRLDPKSPGVDREQLYWELSQLTNGIKELGPYTLDRNSLYV
NGFTHQTSAPNTSTPGTSTVDLGTSGTPSSLPSPTXXXPLLXPFTXNXTITNLXXXXX
MXXPGSRKFNTTEXVLQGLLXPXFKNXSVGXLYSGCRLTXLRXEKXGAATGXDAICXH
XXXPKXPGLXXEXLYWELSXLTXXIXELGPYTLDRXSLYVNGFTHWIPVPTSSTPGTS
TVDLGSGTPSSLPSPTTAGPLLVPFTLNFTITNLKYEEDMHCPGSRKFNTTERVLQSL
LGPMFKNTSVGPLYSGCRLTSLRSEKDGAATGVDAICTHRVDPKSPGVDREQLYWELS
QLTNGIKELGPYTLDRNSLYVNGFTHQTSAPNTSTPGTSTVXXGTSGTPSSXPXXTSA
GPLLVPFTLNFTITNLQYEEDMHHPGSRKFNTTERVLQGLLGPMFKNTSVGLLYSGCR

Figure 3B (continued)

LTLLRPEKNGATTGMDAICTHRLDPKSPGLXXEXLYWELSXLTXXIXELGPYTLDRXS
LYVNGFTHXXSXPTTSTPGTSTVXXGTSGTPSSXPXXTXXXPLLXPFTXNXTITNLXX
XXXMXXPGSRKFNTTERVLQGLLKPLFRNSSLEYLYSGCRLASLRPEKDSSAMAVDAI
CTHRPDPEDLGLDRERLYWELSNLTNGIQELGPYTLDRNSLYVNGFTHRSSMPTTSTP
GTSTVDVGTSGTPSSSPSPTTAGPLLIPFTLNFTITNLQYGEDMGHPGSRKFNTTERV
LQGLLGPIFKNTSVGPLYSGCRLTSLRSEKDGAATGVDAICIHHLDPKSPGLNRERLY
WELSQLTNGIKELGPYTLDRNSLYVNGFTHRTSVPTTSTPGTSTVDLGTSGTPFSLPS
PATAGPLLVLFTLNFTITNLKYEEDMHRPGSRKFNTTERVLQTLLGPMFKNTSVGLLY
SGCRLTLLRSEKDGAATGVDAICTHRLDPKSPGLXXEXLYWELSXLTXXIXELGPYTL
DRXSLYVNGFTHXXSXPTTSTPGTSTVXXGTSGTPSSXPXXTXXXPLLXPFTXNXTIT
NLXXXXXMXXPGSRKFNTTERVLQGLLRPVFKNTSVGPLYSGCRLTLLRPKKDGAATK
VDAICTYRPDPKSPGLDREQLYWELSQLTHSITELGPYTQDRDSLYVNGFTHRSSVPT
TSIPGTSAVHLETTGTPSSFPGHTEPGPLLIPFTFNFTITNLRYEENMQHPGSRKFNT
TERVLQGLLTPLFKNTSVGPLYSGCRLTLLRPEKQEAATGVDTICTHRVDPIGPGLDR
ERLYWELSQLTNSITELGPYTLDRDSLYVDGFNPWSSVPTTSTPGTSTVHLATSGTPS
PLPGHTAPVPLLIPFTLNFTITDLHYEENMQHPGSRKFNTTERVLQGLLKPLFKSTSV
GPLYSGCRLTLLRPEKHGAATGVDAICTLRLDPTGPGLDRERLYWELSQLTNSITELG
PYTLDRDSLYVNGFNPWSSVPTTSTPGTSTVHLATSGTPSSLPGHTTAGPLLVPFTLN
FTITNLKYEEDMHCPGSRKFNTTERVLQSLHGPMFKNTSVGPLYSGCRLTLLRSEKDG
AATGVDAICTHRLDPKSPGLXXEXLYWELSXLTXXIXELGPYTLDRXSLYVNGFTHXX
SXPTTSTPGTSTVXXGTSGTPSSXPXXTXXXPLLXPFTXNXTITNLXXXXXMXXPGSR
KFNTTEXVLQGLLXPXFKNXSVGXLYSGCRLTXLRXEKXGAATGXDAICXHXXXPKXP
GLXXEXLYWELSXLTNSITELGPYTLDRDSLYVNGFTHRSSMPTTSIPGTSAVHLETS
GTPASLPGHTAPGPLLVPFTLNFTITNLQYEEDMRHPGSRKFNTTERVLQGLLKPLFK
STSVGPLYSGCRLTLLRPEKRGAATGVDTICTHRLDPLNPGLXXEXLYWELSXLTXXI
XELGPYTLDRXSLYVNGFTHXXSXPTTSTPGTSTVXXGTSGTPSSXPXXTXXXPLLXP
FTXNXTITNLXXXXXMXXPGSRKFNTTEXVLQGLLXPXFKNXSVGXLYSGCRLTXLRX
EKXGAATGXDAICXHXXXPKXPGLXXEXLYWELSXLTXXIXELGPYTLDRXSLYVNGF
HPRSSVPTTSTPGTSTVHLATSGTPSSLPGHTAPVPLLIPFTLNFTITNLHYEENMQH
PGSRKFNTTERVLQGLLGPMFKNTSVGLLYSGCRLTLLRPEKNGAATGMDAICSHRLD
PKSPGLXXEXLYWELSXLTXXIXELGPYTLDRXSLYVNGFTHXXSXPTTSTPGTSTVX
XGTSGTPSSXPXXTXXXPLLXPFTXNXTITNLXXXXXMXXPGSRKFNTTEXVLQGLLX
PXFKNXSVGXLYSGCRLTXLRXEKXGAATGXDAICXHXXXPKXPGLXXEXLYWELSXL
TXXIXELGPYTLDRXSLYVNGFTHQNSVPTTSTPGTSTVYWATTGTPSSFPGHTEPGP
LLIPFTFNFTITNLHYEENMQHPGSRKFNTTERVLQGLLTPLFKNTSVGPLYSGCRLT
LLRPEKQEAATGVDTICTHRVDPIGPGLXXEXLYWELSXLTXXIXELGPYTLDRXSLY
VNGFTHXXSXPTTSTPGTSTVXXGTSGTPSSXPXXTXXXPLLXPFTXNXTITNLXXXX
XMXXPGSRKFNTTEXVLQGLLXPXFKNXSVGXLYSGCRLTXLRXEKXGAATGXDAICX
HXXXPKXPGLXXEXLYWELSXLTXXIXELGPYTLDRXSLYVNGFTHRSSVPTTSSPGT
STVHLATSGTPSSLPGHTAPVPLLIPFTLNFTITNLHYEENMQHPGSRKFNTTERVLQ
GLLKPLFKSTSVGPLYSGCRLTLLRPEKHGAATGVDAICTLRLDPTGPGLXXEXLYWE
LSXLTXXIXELGPYTLDRXSLYVNGFTHXXSXPTTSTPGTSTVXXGTSGTPSSXPXXT
XXXPLLXPFTXNXTITNLXXXXXMXXPGSRKFNTTEXVLQGLLXPXFKNXSVGXLYSG
CRLTXLRXEKXGAATGXDAICXHXXXPKXPGLXXEXLYWELSXLTXXIXELGPYTLDR
XSLYVNGFTHRTSVPTTSTPGTSTVHLATSGTPSSLPGHTAPVPLLIPFTLNFTITNL
QYEEDMHRPGSRKFNTTERVLQGLLSPIFKNSSVGPLYSGCRLTSLRPEKDGAATGMD
AVCLYHPNPKRPGLDREQLYCELSQLTHNITELGPYSLDRDSLYVNGFTHQNSVPTTS
TPGTSTVYWATTGTPSSFPGHTXXXPLLXPFTXNXTITNLXXXXXMXXPGSRKFNTTE
XVLQGLLXPXFKNXSVGXLYSGCRLTXLRXEKXGAATGXDAICXHXXXPKXPGLXXEX
LYWELSXLTXXIXELGPYTLDRXSLYVNGFTHWSSGLTTSTPWTSTVDLGTSGTPSPV
PSPTTAGPLLVPFTLNFTITNLQYEEDMHRPGSRKFNATERVLQGLLSPIFKNTSVGP
LYSGCRLTLLRPEKQEAATGVDTICTHRVDPIGPGLXXEXLYWELSXLTXXIXELGPY
TLDRXSLYVNGFTHXXSXPTTSTPGTSTVXXGTSGTPSSXPXXTXXXPLLXPFTXNXT
ITNLXXXXXMXXPGSRKFNTTEXVLQGLLXPXFKNXSVGXLYSGCRLTXLRXEKXGAA
TGXDAICXHXXXPKXPGLXXEXLYWELSXLTXXIXELGPYTLDRXSLYVNGFTHRSFG
LTTSTPWTSTVDLGTSGTPSPVPSPTTAGPLLVPFTLNFTITNLQYEEDMHRPGSRKF

Figure 3B (continued)

NTTERVLQGLLTPLFRNTSVSSLYSGCRLTLLRPEKDGAATRVDAVCTHRPDPKSPGL
XXEXLYWELSXLTXXIXELGPYTLDRXSLYVNGFTHXXSXPTTSTPGTSTVXXGTSGT
PSSXPXXTXXXPLLXPFTXNXTITNLXXXXXMXXPGSRKFNTTEXVLQGLLXPXFKNX
SVGXLYSGCRLTXLRXEKXGAATGXDAICXHXXXPKXPGLXXEXLYWELSXLTXXIXE
LGPYTLDRXSLYVNGFTHWIPVPTSSTPGTSTVDLGSGTPSSLPSPTTAGPLLVPFTL
NFTITNLQYGEDMGHPGSRKFNTTERVLQGLLGPIFKNTSVGPLYSGCRLTSLRSEKD
GAATGVDAICIHHLDPKSPGLXXEXLYWELSXLTXXIXELGPYTLDRXSLYVNGFTHX
XSXPTTSTPGTSTVXXGTSGTPSSXPXXTXXXPLLXPFTXNXTITNLXXXXXMXXPGS
RKFNTTEXVLQGLLXPXFKNXSVGXLYSGCRLTXLRXEKXGAATGXDAICXHXXXPKX
PGLXXEXLYWELSXLTXXIXELGPYTLDRXSLYVNGFTHQTFAPNTSTPGTSTVDLGT
SGTPSSLPSPTSAGPLLVPFTLNFTITNLQYEEDMHHPGSRKFNTTERVLQGLLGPMF
KNTSVGLLYSGCRLTLLRPEKNGAATRVDAVCTHRPDPKSPGLXXEXLYWELSXLTXX
IXELGPYTLDRXSLYVNGFTHXXSXPTTSTPGTSTVXXGTSGTPSSXPXXTAPVPLLI
PFTLNFTITNLHYEENMQHPGSRKFNTTERVLQGLLKPLFKSTSVGPLYSGCRLTLLR
PEKHGAATGVDAICTLRLDPTGPGLDRERLYWELSQLTNSVTELGPYTLDRDSLYVNG
FTQRSSVPTTSIPGTSAVHLETSGTPASLPGHTAPGPLLVPFTLNFTITNLQYEVDMR
HPGSRKFNTTERVLQGLLKPLFKSTSVGPLYSGCRLTLLRPEKRGAATGVDTICTHRL
DPLNPGLDREQLYWELSKLTRGIIELGPYLLDRGSLYVNGFTHRNFVPITSTPGTSTV
HLGTSETPSSLPRPIVPGPLLVPFTLNFTITNLQYEEAMRHPGSRKFNTTERVLQGLL
RPLFKNTSIGPLYSSCRLTLLRPEKDKAATRVDAICTHHPDPQSPGLNREQLYWELSQ
LTHGITELGPYTLDRDSLYVDGFTHWSPIPTTSTPGTSIVNLGTSGIPPSLPETTXXX
PLLXPFTXNXTITNLXXXXXMXXPGSRKFNTTERVLQGLLKPLFKSTSVGPLYSGCRL
TLLRPEKDGVATRVDAICTHRPDPKIPGLDRQQLYWELSQLTHSITELGPYTLDRDSL
YVNGFTQRSSVPTTSTPGTFTVQPETSETPSSLPGPTATGPVLLPFTLNFTITNLQYE
EDMHRPGSRKFNTTERVLQGLLMPLFKNTSVSSLYSGCRLTLLRPEKDGAATRVDAVC
THRPDPKSPGLDRERLYWKLSQLTHGITELGPYTLDRHSLYVNGFTHQSSMTTTRTPD
TSTMHLATSRTPASLSGPTTASPLLVLFTINFTITNLRYEENMHHPGSRKFNTTERVL
QGLLRPVFKNTSVGPLYSGCRLTLLRPKKDGAATKVDAICTYRPDPKSPGLDREQLYW
ELSQLTHSITELGPYTLDRDSLYVNGFTQRSSVPTTSIPGTPTVDLGTSGTPVSKPGP
SAASPLLVLFTLNFTITNLRYEENMQHPGSRKFNTTERVLQGLLRSLFKSTSVGPLYS
GCRLTLLRPEKDGTATGVDAICTHHPDPKSPRLDREQLYWELSQLTHNITELGHYALD
NDSLFVNGFTHRSSVSTTSTPGTPTVYLGASKTPASIFGPSAASHLLILFTLNFTITN
LRYEENMWPGSRKFNTTERVLQGLLRPLFKNTSVGPLYSGSRLTLLRPEKDGEATGVD
AICTHRPDPTGPGLDREQLYLELSQLTHSITELGPYTLDRDSLYVNGFTHRSSVPTTS
TGVVSEEPFTLNFTINNLRYMADMGQPGSLKFNITDNVMKHLLSPLFQRSSLGARYTG
CRVIALRSVKNGAETRVDLLCTYLQPLSGPGLPIKQVFHELSQQTHGITRLGPYSLDK
DSLYLNGYNEPGLDEPPTTPKPATTFLPPLSEATTAMGYHLKTLTLNFTISNLQYSPD
MGKGSATFNSTEGVLQHLLRPLFQKSSMGPFYLGCQLISLRPEKDGAATGVDTTCTYH
PDPVGPGLDIQQLYWELSQLTHGVTQLGFYVLDRDSLFINGYAPQNLSIRGEYQINFH
IVNWNLSNPDPTSSEYITLLRDIQDKVTTLYKGSQLHDTFRFCLVTNLTMDSVLVTVK
ALFSSNLDPSLVEQVFLDKTLNASFHWLGSTYQLVDIHVTEMESSVYQPTSSSSTQHF
YLNFTITNLPYSQDKAQPGTTNYQRNKRNIEDALNQLFRNSSIKSYFSDCQVSTFRSV
PNRHHTGVDSLCNFSPLARRVDRVAIYEEFLRMTRNGTQLQNFTLDRSSVLVDGYSPN
RNEPLTGNSDLPFWAVILIGLAGLLGLITCLICGVLVTTRRRKKEGEYNVQQQCPGYY
QSHLDLEDLQ

Figure 3B (Continued)

Nucleic acid and polypeptide sequences of IL-18

Nucleic acid sequence (SEQ ID No:3)

```
   1 attctctccc cagcttgctg agccctttgc tccctggcg actgcctgga cagtcagcaa
  61 ggaattgtct cccagtgcat tttgccctcc tggctgccaa ctctggctgc taaagcggct
 121 gccacctgct gcagtctaca cagcttcggg aagaggaaag gaacctcaga ccttccagat
 181 cgcttcctct cgcaacaaac tatttgtcgc aggaataaag atggctgctg aaccagtaga
 241 agacaattgc atcaactttg tggcaatgaa atttattgac aatacgcttt actttatagc
 301 tgaagatgat gaaaacctgg aatcagatta ctttggcaag cttgaatcta aattatcagt
 361 cataagaaat ttgaatgacc aagttctctt cattgaccaa ggaaatcggc ctctatttga
 421 agatatgact gattctgact gtagagataa tgcaccccgg accatattta ttataagtat
 481 gtataaagat agccagccta gaggtatggc tgtaactatc tctgtgaagt gtgagaaaat
 541 ttcaactctc tcctgtgaga acaaaattat ttcctttaag gaaatgaatc ctcctgataa
 601 catcaaggat acaaaaagtg acatcatatt ctttcagaga gtgtcccag gacatgataa
 661 taagatgcaa tttgaatctt catcatacga aggatacttt ctagcttgtg aaaaagagag
 721 agaccttttt aaactcattt tgaaaaaaga ggatgaattg ggggatagat ctataatgtt
 781 cactgttcaa aacgaagact agctattaaa atttcatgcc gggcgcagtg gctcacgcct
 841 gtaatcccag ccctttggga ggctgaggcg ggcagatcac cagaggtcag gtgttcaaga
 901 ccagcctgac caacatggtg aaacctcatc tctactaaaa atacaaaaaa ttagctgagt
 961 gtagtgacgc atgccctcaa tcccagctac tcaagaggct gaggcaggag aatcacttgc
1021 actccggagg tagaggttgt ggtgagccga gattgcacca ttgcgctcta gcctgggcaa
1081 caacagcaaa actccatctc aaaaaataaa ataaataaat aaacaaataa aaaattcata
1141 atgtg
```

Figure 4A

Polypeptide sequence (SEQ ID No:4)

MAAEPVEDNCINFVAMKFIDNTLYFIAEDDENLESDYFGKLESKLSVIRNLNDQVLFIDQGNRPLFEDM
TDSDCRDNAPRTIFIISMYKDSQPRGMAVTISVKCEKISTLSCENKIISFKEMNPPDNIKDTKSDIIFF
QRSVPGHDNKMQFESSSYEGYFLACEKERDLFKLILKKEDELGDRSIMFTVQNED

Figure 4B

Nucleic acid and polypeptide sequences of FGF-2

Nucleic acid sequence (SEQ ID No:5)

```
   1 cggccccaga aacccgagc gagtagggg cggcgcgcag gagggaggag aactgggggc
  61 gcgggaggct ggtgggtgtc gggggtggag atgtagaaga tgtgacgccg cggcccggcg
 121 ggtgccagat tagcggacgc gctgcccgcg gttgcaacgg gatcccgggc gctgcagctt
 181 gggaggcggc tctccccagg cggcgtccgc ggagacaccc atccgtgaac cccaggtccc
 241 gggccgccgg ctcgccgcgc accaggggcc ggcggacaga agagcggccg agcggctcga
 301 ggctggggga ccgcgggcgc ggccgcgcgc tgccgggcgg gaggctgggg ggccggggcc
 361 ggggccgtgc cccggagcgg gtcggaggcc ggggccgggg ccggggacg gcggctcccc
 421 gcgcggctcc agcggctcgg ggatcccggc cgggccccgc agggaccatg gcagccggga
 481 gcatcaccac gctgcccgcc ttgcccgagg atggcggcag cggcgccttc ccgcccggcc
 541 acttcaagga ccccaagcgg ctgtactgca aaaacggggg cttcttcctg cgcatccacc
 601 ccgacggccg agttgacggg tccgggaga gagcgaccc tcacatcaag ctacaacttc
 661 aagcagaaga gagaggagtt gtgtctatca aggagtgtg tgctaaccgt tacctggcta
 721 tgaaggaaga tggaagatta ctggcttcta aatgtgttac ggatgagtgt ttcttttttg
 781 aacgattgga atctaataac tacaatactt accggtcaag gaaatacacc agttggtatg
 841 tggcactgaa acgaactggg cagtataaac ttggatccaa aacaggacct gggcagaaag
 901 ctatactttt tcttccaatg tctgctaaga gctgatttta atggccacat ctaatctcat
 961 ttcacatgaa agaagaagta tattttagaa atttgttaat gagagtaaaa gaaaataaat
1021 gtgtatagct cagtttggat aattggtcaa acaattttt atccagtagt aaaatatgta
1081 accattgtcc cagtaaagaa aaataacaaa agttgtaaaa tgtatattct ccctttata
1141 ttgcatctgc tgttacccag tgaagcttac ctagagcaat gatcttttc acgcatttgc
1201 tttattcgaa aagaggcttt taaatgtgc atgtttagaa acaaaatttc ttcatggaaa
1261 tcatatacat tagaaaatca cagtcagatg tttaatcaat ccaaaatgtc cactatttct
1321 tatgtcattc gttagtctac atgtttctaa acatataaat gtgaatttaa tcaattcctt
1381 tcatagtttt ataattctct ggcagttcct tatgatagag tttataaaac agtcctgtgt
1441 aaactgctgg aagttcttcc acagtcaggt caattttgtc aaacccttct ctgtacccat
1501 acagcagcag cctagcaact ctgctggtga tgggagttgt attttcagtc ttcgccaggt
1561 cattgagatc catccactca catcttaagc attcttcctg gcaaaaattt atggtgaatg
1621 aatatggctt taggcggcag atgatataca tatctgactt cccaaaagct ccaggatttg
1681 tgtgctgttg ccgaatactc aggacggacc tgaattctga ttttatacca gtctcttcaa
1741 aaacttctcg aaccgctgtg tctcctacgt aaaaaaagag atgtacaat caataataat
1801 tacacttta gaaactgtat catcaaagat tttcagttaa agtagcatta tgtaaaggct
1861 caaaacatta ccctaacaaa gtaaagtttt caatacaaat tctttgcctt gtggatatca
1921 agaaatccca aaatatttc ttaccactgt aaattcaaga agcttttgaa atgctgaata
1981 tttctttggc tgctacttgg aggcttatct acctgtacat ttttgggtc agctcttttt
2041 aacttcttgc tgctcttttt cccaaaaggt aaaaatatag attgaaaagt taaacattt
2101 tgcatggctg cagttccttt gtttcttgag ataagattcc aaagaactta gattcatttc
2161 ttcaacaccg aaatgctgga ggtgtttgat cagttttcaa gaaacttgga atataaataa
2221 ttttataatt caacaaaggt tttcacattt tataaggttg atttttcaat taaatgcaaa
2281 tttgtgtggc aggattttta ttgccattaa catatttttg tggctgcttt ttctacacat
2341 ccagatggtc cctctaactg gctttctct aattttgtga tgttctgtca ttgtctccca
2401 aagtatttag gagaagccct ttaaaaagct gccttcctct accactttgc tggaaagctt
2461 cacaattgtc acagacaaag attttttgttc caatactcgt tttgcctcta ttttttcttgt
2521 ttgtcaaata gtaaatgata tttgcccttg cagtaattct actggtgaaa aacatgcaaa
2581 gaagaggaag tcacagaaac atgtctcaat tcccatgtgc tgtgactgta gactgtctta
2641 ccatagactg tcttacccat ccctggata tgctcttgtt ttttccctct aatagctatg
2701 gaaagatgca tagaaagagt ataatgtttt aaaacataag gcattcatct gccattttc
2761 aattacatgc tgacttccct tacaattgag atttgcccat aggttaaaca tggttagaaa
2821 caactgaaag cataaaagaa aaatctaggc cgggtgcagt ggctcatgcc tatattccct
2881 gcactttggg aggccaaagc aggaggatcg cttgagccca ggagttcaag accaacctgg
2941 tgaaccccg tctctacaaa aaacacaaa aatagccag gcatggtggc gtgtacatgt
```

Figure 5A

```
3001 ggtctcagat acttgggagg ctgaggtggg agggttgatc acttgaggct gagaggtcaa
3061 ggttgcagtg agccataatc gtgccactgc agtccagcct aggcaacaga gtgagacttt
3121 gtctcaaaaa aagagaaatt ttccttaata agaaaagtaa ttttactct gatgtgcaat
3181 acatttgtta ttaaatttat tatttaagat ggtagcacta gtcttaaatt gtataaaata
3241 tcccctaaca tgtttaaatg tccatttta ttcattatgc tttgaaaaat aattatgggg
3301 aaatacatgt ttgttattaa atttattatt aaagatagta gcactagtct taaatttgat
3361 ataacatctc ctaacttgtt taaatgtcca tttttattct ttatgcttga aaataaatta
3421 tggggatcct atttagctct tagtaccact aatcaaaagt tcggcatgta gctcatgatc
3481 tatgctgttt ctatgtcgtg gaagcaccgg atgggggtag tgagcaaatc tgccctgctc
3541 agcagtcacc atagcagctg actgaaaatc agcactgcct gagtagtttt gatcagttta
3601 acttgaatca ctaactgact gaaaattgaa tggcaaata agtgctttg tctccagagt
3661 atgcgggaga cccttccacc tcaagatgga tatttcttcc ccaaggattt caagatgaat
3721 tgaaattttt aatcaagata gtgtgcttta ttctgttgta ttttttatta tttaatata
3781 ctgtaagcca aactgaaata acatttgctg ttttataggt ttgaagaaca taggaaaaac
3841 taagaggttt tgtttttatt tttgctgatg aagagatatg tttaaatatg ttgtattgtt
3901 ttgtttagtt acaggacaat aatgaaatgg agtttatatt tgttattct attttgttat
3961 atttaataat agaattagat tgaaataaaa tataatggga ataatctgc agaatgtggg
4021 tttcctggtg tttcctctga ctctagtgca ctgatgatct ctgataaggc tcagctgctt
4081 tatagttctc tggctaatgc agcagatact cttcctgcca gtggtaatac gattttttaa
4141 gaaggcagtt tgtcaatttt aatcttgtgg ataccttat actcttaggg tattatttta
4201 tacaaaagcc ttgaggattg cattctattt tctatatgac cctcttgata tttaaaaaac
4261 actatggata acaattcttc atttacctag tattatgaaa gaatgaagga gttcaaacaa
4321 atgtgtttcc cagttaacta gggtttactg tttgagccaa tataaatgtt taactgttg
4381 tgatggcagt attcctaaag tacattgcat gttttcctaa atacagagtt taaataattt
4441 cagtaattct tagatgattc agcttcatca ttaagaatat cttttgtttt atgttgagtt
4501 agaaatgcct tcatatagac atagtctttc agacctctac tgtcagtttt catttctagc
4561 tgctttcagg gttttatgaa ttttcaggca aagctttaat ttatactaag cttaggaagt
4621 atggctaatg ccaacggcag ttttttttctt cttaattcca catgactgag gcatatatga
4681 tctctgggta ggtgagttgt tgtgacaacc acaagcactt tttttttttt taaagaaaaa
4741 aaggtagtga attttaatc atctggactt taagaaggat tctggagtat acttaggcct
4801 gaaattatat atatttggct tggaaatgtg ttttttcttca attcactcta caagtaagta
4861 cagctgaaat tcagaggacc cataagagtt cacatgaaaa aaatcaattc atttgaaaag
4921 gcaagatgca ggagagagga agccttgcaa acctgcagac tgctttttgc ccaatataga
4981 ttgggtaagg ctgcaaaaca taagcttaat tagctcacat gctctgctct cacgtggcac
5041 cagtggatag tgtgagagaa ttaggctgta gaacaaatgg ccttctcttt cagcattcac
5101 accactacaa aatcatcttt tatatcaaca gaagaataag cataaactaa gcaaaggtc
5161 aataagtacc tgaaaccaag attggctaga gatatatctt aatgcaatcc attttctgat
5221 ggattgttac gagttggcta tataatgtat gtatggtatt ttgatttgtg taaaagtttt
5281 aaaaatcaag ctttaagtac atggacattt ttaaataaaa tatttaaaga caatttagaa
5341 aattgcctta atatcattgt tggctaaata gaatagggga catgcatatt aaggaaaagg
5401 tcatggagaa ataatattgg tatcaaacaa atacattgat ttgtcatgat acacattgaa
5461 tttgatccaa tagtttaagg aataggtagg aaaatttggt ttctattttt cgatttcctg
5521 taaatcagtg acataaataa ttcttagctt attttatatt tccttgtctt aaatactgag
5581 ctcagtaagt tgtgttaggg gattatttct cagttgagac tttcttatat gacattttac
5641 tatgttttga cttcctgact attaaaaata aatagtagaa acaattttca taaagtgaag
5701 aattatataa tcactgcttt ataactgact ttattatatt tatttcaaag ttcatttaaa
5761 ggctactatt catcctctgt gatggaatgg tcaggaattt gttttctcat agtttaattc
5821 caacaacaat attagtcgta tccaaaataa cctttaatgc taaactttac tgatgtatat
5881 ccaaagcttc tccttttcag acagattaat ccagaagcag tcataaacag aagaataggt
5941 ggtatgttcc taatgatatt atttctacta atggaataaa ctgtaatatt agaaattatg
6001 ctgctaatta tatcagctct gaggtaattt ctgaaatgtt cagactcagt cggaacaaat
6061 tggaaaattt aaatttttat tcttagctat aaagcaagaa agtaaacaca ttaatttcct
6121 caacattttt aagccaatta aaaatataaa agatacacac caatatcttc ttcaggctct
6181 gacaggcctc ctggaaactt ccacatattt ttcaactgca gtataaagtc agaaaataaa
6241 gttaacataa ctttcactaa cacacacata tgtagatttc acaaaatcca cctataattg
6301 gtcaaagtgg ttgagaatat atttttagt aattgcatgc aaaattttc tagcttccat
6361 ccttctccc tcgtttcttc ttttttggg ggagctggta actgatgaaa tcttttccca
6421 ccttttctct tcaggaaata taagtggttt tgtttggtta acgtgataca ttctgtatga
6481 atgaaacatt ggagggaaac atctactgaa tttctgtaat ttaaaatatt ttgctgctag
6541 ttaactatga acagatagaa gaatcttaca gatgctgcta taaataagta gaaaatataa
6601 atttcatcac taaaatatgc tattttaaaa tctatttcct atattgtatt tctaatcaga
6661 tgtattactc ttattatttc tattgtatgt gttaatgatt ttatgtaaaa atgtaattgc
6721 ttttcatgag tagtatgaat aaaattgatt agtttgtgtt ttcttgtctc ccgaaaaaaa
6781 aaaaaaaaaa aaaaaaaaaa aaa
```

Figure 5A (continued)

Polypeptide sequence (SEQ ID No:6)

MVGVGGGDVEDVTPRPGGCQISGRAARGCNGIPGAAAWEAALPRRRPRRHPSVNPRSR
AAGSPRTRGRRTEERPSGSRLGDRGRGRALPGGRLGGRGRGRAPERVGGRGRGRGTAA
PRAAPAARGSRPGPAGTMAAGSITTLPALPEDGGSGAFPPGHFKDPKRLYCKNGGFFL
RIHPDGRVDGVREKSDPHIKLQLQAEERGVVSIKGVCANRYLAMKEDGRLLASKCVTD
ECFFFERLESNNYNTYRSRKYTSWYVALKRTGQYKLGSKTGPGQKAILFLPMSAKS

Figure 5B

METHODS OF DIAGNOSING OVARIAN CANCER AND KITS THEREFOR

CROSS-REFERENCE TO RELATED APPLICATIONS

This application is a National Entry Application of PCT application no PCT/CA2006/001536 filed on Sep. 15, 2006 and published in English under PCT Article 21(2), which itself claims priority on U.S. provisional application Ser. No. 60/716,941, filed on Sep. 15, 2005. All documents above are incorporated herein in their entirety by reference.

FIELD OF THE INVENTION

The present invention relates to methods of diagnosing ovarian cancer and kits therefor. More particularly, the present invention relates to the identification of markers associated with ovarian cancer and their use to detect ovarian cancer. The invention further relates to methods and reagents for the diagnosis of ovarian cancer.

SEQUENCE LISTING

This application contains a Sequence Listing in computer readable form entitled 14257_13.5T25, created Jan. 5, 2007 having a size of 408 Kb. The computer readable form is incorporated herein by reference.

BACKGROUND OF THE INVENTION

Epithelial ovarian carcinoma (EOC) is the most common malignant ovarian tumor, representing 80% of all ovarian malignancies (1). EOCs are thought to originate from either the normal ovarian surface epithelium (OSE) itself or from the crypts and inclusion cysts located in the stroma (1). EOCs are heterogeneous and are designated according to their histological subtype: serous, endometrioid, mucinous, clear cell, Brenner, undifferentiated or mixed (association of two or more sub-types) (2, 3). This cancer is often asymptomatic where over 70% of patients with ovarian cancer are diagnosed at an advanced stage of the disease. While up to 80% of the patients will initially respond to treatment, recurrence is generally observed within variable time intervals. Although 10-15% of the patients achieve and maintain a complete response to therapy, the remaining patients show persistent disease or eventually relapse thus requiring additional treatment. In contrast, borderline or low malignant potential (LMP) tumors, which represent 10-20% of all EOCs, have a more favorable prognosis compared to the invasive form of the disease, where the 5-year survival rate falls below 30% (1, 4).

Currently, there is no reliable method for screening early stage ovarian cancer. The clinically used CA125 serum marker (5) combined with trans-vaginal sonography, 3-dimensional ultrasound or power Doppler have yielded only minimal results (6). The reduced efficacy of CA125 for screening is largely related to its poor specificity. While elevated levels of CA125 are generally associated with the malignant disease, increased serum CA125 levels have also been observed with benign conditions (7), non-neoplastic conditions such as first trimester of pregnancy, menstruation, endometriosis, uterine fibrosis, acute salphingitis, hepatic diseases and inflammation of peritoneum, pericardium or pleura as well as with cancers of other sites. In addition, CA125 levels generally fail to rise in early stage disease, and lower levels are also associated with endometrioid and mucinous ovarian tumors (8). Thus, there is a need to develop reliable screening tools for EOC as these would be extremely valuable for improving cancer detection, clinical management and subsequently impact positively on survival.

Microarray technology is a powerful method for the analysis of cancer-specific gene expression by measuring tumor-specific expression of thousands of genes in hundreds of tumors (9), which can then be associated with specific clinical parameters. Candidate genes for diagnostic markers can further be characterized in combination with a large-scale quantitative polymerase chain reaction (Q-PCR) of RNA and immunohistochemical (IHC) analysis of protein expression using tissue arrays. However, such diagnostic techniques are difficult to implement since they require surgery to obtain the epithelial ovarian samples. Alternatively, if the differentially expressed gene encodes for a secreted protein circulating in peripheral blood, such a protein represents a potential serum based marker. The most common approach for testing such peripheral blood markers is through an enzyme-linked immunosorbent assay (ELISA). Although previous studies have investigated the potential of prostasin, osteopontin, mesothelin and HE4 (10-13) as diagnostic markers of EOC, no single marker has been shown to be sufficiently sensitive nor specific for proper diagnosis of ovarian cancer. Various combinations of different tumor markers have shown a higher specificity in differentiating benign from malignant disease (13, 14). However the efficacy and/or sensitivity of these markers were limited to advanced stage serous subtype tumors.

Therefore, ovarian cancer still remains a major source of morbidity and mortality and there is a clear need for the development of novel diagnosis method having the required sensitivity and specificity for early and reliable detection of ovarian cancer.

The present description refers to a number of documents, the content of which is herein incorporated by reference in their entirety.

Other objects, advantages and features of the present invention will become more apparent upon reading of the following non-restrictive description of specific embodiments thereof, given by way of example only with reference to the accompanying drawings.

SUMMARY OF THE INVENTION

The invention relates to markers associated with ovarian cancer and corresponding methods, uses and products (e.g. probes, collections, kits, etc.) for the diagnosis of ovarian cancer.

Accordingly, in a first aspect, the invention provides a method comprising:
  (a) providing a biological sample from a subject (subject sample); and
  (b) detecting the expression level of each of the markers FGF-2 and CA125 in the subject sample.

In an embodiment, the above-mentioned subject is susceptible of having ovarian cancer.

In an embodiment, the above-mentioned subject is asymptomatic for ovarian cancer.

In an embodiment, the above-mentioned method further comprises:
  (c) comparing the expression level of each of the markers in the subject sample to corresponding pre-determined threshold expression levels for each of the markers, wherein an expression level of each of the markers in the subject sample that is higher than the pre-determined threshold expression levels for each of the markers is an indication that the subject is affected by ovarian cancer.

In an embodiment, the above-mentioned method further comprises:

(c) comparing the expression level of each of the markers in the subject sample to the expression level of each of the markers in a control sample, wherein an expression level of each of the markers that is higher in the subject sample than in the control sample is an indication that the subject is affected by ovarian cancer In an embodiment, the above-mentioned method further comprises:

(c) comparing the expression level of each of the markers in the subject sample to the expression level of each of the markers in a sample from the subject at an earlier time, wherein an expression level of each of the markers that is higher in the subject sample than in the sample from the subject at an earlier time is an indication that the subject is affected by ovarian cancer.

In an embodiment, the above-mentioned method further comprises:

(c) comparing the expression level of each of the markers in the subject sample to the expression level of each of the markers in a non-cancerous sample from the subject, wherein an expression level of each of the markers that is higher in the subject sample than in the non-cancerous sample from the subject is an indication that the subject is affected by ovarian cancer.

In an embodiment, the above-mentioned threshold expression level for each of the markers is determined by Receiver Operator Curves comparing the concentration of each of the markers in an ovarian cancer-free control population with that in a population affected by ovarian cancer.

In an embodiment, the above-mentioned expression is determined at the polypeptide level. In a further embodiment, the expression is determined using an immunoassay. In a further embodiment, the immunoassay is enzyme-linked immunosorbent assay (ELISA).

In an embodiment, the expression level of each of the above-mentioned markers is above the following pre-determined threshold expression levels: 50 U/ml for CA125 and 37 pg/ml for FGF-2.

In an embodiment, step (b) of the above-mentioned further comprises detecting the concentration of marker IL-18 in the sample.

In an embodiment, step (b) of the above-mentioned further comprises detecting the concentration of marker IL-18 in the sample, and the expression level of IL-18 in the sample is above the pre-determined threshold expression level of 215 pg/ml for this marker.

In an embodiment, the above-mentioned subject sample is a body fluid sample. In a further embodiment, the above-mentioned subject sample is selected from the group consisting of blood, plasma and serum. In a further embodiment, the above-mentioned subject sample is serum.

In an embodiment, the above-mentioned subject sample is primary culture cells derived from an ovarian tumor sample from the subject.

In an embodiment, the above-mentioned method is in vitro.

In an other aspect, the present invention provides a kit comprising means for detection of an expression level of each of markers CA125 and FGF-2 in a biological sample from a subject (subject sample), and instructions to use said markers in a method as recited above.

In an embodiment, the above-mentioned kit further comprises means for detection of an expression level of marker IL-18.

In an embodiment, the above-mentioned means for detection of expression level of each of the markers are antibodies.

In an other aspect, the invention provides a method of assessing the potential efficacy of a test compound for treating or inhibiting ovarian cancer in a subject, said method comprising determining the expression level of each of markers CA125 and FGF-2 in a biological sample from the subject (subject sample), before and after administration of the test compound to the subject, wherein a decrease in the expression level of the markers after administration of the test compound is indicative that said test compound is effective for treating or inhibiting ovarian cancer.

In an other aspect, the invention provides a method of assessing the potential efficacy of a therapy for treating or inhibiting ovarian cancer in a subject, said method comprising determining the expression level of each of markers CA125 and FGF-2 in a biological sample from the subject (subject sample), before and after administration of said therapy in said subject, wherein a decrease in the expression level of said markers after administration of said therapy is indicative that said therapy is effective for treating or inhibiting ovarian cancer.

In an embodiment of the above-mentioned methods, the methods further comprise detecting the concentration of marker IL-18 in the sample. In an embodiment, the above-mentioned expression is determined at the polypeptide level. In a further embodiment, the expression is determined using an immunoassay. In a further embodiment, the immunoassay is enzyme-linked immunosorbent assay (ELISA).

In an embodiment, the above-mentioned sample is a body fluid sample. In a further embodiment, the above-mentioned sample is selected from the group consisting of blood, plasma and serum. In a further embodiment, the above-mentioned sample is serum.

In an embodiment, the above-mentioned subject is a human.

In an embodiment, the above-mentioned ovarian cancer is epithelial ovarian carcinoma (EOC).

Figure 1A:
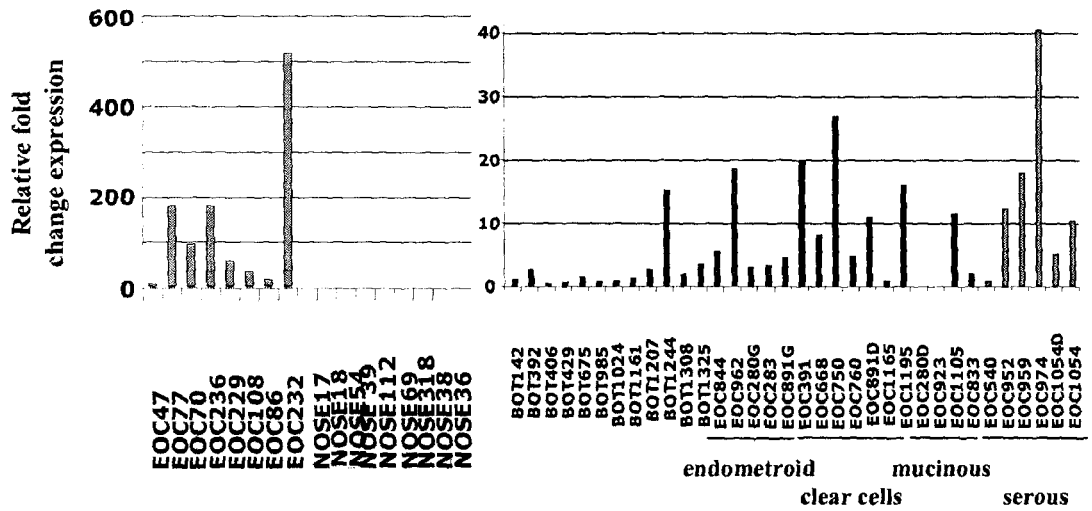
FIG. 1 shows validation of gene expression profiles by Q-PCR on primary culture samples. (A) Two micrograms of RNA extracted from 9 NOSE and 8 primary culture cells of EOC were reverse-transcribed and the levels of IL-18 and FGF-2 quantified using specific primers (left hand panels). Each expression level was normalized to that of the control RNA. Relative fold change expression is the ratio of the NOSE 18 gene expression to that of other samples. Three micrograms of RNA extracted from 12 BOT (benign ovarian tumor) tissues and 22 EOC tissues were reverse-transcribed and the levels of IL-18 and FGF-2 quantified as in the left hand panels (right hand panels). Each expression level was normalized to that of the control RNA. Relative fold change expression is the ratio of the BOT142 gene expression to that of other samples; (B) shows the expression of IL-18 and FGF-2 in normal ovarian surface epithelial (NOSE) tissues and four histopathologies of EOC tissues. IHC was performed using antibodies against indicated proteins (left). Nuclei are counterstained with hematoxylin (blue). Brown color demonstrates specific peroxidase staining.
Figure 1A:
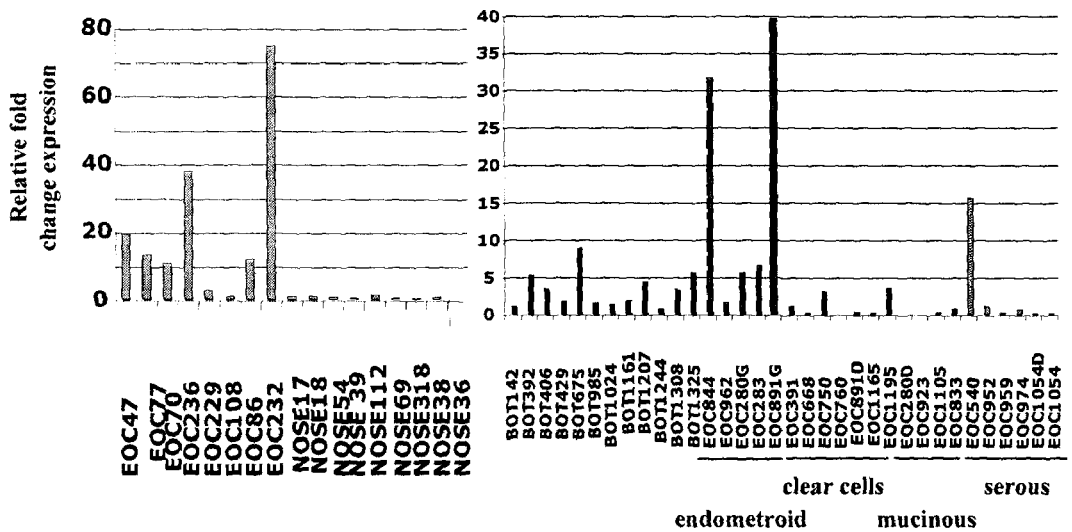

benign ovarian tumor patients (n=23). TOV: ovarian tumor patients (equivalent to EOC: invasive epithelial ovarian cancer patients) (n=42);

FIG. 3 presents nucleic acid (SEQ ID NO: 1) and polypeptide (SEQ ID NO: 2) sequences for CA125;

FIG. 4 presents nucleic acid (SEQ ID NO: 3) and polypeptide (SEQ ID NO: 4) sequences for IL-18; and FIG. 5 presents nucleic acid (SEQ ID NO: 5) and polypeptide (SEQ ID NO: 6) sequences for FGF-2.

DESCRIPTION OF ILLUSTRATIVE EMBODIMENTS

The present invention concerns markers which can be used to diagnose ovarian cancer in subjects.

"Selectivity" in the context of the present invention refers to the ability of a marker of the present invention to discriminate between a sample affected by ovarian cancer and one that is not i.e. a marker with high selectivity produces few false positives.

"Sensitivity" in the context of the present invention refers to the ability of a marker of the present invention to correctly identify a sample affected by ovarian cancer as such i.e. a marker with high sensitivity produces few false negatives.

"Marker" in the context of the present invention refers to, without being so limited, a nucleic acid or a polypeptide (or fragment thereof), which is differentially present in a sample taken from a subject having ovarian cancer as compared to a comparable sample taken from a control subject (e.g., a person with a negative diagnosis or undetectable cancer, normal or healthy subject).

"Subject" in the context of the present invention relates to any mammal including a mouse, rat, pig, monkey, horse. In a specific embodiment, it refers to a human.

As used herein the terms "sample from the subject at an earlier time is meant to refer to a sample from a subject at a time where it was known that the subject was not affected by ovarian cancer.

The articles "a," "an" and "the" are used herein to refer to one or to more than one (i.e., to at least one) of the grammatical object of the article.

The term "including" and "comprising" are used herein to mean, and are reused interchangeably with, the phrases "including but not limited to" and "comprising but not limited to".

The term "such as" is used herein to mean, and is used interchangeably with, the phrase "such as but not limited to".

Optionally, a marker can be modified before analysis to improve its resolution or to determine its identity. For example, the markers may be subject to proteolytic digestion before analysis. Any protease can be used. Proteases, such as trypsin, that are likely to cleave the markers into a discrete number of fragments are particularly useful. The fragments that result from digestion function as a fingerprint for the markers, thereby enabling their detection indirectly. This is particularly useful where there are markers with similar molecular masses that might be confused for the marker in question. Also, proteolytic fragmentation is useful for high molecular weight markers because smaller markers are more easily resolved by mass spectrometry. The markers can also be modified by the attachment of a tag of particular molecular weight that specifically bind to molecular markers, further distinguishing them. Optionally, after detecting such modified markers, the identity of the markers can be further determined by matching the physical and chemical characteristics of the modified markers in a protein database (e.g., SwissProt™).

Expression levels may in general be detected by either detecting mRNA from the cells and/or detecting expression products, such as polypeptides and proteins. Expression of the transcripts and/or polypeptides encoded by the nucleic acids described herein may be measured by any of a variety of known methods in the art. In general, the nucleic acid sequence of a nucleic acid molecule (e.g., DNA or RNA) in a subject sample can be detected by any suitable method or technique of measuring or detecting gene sequence or expression. Such methods include, but are not limited to, polymerase chain reaction (PCR), reverse transcriptase-PCR (RT-PCR), in situ PCR, quantitative PCR (q-PCR), in situ hybridization, Southern blot, Northern blot, sequence analysis, microarray analysis, detection of a reporter gene, or other DNA/RNA hybridization platforms. For RNA expression, preferred methods include, but are not limited to: extraction of cellular mRNA and Northern blotting using labeled probes that hybridize to transcripts encoding all or part of one or more of the genes of this invention; amplification of mRNA expressed from one or more of the genes of this invention using gene-specific primers, polymerase chain reaction (PCR), quantitative PCR (q-PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding all or part of the genes of this invention, arrayed on any of a variety of surfaces; in situ hybridization; and detection of a reporter gene. The term "quantifying" or "quantitating" when used in the context of quantifying transcription levels of a gene can refer to absolute or to relative quantification. Absolute quantification may be accomplished by inclusion of known concentration(s) of one or more target nucleic acids and referencing the hybridization intensity of unknowns with the known target nucleic acids (e.g., through generation of a standard curve). Alternatively, relative quantification can be accomplished by comparison of hybridization signals between two or more genes, or between two or more treatments to quantify the changes in hybridization intensity and, by implication, transcription level.

As used herein, "control sample" refers to a sample of the same type, that is, obtained from the same biological source (e.g. body fluid, tissue, etc.) as the tested sample but from a healthy subject, (i.e. who is not afflicted by ovarian cancer, and preferably who is not afflicted by any cancer). The control sample can also be a standard sample that contains the same concentration of the above-mentioned markers that are normally found in a corresponding biological sample obtained from a healthy subject. For example, there can be a standard control sample for the amounts of CA125, IL-18 and FGF-2 normally found in biological samples such as tissue, blood, plasma and serum.

The methods of the invention can also be practiced, for example, by selecting a combination of the above-mentioned markers and one or more additional markers for which increased or decreased expression correlates with ovarian cancer, such as CA72-4, hK6, hK10, HSCCE, kallikrein 4, kallikrein 5, kallikrein 6, kallikrein 8, kallikrein 9, kallikrein 11, CA15-3, CA19-9, OVX1, lysophosphatidic acid (LPA) or carcinoembryonic antigen (CEA), as well as other markers specific for other types of cancer. Those skilled in the art will be able to select useful diagnostic markers for detection in combination with CA125, IL-18 and FGF-2. Similarly, four or more or five or more or a multitude of markers can be used together for determining a diagnosis of a patient.

In an embodiment, the expression level of the above-mentioned markers is determined at the polypeptide level.

Methods to measure polypeptide expression levels of the markers of this invention, include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), flow cytometry, and assays based on a property of the protein including but not limited to DNA binding, ligand binding, or interaction with other protein partners.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

In an embodiment, the expression level of the above-mentioned markers is determined using an immunoassay.

An immunoassay is an assay that uses an antibody to specifically bind an antigen (e.g., a marker). The immunoassay is characterized by the use of specific binding properties of a particular antibody to isolate, target, and/or quantify the antigen. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a marker from specific species such as rat, mouse, or human can be selected to obtain only those polyclonal antibodies that are specifically immunoreactive with that marker and not with other proteins, except for polymorphic variants and alleles of the marker. This selection may be achieved by subtracting out antibodies that cross-react with the marker molecules from other species.

Using the purified markers or their nucleic acid sequences, antibodies that specifically bind to a marker can be prepared using any suitable methods known in the art. See, e.g., Harlow & Lane, Antibodies: A Laboratory Manual (1988) and Goding, Monoclonal Antibodies: Principles and Practice (2d ed. 1986). Such techniques include, but are not limited to, antibody preparation by selection of antibodies from libraries of recombinant antibodies in phage or similar vectors, as well as preparation of polyclonal and monoclonal antibodies by immunizing rabbits or mice.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. The sample is preferably a biological fluid sample taken from a subject. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxidase, alkaline phosphatase and others commonly used in an ELISA), and colorimetric labels such as colloidal gold or colored glass or plastic beads. Alternatively, the marker in the sample can be detected using an indirect assay, wherein, for example, a second labeled antibody is used to detect bound marker-specific antibody, and/or in a competition or inhibition assay wherein, for example, a monoclonal antibody which binds to a distinct epitope of the marker is incubated simultaneously with the mixture.

Methods for measuring the amount of, or presence of, antibody-marker complex include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Electrochemical methods include voltametry and amperometry methods. Radio frequency methods include multipolar resonance spectroscopy. Methods for performing these assays are readily known in the art. Useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology: Antibodies in Cell Biology, volume 37 (Asai, ed. 1993); Basic and Clinical Immunology (Stites & Terr, eds., 7th ed. 1991); and Harlow & Lane, supra.

In a further embodiment, the above-mentioned immunoassay is an enzyme-linked immunosorbant assay (ELISA).

The markers can be measured in different types of biological samples. The sample is preferably a biological fluid sample such as blood, plasma and serum. Other typical biological samples include, but are not limited to, tissue biopsy from ovarian tumor, sputum, lymphatic fluid, blood cells (e.g., peripheral blood mononuclear cells), tissue or fine needle biopsy samples, urine, peritoneal fluid, colostrums, breast milk, fetal fluid, tears, pleural fluid, or cells therefrom. Because all of the markers are found in blood serum, blood serum is a preferred sample source for embodiments of the invention.

If desired, the sample can be prepared to enhance detectability of the markers. For example, to increase the detectability of markers, a blood serum sample from the subject can be preferably fractionated by, e.g., Cibacron™ blue agarose chromatography and single stranded DNA affinity chromatography, anion exchange chromatography, affinity chromatography (e.g., with antibodies) and the like. The method of fractionation depends on the type of detection method used. Any method that enriches for the protein of interest can be used. Sample preparations, such as pre-fractionation protocols, are optional and may not be necessary to enhance detectability of markers depending on the methods of detection used. For example, sample preparation may be unnecessary if antibodies that specifically bind markers are used to detect the presence of markers in a sample.

Typically, sample preparation involves fractionation of the sample and collection of fractions determined to contain the markers. Methods of pre-fractionation include, for example, size exclusion chromatography, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis. Examples of methods of fractionation are described in WO/2003/057014.

The methods for detecting these markers in a sample have many applications. For example, one or more markers can be measured to aid human cancer diagnosis. In another example, the methods for detection of the markers can be used to monitor responses in a subject to cancer treatment. In another example, the methods for detecting markers can be used to assay for and to identify compounds that modulate expression of these markers in vivo or in vitro.

In an embodiment, the subject is a human.

The present invention also relates to a kit for determining the likelihood of ovarian cancer in a subject, said kit comprising means for detection of expression of the markers CA125 and FGF-2 and, in more specific embodiments, the marker IL-18, in a biological sample from said subject together with instructions setting forth the above-mentioned method. Means for detection include probe, primer (or primer pair), or immunological reagent (e.g. antibody) in accordance with the present invention. For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers may for example include a container which will accept the test sample (DNA, protein or cells), a container which contains the primers used in the assay, containers which contain enzymes, containers which contain wash reagents, and containers which contain the reagents used to detect the indicator products.

Kits for evaluating expression of nucleic acids can include, for example, probes or primers that specifically bind a nucleic acid of interest (e.g., a nucleic acid, the expression of which correlates with increased likelihood of ovarian cancer). The kits for evaluating nucleic acid or polypeptide expression can provide substances useful as standard (e.g., a sample containing a known quantity of a nucleic acid or polypeptide to which test results can be compared, with which one can assess factors that may alter the readout of a diagnostic test, such as variations in an enzyme activity or binding conditions). Kits for assessing nucleic acid or polypeptide expression can further include other reagents useful in assessing levels of expression (e.g. buffers and other reagents for performing amplification reactions, or for detecting binding of a probe to a nucleic acid or binding of an antibody to a polypeptide). The kits can provide instructions for performing the assay used to evaluate gene/polypeptide expression for determining likelihood of ovarian cancer based on the results of the assay. For example, the instructions can indicate that levels of expression of a gene of interest (e.g., relative to a standard or a control), correlate with increased likelihood for ovarian cancer.

The invention further provides a method of assessing the potential efficacy of a test compound for treating or inhibiting ovarian cancer in a subject, said method comprising determining, in a biological sample from said subject, the expression of the markers CA125 and FGF-2 and, in more specific embodiments, the marker IL-18, before and after administration of said test compound in said subject, wherein a decrease in the expression of said markers after administration of said test compound is indicative that said test compound is effective for treating or inhibiting ovarian cancer.

In an other aspect, the invention provides a method of assessing the efficacy of a therapy for treating or inhibiting ovarian cancer in a subject, said method comprising determining, in a biological sample from said subject, the expression of the markers CA125 and FGF-2 and, in more specific embodiments, the marker IL-18, before and after administration of said therapy in said subject, wherein a decrease in the expression of said markers after administration of said therapy is indicative that said therapy is effective for treating or inhibiting ovarian cancer.

In an embodiment, the above-mentioned ovarian cancer is epithelial ovarian carcinoma.

The present invention is illustrated in further details by the following non-limiting examples.

Example 1

Clinical Samples

Tissue samples and sera were obtained with informed consent from participants. Tumor samples were collected from surgeries performed at the Centre Hospitalier de l'Université de Montréal (CHUM). Histopathology, grade and stage of tumors were assigned according to the International Federation of Gynecology and Obstetrics (FIGO) criteria. Normal controls were defined as tumor-free patients. Primary cell cultures from normal ovarian surface epithelia (NOSE) and EOC samples were established as described (15, 16) and used for microarray analysis. Cells in primary culture were maintained in OSE media consisting of 50:50 medium 199:105 (Sigma) supplemented with 10% fetal bovine serum (FBS), 2.5 µg/mL amphotericin B and 50 µg/mL gentamicin (15). Independent cohorts for microarray, ELISA and tissue array IHC studies were used and are presented in Table 1 below.

Quantitative PCR

Linear amplification of RNA from primary culture cells was performed as described previously (17). The cDNA synthesis was done according to the protocol of the SuperScript™ First-Strand Synthesis System for Q-PCR (Invitrogen Life Technologies) with a starting amount of 2 mg RNA and reverse transcription performed with random hexamers. The PCR reaction (temperature, specificity) was performed using conventional PCR conditions with a Rotor-gene™ 3000 Real-Time Centrifugal DNA Amplification System (Corbett tumor tissues Research, NSW, Australia). The Quantitect™ SYBR Green PCR (Qiagen Inc., ON, Canada) reaction mixture was used according to the manufacturer instruction. Serial dilutions were performed to generate a standard curve for each gene tested in order to define the efficiency of the Q-PCR reaction and a melt curve was done to confirm the specificity of the reaction. Based on the stability of its expression in microarray experiments, primers for the ERK1 gene were used as an internal control. Experiments were done in duplicate. Positive and negative controls were introduced in all experiments. The sequences for IL-18 primers are: Fwd 5'-CGCTTCCTCTCGCMCAAACTAT-3' (SEQ ID NO: 7) and Rev 5'-CCGGGGTGCATTATCTCTACAGT-3' (SEQ ID NO: 8); FGF-2: Fwd 5'-CGCGCAGGAGGGAGGAGA-3' (SEQ ID NO: 9) and Rev 5'-ACGCCGCCTGGGGAGAG-3' (SEQ ID NO: 10) and finally ERK1: Fwd 5'-GCGCTGGCT-CACCCCTACCT-3' (SEQ ID NO: 11) and Rev 5'-GC- CCCAGGGTGCAGAGATGTC-3' (SEQ ID NO: 12). The Pfaffl analysis was used method to measure the relative quantity of gene expression (18).

RNA Preparation and Microarray

Total RNA was extracted with TRIzol™ reagent (Gibco/BRL, Life Technologies Inc., Grand Island, N.Y., USA). RNA was extracted directly from cells grown to 80% confluency. The quality of the RNA was monitored by gel electrophoresis and a 2100 Bioanalyzer using the RNA 6000 Nano LabChip™ kit (Agilent Technologies, Germany). Biotinylated hybridization target was prepared from total RNA as described (19). HuGeneFI™ 6800 GeneChip™ microarray experiments were performed at the McGill University and Genome Quebec Innovation Centre and raw data was processed using the Affymetrix™ MAS4 software. Detailed protocols are known in the art and are available at www.genomequebec.mcgill.ca/center.php. The raw data of each experiment was normalized according to the mean of the global intensity adjusted to 100 units. Arrays with global intensity below 100 were eliminated. After normalization, all values below 20 were considered as technical noise and expression values below this threshold were transformed to this value. All the EST's were next filtered, which had "A" call (ambiguous signal) across all samples. To detect differentially expressed genes in ovarian tumor samples versus normal ovarian cells, two statistical tests were used to identify classifiers. A parametric and a non-parametric (Mann-Whitney (U)) test were performed using GeneSpring™ software (Silicon Genetics). Candidate genes identified in common in the two analyses were selected for further analysis.

Tissue Array and IHC

The following monoclonal antibodies were used in immunohistochemistry (IHC): anti-IL-18 (R&D system), anti-FGF-2 (Santa Cruz Biotechnology). A tissue array containing 94 cores of ovarian epithelial tissues (see Table 1 below) was built and used for IHC studies. Briefly, the tissue array was heated at 60° C. for 30 min, deparaffinized in toluene and rehydrated in a gradient of ethanol. To unmask antigen the slides were submerged in 90° C. citrate buffer (0.01 M citric acid+500 ul tween-20/L adjusted to pH 6.0) (J. T. Baker Philipsburg, N.J.) for 15 min. The tissue was blocked with a protein-blocking serum-free reagent (DakoCytomation Inc., Mississauga, ON) and incubated with the different antibodies overnight at 4° C. in a humid chamber. The optimal concentration for each primary antibody was determined by serial dilutions. Subsequently, endogenous peroxidase activity was quenched by treatment with 3% $H_2O_2$. The array was then incubated with a secondary biotinylated antibody (DakoCytomation Inc., Mississauga, ON) for 10 min followed by incubation with a streptavidin-peroxidase complex (Dako Diagnostics Canada Inc.) for 10 min at room temperature. Reaction products were developed using diaminobenzidine (brown stain) containing 0.3% $H_2O_2$ as a substrate for peroxidase and nuclei were counterstained with diluted hematoxylin (blue stain). Epithelial zones were scored according to the intensity of staining (value of 0 for absence, 1 for weak, 2 for moderate, 3 for high intensity). Each array was independently analyzed in a blind study by two independent observers. Statistical analyses were performed using the T-test.

ELISA

Patient's blood was centrifuged for 30 min at 2500 rpm and the separated serum was immediately frozen at −20° C. until further use. Before measurement, all sera were re-centrifuged for 10 min at 8000 rpm. The sera were further tested by ELISA for CA125 (Panomics BC1013), FGF-2 (R&D System, item DFB50) and IL-18 (R&D System, item 7620) concentration according to the manufacturer's instructions. The limit of detection for IL-18 was 20 pg/ml, 10 U/ml for CA125 and 20 pg/ml for FGF-2. Independent experiments were calibrated with at least two samples. Statistical analyses were performed using SPSS software. For small sample set sizes (<10) the Mann-Whitney U test was applied, otherwise statistical analysis relied on the T-test.

Example 2

Identification of Two Genes Up-Regulated in Ovarian Cancer and Encoding for Cytokines Comparative analysis of gene expression profiles of ovarian epithelial cells was performed using 11 primary cultures of normal ovarian epithelial surface (NOSE) samples and 39 primary cultures of EOC samples. The 39 EOC represented different grades, stages and pathologies of ovarian cancer (see Table 1 below). To gain insight into genes exhibiting dominant expression levels in ovarian tumors, the expression profiles were analyzed using two different supervised classification algorithms. Among a total of 177 candidate genes that were common to both supervised analyses, several genes encoding for secreted proteins were identified but only two genes encoding for cytokines, IL-18 and FGF-2, were present. In order to maximize the chance of sampling differential gene expression in serum, these latter two genes were selected for further study.

TABLE 1

SAMPLE SETS USED IN EACH EXPERIMENT

| Histopathology | Sample size | Tumor grade | | | | | Tumor stage | |
|---|---|---|---|---|---|---|---|---|
| | | B | 1 | 2 | 3 | Mixed | Low | high |
| Microarray set (n = 50) | | | | | | | | |
| Normal | 11 | | | | | | | |
| Serous | 29 | 6 | 1 | 7 | 15 | | 4 | 25 |
| Endometroid | 7 | | | 3 | 4 | | | 7 |
| Mixed | 1 | | | | 1 | | | 1 |
| Clear cell | 2 | | | | 2 | | | 2 |
| Total tumors | 39 | 6 | 1 | 10 | 22 | | 4 | 35 |
| Tissue array (n = 114) | | | | | | | | |
| Normal | 20 | | | | | | NA | NA |
| Serous | 21 | 4 | 5 | 5 | 7 | | NA | NA |
| Endometroid | 27 | | 13 | 7 | 5 | 2 | NA | NA |
| Clear cell | 17 | | | 5 | 9 | 3 | NA | NA |
| Mixed | 5 | | | | 3 | 2 | NA | NA |
| Mucinous | 24 | 21 | 3 | | | | NA | NA |
| Total tumors | 94 | 25 | 18 | 17 | 24 | 6 | NA | NA |
| ELISA set (n = 70) | | | | | | | | |
| Normal and benign | 25 | | | | | | | |
| Serous | 29 | 3 | 2 | 3 | 20 | 1 | 3 | 26 |
| Endometroid | 3 | | 3 | | | | 2 | 1 |
| Clear cell | 5 | | | | 4 | 1 | 3 | 2 |
| Mixed | 3 | | 1 | 1 | 1 | | 0 | 3 |
| Brenner | 2 | | | | | 2 | 1 | 1 |
| Mucinous | 3 | 2 | 1 | | | | 2 | 1 |
| Total tumors | 45 | 5 | 7 | 4 | 25 | 4 | 11 | 34 |
| PCR tissues (n = 34) | | | | | | | | |
| Normal and benign | 12 | | | | | | | |
| Serous | 6 | 1 | | 1 | 2 | | 2 | 4 |

TABLE 1-continued

SAMPLE SETS USED IN EACH EXPERIMENT

| Histopathology | Sample size | Tumor grade | | | | | Tumor stage | |
|---|---|---|---|---|---|---|---|---|
| | | B | 1 | 2 | 3 | Mixed | Low | high |
| Endometrioid | 5 | | 1 | | 4 | | | 5 |
| Clear cell | 7 | | | | 5 | 2 | 1 | 6 |
| Mucinous | 4 | 2 | 1 | | 1 | | 1 | 2 |
| Total tumors | 22 | 3 | 2 | 3 | 12 | 2 | 4 | 18 |

Grade B are low malignant potential tumors.
Low stage: stage I and II tumors;
high stage: stage III and IV tumors.

Example 3

Validation of the Differential Gene Expression of IL-18 and FGF-2

Q-PCR was used to validate the differential expression of the IL-18 and FGF-2 RNA as observed in the microarray analysis. For this purpose, 9 NOSEs and 8 EOCs randomly chosen from the previous set of primary cultures, as well as 12 benign tumors (BOT) and 22 EOCs from fresh tissues, were compared and their expression levels correlated with the results obtained by microarray analysis (FIG. 1A, left hand panels). IL-18 and FGF-2 RNA were weakly detectable in NOSE samples while they were readily detectable in the majority of malignant samples serving as an independent confirmation of their differential expression in EOC. To determine IL-18 and FGF-2 expression in tissues, RNAs isolated from 12 benign and 22 malignant ovarian tumor tissues were also tested (Table I). Most malignant tissues, with the exception of two mucinous and one serous tumor, showed an overexpression of IL-18 (FIG. 1A, right hand panels). Highest FGF-2 RNA expression was seen in endometroid tissues, although the difference between benign and malignant tissues was less striking (FIG. 1A, right hand panels).

Example 4

Protein Expression of IL-18 and FGF-2 in Ovarian Tissue Specimens

Figure 1B:
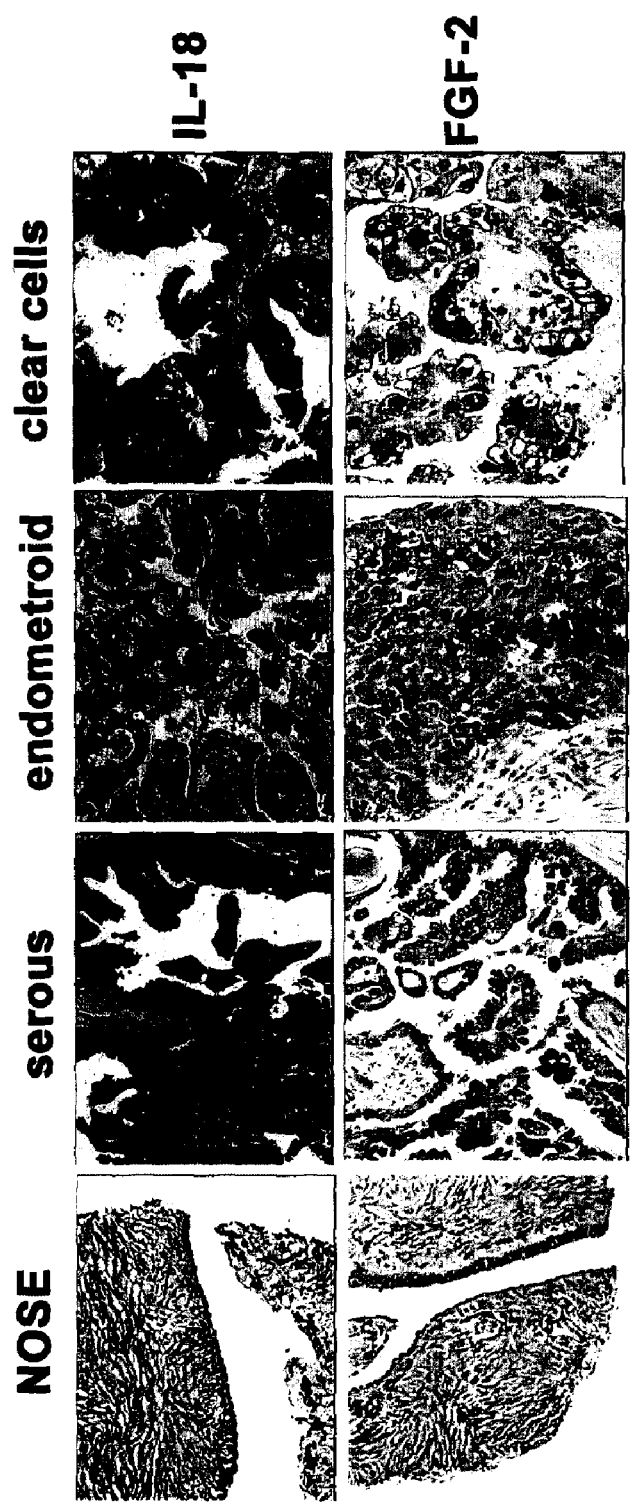

To address the expression of FGF-2 and IL-18 in EOC, IHC was performed with IL-18 and FGF-2 specific antibodies on ovarian tissues using a tissue array containing 20 NOSE and 94 EOC tissue cores from 114 independent patients. The 94 EOC cores represented the different grades and pathologies of ovarian cancer with the exception of Brenner tumors (see Table 1 above). Scoring results from the IHC analyses are summarized in Table 2 below. IL-18 and FGF-2 were expressed in NOSE as well as EOC tissues. In NOSE tissues, heterogeneity of staining intensity was observed among the different cores (see Table 2 below). In addition, IL-18 and FGF-2 staining was also present in the stroma of NOSE tissues, which may be due to their direct expression by stromal cells or to the secretion of these cytokines by adjacent epithelial cells. EOC tissues showed a slightly more marked staining of IL-18 and FGF-2. The staining was a significantly stronger for IL-18 in serous, endometrioid and clear cells tumors (p<0.05) and for endometrioid and clear cell tumors with FGF-2 (FIG. 1B and Table 2).

TABLE 2

INTENSITY OF IMMUNOSTAINING OF TISSUE ARRAY WITH ANTI-IL-18 AND ANTI-FGF-2 ANTIBODIES

| Histopathology | p | Staining intensity | | | |
|---|---|---|---|---|---|
| | | 0 | 1+ | 2+ | 3+ |
| Antibody anti-IL-18 | | | | | |
| Normal | | 3 | 13 | 4 | 0 |
| Clear cells | <0.001 | 0 | 1 | 14 | 2 |
| Endometrioid | 0.001 | 1 | 9 | 15 | 2 |
| Serous | 0.03 | 0 | 13 | 8 | 0 |
| Mixed | 0.05 | 0 | 2 | 3 | 0 |
| Mucinous | 0.20 | 8 | 11 | 5 | 0 |
| Total tumors | 0.005 | 12 | 36 | 45 | 4 |
| Antibody anti-FGF-2 | | | | | |
| Normal | | 5 | 7 | 5 | 3 |
| Clear cells | <0.001 | 0 | 2 | 12 | 3 |
| Endometrioid | 0.01 | 1 | 6 | 15 | 5 |
| Serous | 0.45 | 7 | 1 | 13 | 0 |
| Mixed | 0.33 | 2 | 0 | 3 | 0 |
| Mucinous | 0.08 | 11 | 8 | 6 | 0 |
| Total tumors | 0.14 | 21 | 17 | 49 | 8 |

$^a$0, absence; 1, weak; 2, moderate; 3, for high intensity.

Example 5

Serum IL-18 and FGF-2 Proteins as Markers of EOC

IL-18 and FGF-2 were studied as individual markers in comparison to CA125. For this purpose a total of 72 patients was selected: 25 patients were free of cancer and 47 patients had ovarian cancer (see Table 1 above). Among the cancer-free patients, six presented with benign ovarian (BOV) or (benign) tumors. Among the 47 ovarian cancers, five were low malignant potential (LMP) tumors, eight grade 1, four grade 2, and 26 grade 3 tumors (see Table 1 above). Six different pathologies were represented in the set of selected patients with EOC (serous, endometrioid, clear cells, Brenner, mucinous and mixed).

Figure 2:
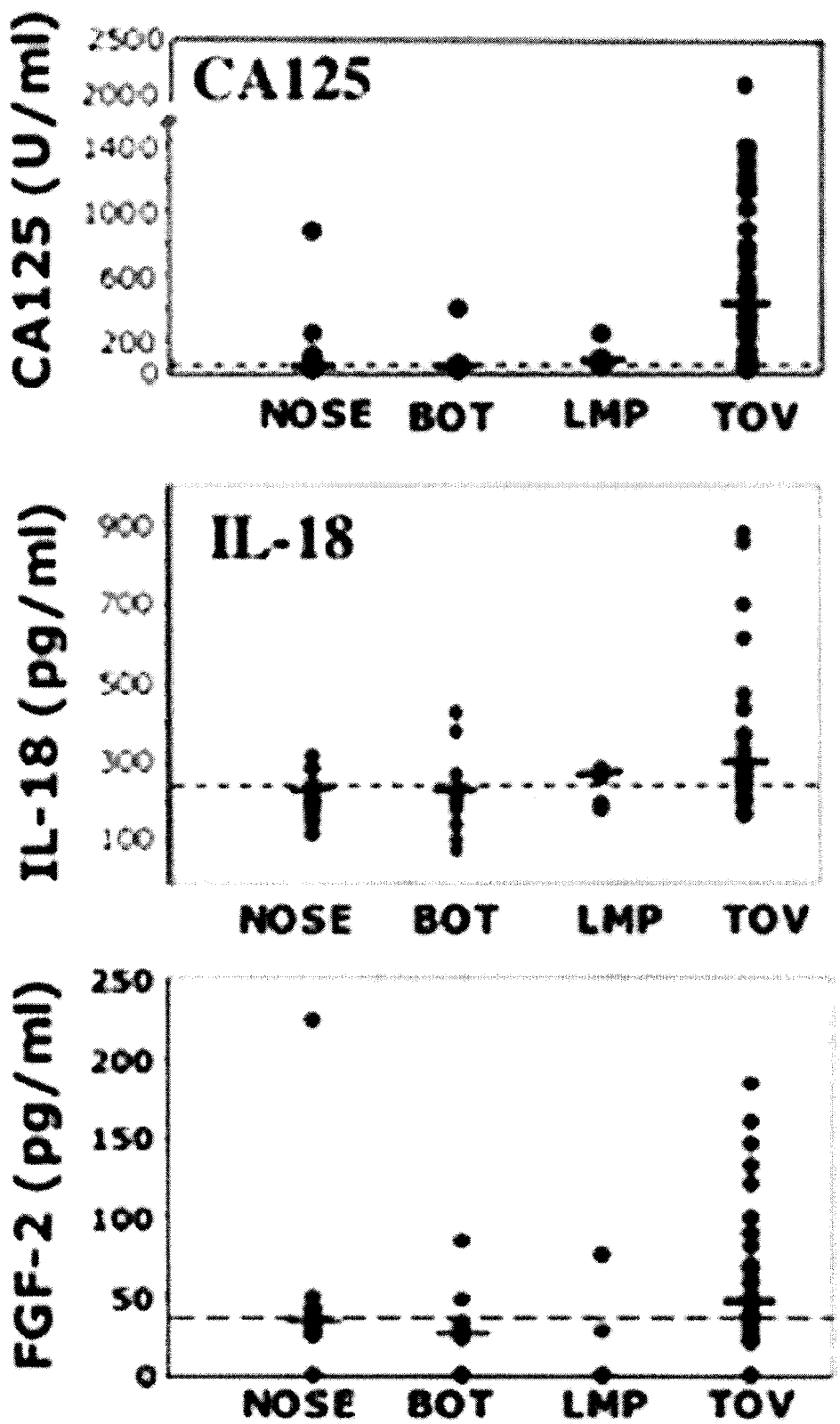
FIG. 2 shows serum measurement of CA125 (A) IL-18 (B) and FGF-2 (C) by ELISA. Patients sera was tested for all CA125, IL-18 and FGF-2 and threshold levels (dashed lines) were determined for each serum marker. Solid lines show the median level of the serum marker for each group of patients. LMP: low malignant potential tumor patients (n=5). NOSE: normal ovarian surface epithelia patients (n=11). BOT.

CA125 was significantly elevated in patients with EOC (p<0.001) (see Table 3 below). No significant difference was observed in patients with or without benign tumors (p=0.31). Patients with LMP tumors showed a lower level of CA125 (median 75 U/ml) than malignant EOC (median level 350 U/ml) (see FIG. 2 and Table 3 below). This observation was consistent with the increased levels of CA125 which correlated with increased tumor grade (r=0.33, p=0.004) and stage in independent studies (8). The increased level of CA125 also correlated with the histopathology (Spearman's Rho test p=0.002) where CA125 was more elevated in serous tumors than in endometrioid and clear cell tumors (see Table 3 below).

While IL-18 was also significantly more elevated in EOC patients (median level pg/ml p=0.003) it was correlated with tumor grade (Spearman's Rho test, p=0.172). Serous tumors showed the highest level of IL-18 expression (median level 305 pg/ml) but no significant correlation was observed between IL-18 and pathology disease (Spearman's Rho test, p=0.173). As observed with CA125, there was no significant difference between patients with or without benign tumors (p=0.99) (see Table 3 below).

FGF-2 levels were higher in EOC patients compared to cancer free patients although with a weaker significance compared to CA125 or IL-18 (p=0.04). In accordance with the results obtained in tissue arrays, serum FGF-2 levels were highest in association with clear cell tumors. A correlation between increased FGF-2 serum levels and tumor grade was also detected (Spearman's Rho test p=0.02) (Table 3).

TABLE 3

EXPRESSION LEVEL OF MARKERS CA125, IL-18 AND FGF-2 IN SERUM

|  | CA125 (U/ml) [Median/ average (p*)] | IL-18 (pg/ml) [Median/ average (p*)] | FGF-2 (pg/ml) [Median/ average (p*)] |
|---|---|---|---|
| NOSE + benign | 37/92 | 204/215 | 29/35 |
| All EOC | 306/474 (<0.001) | 264/315 (0.001) | 39/50 (0.037) |
| Normal | 44/114 | 203/212 | 34/43 |
| Benign | 32/63 (0.31) | 207/219 (0.99) | 27/25 (0.31) |
| LMP | 75/100 (0.30) | 236/257 (0.31) | 68/21 (0.175) |
| Invasive EOC | 350/545 (<0.001) | 258/327 (0.003) | 49/56 (0.006) |
| Grade 1 | 339/336 (0.03) | 282/267 (0.04) | 31/31 (0.70) |
| Grade 2 | 260/285 (0.04) | 251/283 (0.008) | 43/36 (0.011) |
| Grade 3 | 484/683 (<0.001) | 307/370 (0.003) | 66/68 (0.002) |
| Low stage | 75/419 (0.18) | 233/239 (0.62) | 39/47 (0.65) |
| High stage | 350/450 (<0.001) | 281/282 (<0.001) | 44/42 (0.016) |
| Serous | 419/544 (<0.001) | 305/358 (<0.001) | 44/54 (0.11) |
| Endometrioid | 339/380 (0.16) | 281/252 (0.37) | 23/23 (0.63) |
| Mucinous | 38/46 (0.79) | 263/247 (0.29) | 21/32 (0.68) |
| Clear cells | 34/492 (0.55) | 242/330 (0.30) | 69/49 (0.10) |

NOSE, normal ovarian surface epithelia;
EOC, epithelial ovarian cancer;
LMP, low malignant potential tumor;
low stage, stage I and II;
high stage, stage III and IV.
p* Mann-Whitney test.

Example 6

Diagnostic Potential of Serum CA125, IL-18 and FGF-2 as Markers

Receiver Operator Curves were used to determine threshold values for the three serum markers to compare the diagnostic potential of the individual cytokine markers with CA125. The greatest accuracy in differential diagnosis of malignant tumors was achieved with a threshold of 50 U/ml for CA125, 215 pg/ml for IL-18 and 37 pg/ml for FGF-2. Sensitivity, namely the fraction of patients correctly diagnosed with ovarian cancer, was more accurate when considering CA125 or IL-18, as individual markers. Sensitivity as determined by CA125 and IL-18 was 82% and 78% respectively, compared to 58% with FGF-2 (Table 4). To ensure that there was no difference in sensitivity between CA125 and IL-18 the number of samples was increased to 97 (data not shown). In this larger set, CA125 and IL-18 sensitivity levels remained similar (75% and 74%, respectively).

Specificity was defined as the fraction of samples correctly diagnosed as non-malignant, including serum from patients with normal ovaries or benign disease. Individual analysis of patients with either normal ovaries or benign disease gave similar results (data not shown). Specificity was best provided by FGF-2 (72%). CA125 and IL-18 showed relative low similar specificities of 60% and 64% respectively (Table 4). In the larger set, CA125 and IL-18 specificity levels remained similar (61% and 64% respectively, data not shown).

TABLE 4

SPECIFICITY AND SENSITIVITY OF CA125, IL-18 AND FGF-2 IN UNIVARIATE OR MULTIVARIATE ANALYSIS

|  | CA125 (U/ml) | | IL-18 (pg/ml) | | FGF-2 (pg/ml) | | CA125 + IL-18 + FGF2 | |
|---|---|---|---|---|---|---|---|---|
| Patient type | n > 50 U/ml | %+ | n > 215 pg/ml | %+ | n > 37 pg/ml | %+ | n | %+ |
| Specificity | | | | | | | | |
| NOSE + benign | 10/25 | 60 | 9/25 | 64 | 7/25 | 72 | 5/25 | 80 |
| Sensitivity | | | | | | | | |
| All EOC | 37/45 | 82 | 35/45 | 78 | 26/45 | 58 | 35/45 | 78 |
| LMP | 3/5 | 60 | 3/5 | 60 | 1/5 | 20 | 3/5 | 60 |
| Invasive EOC | 34/42 | 81 | 34/42 | 81 | 25/42 | 60 | 32/42 | 76 |
| Low stage | 6/11 | 55 | 6/11 | 55 | 7/11 | 64 | 7/11 | 64 |
| High stage | 31/34 | 91 | 29/34 | 85 | 20/34 | 59 | 28/34 | 73 |
| Serous | 28/29 | 97 | 26/29 | 90 | 19/29 | 66 | 27/29 | 93 |
| Endometroide | 2/3 | 67 | 2/3 | 67 | 1/3 | 33 | 1/3 | 33 |
| Clear cell | 1/5 | 20 | 3/5 | 60 | 4/5 | 80 | 3/5 | 60 |
| Mucinous | 1/3 | 33 | 2/3 | 67 | 1/3 | 33 | 1/3 | 33 |
| Brenner | 2/2 | 100 | 0/2 | 0 | 0/2 | 0 | 1/2 | 50 |
| Mixed | 3/3 | 100 | 2/3 | 67 | 1/3 | 33 | 2/3 | 67 |

EOC, Epithelial ovarian cancer;
LMP, low malignant potential tumor; low stage, stage I-II; high stage, stage III-IV;
%+, corresponds to percentage of NOSE + benign which do not score above the threshold (specificity).

Example 7

Diagnostic Potential of Serum IL-18 and FGF-2 as Combined Markers with CA125

The estimated correlation among the three serum markers (IL-18, FGF-2 and CA125) were low suggesting that they were complementary to each other and that a multivariate approach might outperform the CA125 assay alone. To validate this hypothesis a multivariate analysis was performed using a logistic binary regression algorithm. As shown in Table 5, FGF-2, but not IL-18, increased the diagnosis potential of CA125 (Odd Ratio from 5.24 to 6). However addition of both FGF-2 and IL-18 achieved a superior diagnostic potential (Odd Ratio=6.94, 0.95 (1.99-24.39), p=0.002) suggesting that the combination of both IL-18 and FGF-2 with CA125 allows a better sensitivity and specificity.

Scoring samples as malignant was also tested based on whether ELISA values were above the threshold for at least two of the three markers. In this analysis (Table 4), a sensitivity of 78% was achieved which was similar to that obtained with CA125 or IL-18 alone, but the specificity of diagnosis was dramatically increased from CA125 (60%), IL-18 (64%) or FGF-2 (72%) alone to 80% the combination of these serum markers (Table 4). Similar result was obtained in a larger set of samples (77%, data not shown).

TABLE 5

LOGISTIC BINARY REGRESSION (LBR) ANALYSIS OF MULTIVARIATE ANALYSIS OF CA125, IL-18 AND FGF-2

| | | p | OR | CI |
|---|---|---|---|---|
| LBR | CA125 | <0.001 | 5.24 | 2.07-13.33 |
| | CA125 + IL-18 | 0.002 | 4.78 | 1.81-12.66 |
| | CA125 + FGF-2 | 0.002 | 6 | 1.93-18.61 |
| | IL-18 + FGF-2 | 0.014 | 2.25 | 0.726-6.96 |
| | CA125 + IL-18 + FGF | 0.002 | 6.94 | 1.99-24.39 |

OR+: odd ratio.
CI: confidence interval 95%

Although the present invention has been described hereinabove by way of specific embodiments thereof, it can be modified, without departing from the spirit and nature of the subject invention as defined in the appended claims. Throughout this application, various references are referred to describe more fully the state of the art to which this invention pertains. The disclosures of these references are hereby incorporated by reference into the present disclosure.

REFERENCES 1.a) Auersperg, N., Wong, A. S., Choi, K. C., Kang, S. K., and Leung, P. C. Ovarian surface epithelium: biology, endocrinology, and pathology. Endocr Rev, 22: 255-288., 2001.

1.b) Agarwal, P., Bagga, R., Jain, V., Kalra, J. & Gopalan, S. Familial recurrent molar pregnancy: a case report. Acta Obstet Gynecol Scand 83, 213-4 (2004).

2. Serov, S. F., Scully, R., and Sobin, L. H. Histological typing of ovarian tumours., Vol. 9. Geneva: World Health Organization, 1973.

3. Chuaqui, R. F., Cole, K. A., Emmert-Buck, M. R., and Merino, M. J. Histopathology and molecular biology of ovarian epithelial tumors. Ann Diagn Pathol, 2: 195-207, 1998.

4. Crispens, M. A. Borderline ovarian tumours: a review of the recent literature. Curr Opin Obstet Gynecol, 15: 39-43, 2003.

5. Bast, R. C., Jr., Klug, T. L., Schaetzl, E., Lavin, P., Niloff, J. M., Greber, T. F., Zurawski, V. R., Jr., and Knapp, R. C. Monitoring human ovarian carcinoma with a combination of CA 125, CA 19-9, and carcinoembryonic antigen. Am J Obstet Gynecol, 149: 553-559, 1984.

6. Modugno, F. Ovarian cancer and high-risk women-implications for prevention, screening, and early detection. Gynecol Oncol, 91: 15-31, 2003.

7. Woolas, R. P., Xu, F. J., Jacobs, I. J., Yu, Y. H., Daly, L., Berchuck, A., Soper, J. T., Clarke-Pearson, D. L., Oram, D. H., and Bast, R. C., Jr. Elevation of multiple serum markers in patients with stage I ovarian cancer. J Natl Cancer Inst, 85: 1748-1751, 1993.

8. Meyer, T. and Rustin, G. J. Role of tumour markers in monitoring epithelial ovarian cancer. Br J Cancer, 82:1535-1538, 2000.

9. Le Page, C., Provencher, D., Maugard, C. M., Ouellet, V., and Mes-Masson, A. M. Signature of a silent killer: expression profiling in epithelial ovarian cancer. Expert Rev Mol Diagn, 4:157-167, 2004.

10. Mok, S. C., Chao, J., Skates, S., Wong, K., Yiu, G. K., Muto, M. G., Berkowitz, R. S., and Cramer, D. W. Prostasin, a potential serum marker for ovarian cancer: identification through microarray technology. J Natl Cancer Inst, 93: 1458-1464, 2001.

11. Kim, J. H., Skates, S. J., Uede, T., Wong, K. K., Schorge, J. O., Feltmate, C. M., Berkowitz, R. S., Cramer, D. W., and Mok, S. C. Osteopontin as a potential diagnostic biomarker for ovarian cancer. Jama, 287: 1671-1679, 2002.

12. McIntosh, M. W., Drescher, C., Karlan, B., Scholler, N., Urban, N., Hellstrom, K. E., and Hellstrom, I. Combining CA 125 and SMR serum markers for diagnosis and early detection of ovarian carcinoma. Gynecol Oncol, 95: 9-15, 2004.

13. Hellstrom, I., Raycraft, J., Hayden-Ledbetter, M., Ledbetter, J. A., Schummer, M., McIntosh, M., Drescher, C., Urban, N., and Hellstrom, K. E. The HE4 (WFDC2) protein is a biomarker for ovarian carcinoma. Cancer Res, 63: 3695-3700, 2003.

14. Woolas, R. P., Conaway, M. R., Xu, F., Jacobs, I. J., Yu, Y., Daly, L., Davies, A. P., O'Briant, K., Berchuck, A., Soper, J. T., and et al. Combinations of multiple serum markers are superior to individual assays for discriminating malignant from benign pelvic masses. Gynecol Oncol, 59: 111-116, 1995.

15. Kruk, P. A., Maines-Bandiera, S. L., and Auersperg, N. A simplified method to culture human ovarian surface epithelium. Lab. Invest., 63: 132-136, 1990.

16. Lounis, H., Provencher, D., Godbout, C., Fink, D., Milot, M. J., and Mes-Masson, A. M. Primary cultures of normal and tumoral human ovarian epithelium: a powerful tool for basic molecular studies. Exp. Cell Res., 215: 303-309, 1994.

17. Ouellet, V., Provencher, D M., Maugard, C. M., Le Page, C., Ren, F., Lussier, C., Novak, J., Ge, B., Hudson, T. J., Tonin, P. N., Mes-Masson, A. M. Discrimination between serous low malignant potential and invasive epithelial ovarian tumors using molecular profiling. Oncogene, 2005 Jul. 7; 24(9):4672-87.

18. Pfaffl, M. W. A new mathematical model for relative quantification in real-time RT-PCR. Nucleic Acids Res, 29: e45, 2001.

19. Tamayo, P., Slonim, D., Mesirov, J., Zhu, Q., Kitareewan, S., Dmitrovsky, E., Lander, E. S., and Golub, T. R. Interpreting patterns of gene expression with self-organizing maps: methods and application to hematopoietic differentiation. Proc Natl Acad Sci USA, 96: 2907-2912, 1999.

What is claimed is:

1. A method of diagnosing ovarian cancer in a sample from a subject comprising:
    (a) detecting the expression level of each of the markers FGF-2 and CA125 in the sample from the subject, wherein the subject is an adult woman; and
    (b) comparing the expression level of each of the markers in the sample from the subject to (i) the corresponding pre-determined threshold expression level for each of the markers; (ii) the expression level of each of the markers in a control sample; (iii) the expression level of each of the markers in a sample from the subject at an earlier time; or (iv) the expression level of each of the markers in a non-cancerous sample from the subject, and
    (c) determining whether the results indicate or not that the subject has ovarian cancer,
    wherein an expression level of each of the markers in the sample from the subject that is higher than (i) the pre-determined threshold expression levels for each of the markers; (ii) the expression level of each of the markers in the control sample; (iii) the expression level of each of the markers in a sample from the subject at an earlier time; or (iv) the expression level of each of the markers in a non-cancerous sample from the subject, is an indication that the subject has ovarian cancer.

2. The method of claim 1 wherein the subject is susceptible of having ovarian cancer.

3. The method of claim 1 wherein the subject is asymptomatic for ovarian cancer.

4. The method of claim 1, wherein the expression level of each of the markers in the subject sample is compared to the corresponding pre-determined threshold expression level for each of the markers, and wherein an expression level of each of the markers in the subject sample that is higher than the pre-determined threshold expression level for each of the markers is an indication that the subject has ovarian cancer.

5. The method of claim 1, wherein the expression level of each of the markers in the subject sample is compared to the expression level of each of the markers in the control sample, and wherein an expression level of each of the markers that is higher in the subject sample than in the control sample is an indication that the subject has ovarian cancer.

6. The method of claim 1, wherein the expression level of each of the markers in the subject sample is compared to the expression level of each of the markers in the sample from the subject at an earlier time, and wherein an expression level of each of the markers that is higher in the subject sample than in the sample from the subject at an earlier time is an indication that the subject has ovarian cancer.

7. The method of claim 1, wherein the expression level of each of the markers in the subject sample is compared to the expression level of each of the markers in a non-cancerous sample from the subject, and wherein an expression level of each of the markers that is higher in the subject sample than in the non-cancerous sample from the subject is an indication that the subject has ovarian cancer.

8. The method of claim 1, wherein the threshold expression level for each of the markers is determined by Receiver Operator Curves comparing the concentration of each of the markers in an ovarian cancer-free control population with that in a population that has ovarian cancer.

9. The method of claim 1, wherein the expression is determined at the polypeptide level.

10. The method of claim 9, wherein the expression is determined using an immunoassay.

11. The method of claim 10, wherein the immunoassay is enzyme-linked immunosorbent assay (ELISA).

12. The method of claim 10, wherein the expression level of each of the markers is above the following pre-determined threshold expression levels: 50 U/ml for CA125 and 37 pg/ml for FGF-2.

13. The method of claim 1, wherein step (a) further comprises detecting the expression level of marker IL-18 in the sample.

14. The method of claim 12, wherein step (a) further comprises detecting the expression level of marker IL-18 in the sample, and wherein the expression level of IL-18 in the sample is above the pre-determined threshold expression level of 215 pg/ml for this marker.

15. The method of claim 1, wherein the subject sample is a body fluid sample.

16. The method of claim 15, wherein the subject sample is blood, plasma or serum.

17. The method of claim 15, wherein the subject sample is serum.

18. The method of claim 1, wherein the subject sample is primary culture cells derived from an ovarian tumor sample from the subject.

19. The method of claim 1, wherein the subject is a human.

20. The method of claim 1, wherein the ovarian cancer is epithelial ovarian carcinoma (EOC).

21. The method of claim 1, wherein the method is in vitro.

* * * * *